United States Patent
Storck et al.

(10) Patent No.: US 8,288,377 B2
(45) Date of Patent: Oct. 16, 2012

(54) INHIBITORS OF THE INTERACTION BETWEEN MDM2 AND P53

(75) Inventors: Pierre-Henri Storck, Ramsgate (GB); Bruno Schoentjes, Bois-Guillaume (FR); Arnaud Marcel Pierre Piettre, Sierentz (FR); Philipp Ermert, Allschwil (CH); Virginie Sophie Poncelet, Le Manoir sur Seine (FR); Imre Christian Francis Csoka, Louviers (FR)

(73) Assignee: Janssen Pharmaceutica N.V., Beerse (BE)

( * ) Notice: Subject to any disclaimer, the term of this patent is extended or adjusted under 35 U.S.C. 154(b) by 235 days.

(21) Appl. No.: 12/678,680

(22) PCT Filed: Sep. 19, 2008

(86) PCT No.: PCT/EP2008/062551
§ 371 (c)(1),
(2), (4) Date: Mar. 17, 2010

(87) PCT Pub. No.: WO2009/037343
PCT Pub. Date: Mar. 26, 2009

(65) Prior Publication Data
US 2010/0216770 A1    Aug. 26, 2010

(30) Foreign Application Priority Data
Sep. 21, 2007   (EP) .................................. 07116897.5

(51) Int. Cl.
*C07D 413/14* (2006.01)
*A61K 31/538* (2006.01)

(52) U.S. Cl. .................................... 514/230.5; 544/105

(58) Field of Classification Search .................. 544/105; 514/230.5
See application file for complete search history.

(56) References Cited

FOREIGN PATENT DOCUMENTS
| WO | WO 2006/032631 A | 3/2006 |
| WO | WO 2007/107543 A | 9/2007 |
| WO | WO 2007/107545 A | 9/2007 |

OTHER PUBLICATIONS

Blattner et al., "Hypophosphorylation of Mdm2 Augments p52 Stability", *Mol. Cell. Biol.* 22: 6170-6182, 2002.
Vousden, K.H., "p53: Death Star", *Cell* 103(5): 691-694, 2000.
International Search Report dated Dec. 3, 2008 for Appln. No. PCT/EP2008/062551.

*Primary Examiner* — Kahsay T Habte
(74) *Attorney, Agent, or Firm* — Rajiv S. Shah

(57) ABSTRACT

The present invention provides compounds of formula (I), their use as an inhibitor of a p53-MDM2 interaction as well as pharmaceutical compositions comprising said compounds:

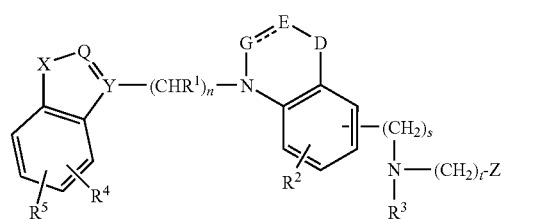

wherein n, s, t, $R^1$, $R^2$, $R^3$, $R^4$, $R^5$, X, Y, Q, Z, G, E and D have defined meanings.

15 Claims, No Drawings

US 8,288,377 B2

INHIBITORS OF THE INTERACTION BETWEEN MDM2 AND P53

CROSS REFERENCE TO RELATED APPLICATIONS

This application is a national stage application of Patent Application No. PCT/EP2008/062551, filed Sep. 19, 2008, which application claims priority from EPO Patent Application No. 07116897.5, filed Sep. 21, 2007, the entire disclosures of which are hereby incorporated by reference in their entirety.

FIELD OF THE INVENTION

The present invention relates to compounds and compositions containing said compounds acting as inhibitors of the interaction between MDM2 and p53, in particular modulators of the MDM2-proteasome interaction. The invention also provides processes for the preparation of the disclosed compounds and compositions and methods of using them, for instance as a medicine.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer.

MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53. However, in tumours with wild-type p53, the equilibrium concentration of active p53 can be increased by antagonising the interaction between MDM2 and p53. Other activities of MDM2 are also required for p53 degradation, as evidenced by the accumulation of ubiquitylated p53 when phosphorylation in the central domain of HDM2 is abrogated (Blattner et al., Hypophosphorylation of Mdm2 augments p53 stability. (2002) *Mol. Cell. Biol.*, 22, 6170-6182). The association of HDM2 with different subunits of the 26S proteasome such as S4, S5a, S6a and S6b ($3^{rd}$ Mdm2 workshop, September 2005 in Constance, Germany) might play a key role in this process. Thus, p53 concentrations can also be increased by modulating the MDM2-proteasome interaction. This will result in restoration of the p53-mediated pro-apoptotic and anti-proliferative effects in such tumour cells. MDM2 antagonists might even exhibit anti-proliferative effects in tumour cells that are devoid of functional p53.

This positions the HDM2 protein as an attractive target for the development of anti-cancer therapy.

MDM2 is a cellular proto-oncogene. Over-expression of MDM2 has been observed in a range of cancers. MDM2 is over-expressed in a variety of tumours due to gene amplification or increased transcription or translation. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing MDM2 are free to continue to proliferate and assume a tumorigenic phenotype. Under these conditions disruption of the interaction of p53 and MDM2 would release the p53 and thus allow normal signals of growth arrest and/or apoptosis to function.

MDM2 may also have separate functions in addition to inhibition of p53. The number of MDM2 substrates is rapidly expanding. For example, it has been shown that MDM2 interacts directly with the pRb-regulated transcription factor E2F1/DP1. This interaction could be crucial for the p53-independent oncogenic activities of MDM2. A domain of E2F1 shows striking similarity to the MDM2-binding domain of p53. Since the interactions of MDM2 with both p53 and E2F1 locate to the same binding site on MDM2, it can be expected that MDM2/p53 antagonists will not only activate cellular p53 but also modulate E2F1 activities, which are commonly deregulated in tumour cells. Other key examples of MDM2 substrates include p63, p73, $p21^{waf1,cip1}$.

Also the therapeutic effectiveness of DNA damaging agents currently used (chemotherapy and radiotherapy), may be limited through the negative regulation of p53 by MDM2. Thus if the MDM2 feed-back inhibition of p53 is interrupted, an increase in functional p53 levels will increase the therapeutic effectiveness of such agents by restoring the wild-type p53 function that leads to apoptosis and/or reversing of p53-associated drug resistance. It was demonstrated that combining MDM2 inhibition and DNA-damaging treatments in vivo led to synergistic anti-tumour effects (Vousden K. H., Cell, Vol. 103, 691-694, 2000).

Thus disruption of the interaction of MDM2 and p53 offers an approach for therapeutic intervention in tumours with wild-type or mutant p53, might even exhibit anti-proliferative effects in tumour cells that are devoid of functional p53 and furthermore can sensitise tumorigenic cells for chemotherapy and radiotherapy.

BACKGROUND OF THE INVENTION

WO 2006/032631, WO 2007/107545 and WO 2007/107543 disclose inhibitors of the interaction between MDM2 and p53, useful inter alia in treating tumours and enhancing the effectiveness of chemotherapy and radiotherapy.

The compounds of the instant invention differ structurally from the compounds of WO 2006/032631, WO 2007/107545 and WO 2007/107543 by comprising an N-containing ring fused to the central phenyl ring and wherein the N is linked to a bicycle.

Unexpectedly, this substantial structural modification yields novel compounds which retain or may even show improved inhibitory activity or useful properties. Hence, the invention provides a further useful series of effective and potent small molecules that inhibit the interactions between MDM2 and p53.

DESCRIPTION OF THE INVENTION

The present invention provides compounds and compositions for, and methods of, inhibiting the interactions between MDM2 and p53 for treating proliferative disease, including tumours and cancer. Furthermore, the compounds and compositions of the invention are useful in enhancing the effectiveness of chemotherapy and radiotherapy.

Accordingly, in an aspect the invention provides a compound of formula (I):

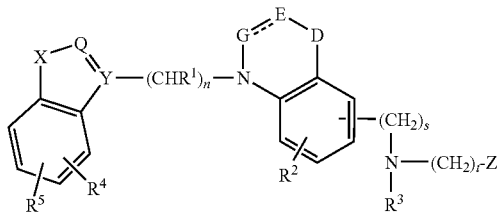

(I)

including any stereochemically isomeric form thereof, wherein n is 0, 1, 2, 3 or 4 and when n is 0 then a direct bond is intended, and wherein $R^1$ on each carbon of the —(CHR$^1$)$_n$— group is each independently selected from hydrogen, halo, hydroxy, amino, mono- or di($C_{1-6}$alkyl)amino, $C_{1-6}$alkyl, aryl, heteroaryl, $C_{3-7}$cycloalkyl, aryl$C_{1-6}$alkyl, heteroaryl$C_{1-6}$ alkyl, and $C_{3-7}$cycloalkyl-$C_{1-6}$alkyl, any of said mono- or di($C_{1-6}$alkyl)amino, $C_{1-6}$alkyl, aryl, heteroaryl, $C_{3-7}$cycloalkyl, aryl$C_{1-6}$alkyl, heteroaryl$C_{1-6}$alkyl or $C_{3-7}$cycloalkyl$C_{1-6}$alkyl being optionally and independently substituted with one or more, preferably one or two, substituents selected from hydroxy, amino, aryl and heteroaryl;

s is 0 or 1 and when s is 0 then a direct bond is intended;
t is 0 or 1 and when t is 0 then a direct bond is intended;
$R^2$ is selected from hydrogen, halo, cyano, amino;
polyhalo$C_{1-6}$alkyl;

$C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;

$R^3$ is hydrogen; $C_{1-6}$alkyl; aryl; heteroaryl; $C_{3-7}$cycloalkyl; $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;

X is NR$^6$, S or O;

—G═E— is —CR$^7$═CR$^8$— then the dotted line is a bond, —CR$^7$R$^9$—CR$^8$R$^{10}$—, —C(═O)—CR$^8$R$^{10}$— or —CR$^7$R$^9$—C(═O)—, wherein $R^7$, $R^8$, $R^9$ or $R^{10}$ are each independently selected from:

hydrogen, halo, hydroxy, cyano;
polyhalo$C_{1-6}$alkyl;

$C_{1-6}$alkyl, $C_{3-7}$cycloalkyl, $C_{2-6}$alkenyl, aryl, heteroaryl, aryl$C_{1-6}$alkyl, heteroaryl$C_{1-6}$alkyl, $C_{3-7}$cycloalkyl$C_{1-6}$ alkyl, morpholinyl, piperidinyl, pyrrolidinyl, piperazinyl, $C_{1-6}$alkyloxy, $C_{3-7}$cycloalkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;

or wherein any of $R^7$ and $R^9$ together, or $R^8$ and $R^{10}$ together form a bivalent radical selected from —(CH$_2$)$_2$—O—(CH$_2$)$_2$—, —(CH$_2$)$_2$—S—(CH$_2$)$_2$— and —(CH$_2$)$_2$—NR$^{21}$—(CH$_2$)$_2$— wherein R$^{21}$ is hydrogen, $C_{1-6}$alkyl or $C_{1-6}$alkyloxyalkyl;

or wherein any of $R^7$ and $R^9$ together, or $R^8$ and $R^{10}$ together form a bivalent radical —(CH$_2$)$_m$—, wherein m is 2, 3, 4, 5 or 6;

-D- is —O—, —CHR$^{20}$— or —NR$^{20}$—, wherein R$^{20}$ is selected from hydrogen, $C_{1-6}$alkyl, $C_{1-6}$alkylcarbonyl and $C_{1-6}$alkyloxycarbonyl;

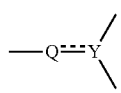

is —CR$^{19}$═C< and then the dotted line is a bond, —C(═O)—CH<, —C(═O)—N<, —CHR$^{19}$—CH<, or —CHR$^{19}$—N<, wherein each R$^{19}$ is independently hydrogen or $C_{1-6}$alkyl;

$R^4$ and $R^5$ are each independently hydrogen, halo, $C_{1-6}$alkyl, hydroxy$C_{1-6}$alkyl, polyhalo$C_{1-6}$alkyl, cyano, cyano$C_{1-6}$alkyl, hydroxy, amino, $C_{2-6}$alkenyl or $C_{1-6}$alkyloxy, or $R^4$ and $R^5$ together form a bivalent radical selected from methylenedioxy or ethylenedioxy;

$R^6$ is hydrogen, $C_{1-6}$alkyl, $C_{1-6}$alkylcarbonyl or $C_{1-6}$alkyloxycarbonyl;

Z is a radical selected from

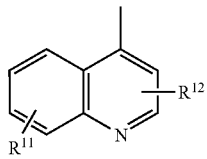
(a-1)

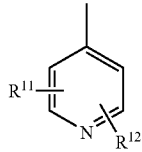
(a-2)

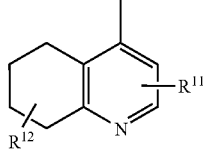
(a-3)

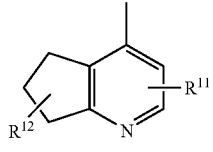
(a-4)

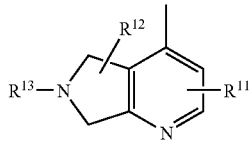
(a-5)

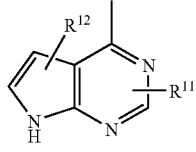
(a-6)

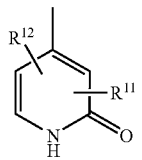
(a-7)

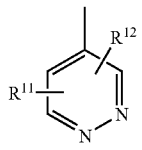
(a-8)

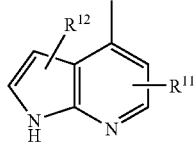
(a-9)

wherein
$R^{11}$ or $R^{12}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo-$C_{1-6}$alkyl, aryl, heteroaryl, aryl$C_{1-6}$alkyl, heteroaryl$C_{1-6}$alkyl, aryl(hydroxy)-$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and $-(CH_2)_v-(C(=O))_r-(CHR^{18})_u-NR^{14}R^{15}$, wherein
v is 0, 1, 2, 3, 4, 5, or 6 and when v is 0 then a direct bond is intended;
r is 0 or 1 and when r is 0 then a direct bond is intended;
u is 0, 1, 2, 3, 4, 5, or 6 and when u is 0 then a direct bond is intended;
$R^{18}$ is hydrogen or $C_{1-6}$alkyl;
$R^{14}$ and $R^{15}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkyl; $C_{3-7}$cycloalkylcarbonyl; $-(CH_2)_k-NR^{16}R^{17}$; $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl, or
$R^{14}$ and $R^{15}$ together with the nitrogen to which they are attached form morpholinyl; piperidinyl; pyrrolidinyl; piperazinyl; or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein
k is 0, 1, 2, 3, 4, 5, or 6 and when k is 0 then a direct bond is intended;
$R^{16}$ and $R^{17}$ are each independently selected from hydrogen; $C_{1-12}$alkyl; aryl$C_{1-6}$alkyloxycarbonyl; $C_{3-7}$cycloalkyl; $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or
$R^{16}$ and $R^{17}$ together with the nitrogen to which they are attached form morpholinyl, piperazinyl, or piperazinyl substituted with $C_{1-6}$alkyloxycarbonyl;
$R^{13}$ is hydrogen; $C_{1-6}$alkyl; $C_{3-7}$cycloalkyl; $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;

aryl is phenyl or naphthalenyl;
each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and
each phenyl or naphthalenyl can optionally be substituted with a bivalent radical selected from methylenedioxy and ethylenedioxy;

heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

an N-oxide form thereof, an addition salt thereof or a solvate thereof.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms may be used as such or in composite terms.

As used herein, halo is generic to fluoro, chloro, bromo and iodo. $C_{1-6}$alkyl defines straight- and branched-chain saturated hydrocarbon radicals having from 1 to 6 carbon atoms such as, e.g., methyl, ethyl, propyl, butyl, pentyl, hexyl, 1-methylethyl, 2-methylpropyl, 2-methyl-butyl, 2-methylpentyl and the like. $C_{1-12}$ alkyl includes $C_{1-6}$alkyl and the higher straight- and branched-chain homologues thereof having 7 to 12 carbon atoms such as, for example, heptyl, octyl, nonyl, decyl, undecyl, dodecyl and the like. Hydroxy$C_{1-6}$alkyl refers to a $C_{1-6}$alkyl as defined herein, wherein one or more (e.g., one, two, three or more) hydrogens of said $C_{1-6}$alkyl are replaced with a hydroxyl substituent. Polyhalo$C_{1-6}$alkyl refers to a $C_{1-6}$alkyl as defined herein, wherein one or more hydrogens of said $C_{1-6}$alkyl are replaced with identical or different halogen substituents; the term also encompasses perhalo$C_{1-6}$alkyls, i.e., $C_{1-6}$alkyl as defined herein, wherein all hydrogens of said $C_{1-6}$alkyl are replaced with identical or different halogen substituents—for example, trihalomethyl defines methyl containing three identical or different halo substituents, such as, e.g., trifluoromethyl. $C_{2-6}$alkenyl defines straight- and branched-chain hydrocarbon radicals containing one or more double bonds, preferably one double bond, and having from 2 to 6 carbon atoms such as, for example, ethenyl, 2-propenyl, 3-butenyl, 2-pentenyl, 3-pentenyl, 3-methyl-2-butenyl, and the like. $C_{3-7}$cycloalkyl includes alicyclic saturated and unsaturated hydrocarbon groups having from 3 to 7 carbon atoms, such as cyclopropyl, cyclobutyl, cyclopentyl, cyclopentenyl, cyclohexyl, cyclohexenyl, cycloheptyl, and the like. Preferably $C_{3-7}$cycloalkyl includes alicyclic saturated hydrocarbon groups having from 3 to 7 carbon atoms, such as cyclopropyl, cyclobutyl, cyclopentyl, cyclohexyl, cycloheptyl, and the like.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts, metal complexes and the salts thereof, that the compounds of formula (I) are able to form.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g., hydrochloric or hydrobromic acid, sulphuric, nitric, phosphoric and the like acids; or organic acids such as, for example, acetic, propanoic, hydroxyacetic, lactic, pyruvic, oxalic, malonic, succinic (i.e., butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine and the like.

Preferably, the term addition salt means a pharmaceutically acceptable acid or base addition salt.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g., methylsulfonates, 4-methylphenylsulfonates, salicylates, benzoates and the like of the metals of the second main group of the periodical system, e.g., the magnesium or calcium salts, of the third or fourth main group, e.g., aluminium, tin, lead, as well as the first to the eighth transition groups of the periodical system such as, for example, chromium, manganese, iron, cobalt, nickel, copper, zinc and the like.

The term "stereochemically isomeric forms of compounds of formula (I)", as used herein, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e., minimum 90% of one isomer and maximum 10% of the other possible isomers) up to a stereoisomeric excess of 100% (i.e., 100% of one isomer and none of the other), more preferably, compounds or intermediates having a stereoisomeric excess of 90% up to 100%, even more preferably having a stereoisomeric excess of 94% up to 100% and most preferably having a stereoisomeric excess of 97% up to 100%. The terms "enantiomerically pure" and "diastereomerically pure" should be understood in a similar way, but then having regard to the enantiomeric excess respectively diastereomeric excess of the mixture in question.

The N-oxide forms of the compounds of formula (I) are meant to comprise those compounds of formula (I) wherein one or several tertiary nitrogen atoms are oxidized to the so-called N-oxide, particularly those N-oxides wherein one or more of the piperidine-, piperazine- or pyridazinyl-nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g., sodium peroxide, potassium peroxide; appropriate organic peroxides may comprise inter alia peroxy acids such as, for example, benzenecarboperoxoic acid or halo substituted benzenecarboperoxoic acid, e.g., 3-chlorobenzenecarboperoxoic acid, peroxoalkanoic acids, e.g., peroxoacetic acid, alkylhydroperoxides, e.g., t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) may form solvates, for example, with water (i.e., hydrates) or common organic solvents e.g. alcohols. As used herein, the term "solvate" means a physical association of the compounds of formula (I) with one or more solvent molecules, as well as the salts thereof. This physical association involves varying degrees of ionic and other bonding, including hydrogen bonding. In certain instances the solvate will be capable of isolation, for example, when one or more solvent molecules are incorporated in the crystal lattice of the crystalline solid. The term "solvate" is intended to encompass both solution-phase and isolatable solvates. Non-limiting examples of suitable solvates include hydrates, ethanolates, methanolates, and the like.

Furthermore, the compounds of the present invention may be amorphous or may have one or more crystalline polymorph forms, as such forms are intended to be included in the scope of the invention.

The invention encompasses any isotopes of atoms present in the compounds of the invention. For example, isotopes of hydrogen include tritium and deuterium and isotopes of carbon include $^{13}C$ and $^{14}C$.

Whenever used hereinafter, the term "compounds of formula (I)" is meant to include also the N-oxide forms, the acid or base addition salts particularly the pharmaceutically acceptable acid or base addition salts, the solvates and all stereoisomeric forms of said compounds of formula (I).

A first group of interesting compounds (herein referred to as group "G1") consists of those compounds of formula (I) wherein any one or more or all of the following restrictions apply:

a) n is 1, 2 or 3;
b) $R^1$ on each carbon of the —$(CHR^1)_n$— group is each independently selected from hydrogen, hydroxy, amino, mono- or di($C_{1-6}$alkyl)amino, $C_{1-6}$alkyl, aryl$C_{1-6}$alkyl and heteroaryl$C_{1-6}$alkyl,
any of said mono- or di($C_{1-6}$alkyl)amino, $C_{1-6}$alkyl, aryl$C_{1-6}$alkyl or heteroaryl-$C_{1-6}$alkyl being optionally and independently substituted with one or more, preferably one or two, substituents selected from hydroxy, amino, aryl and heteroaryl;
c) when any one or any two $R^1$ substituents in the —$(CHR^1)_n$— group are different from hydrogen, the other $R^1$ substituents in the —$(CHR^1)_n$— group are each hydrogen;
d) $R^2$ is selected from hydrogen, halo, cyano, amino, mono- or di($C_{1-6}$alkyl)amino,
$C_{1-6}$alkyl, aryl, heteroaryl, aryl$C_{1-6}$alkyl, heteroaryl$C_{1-6}$alkyl, hydroxy$C_{1-6}$alkyl, polyhalo$C_{1-6}$alkyl preferably perhalo$C_{1-6}$alkyl, $C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino, morpholinyl, piperidinyl, pyrrolidinyl and piperazinyl,
any of said mono- or di($C_{1-6}$alkyl)amino, $C_{1-6}$alkyl, aryl, heteroaryl, aryl$C_{1-6}$alkyl, heteroaryl$C_{1-6}$alkyl, hydroxy$C_{1-6}$alkyl, polyhalo$C_{1-6}$alkyl preferably perhalo-$C_{1-6}$alkyl, $C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino, morpholinyl, piperidinyl, pyrrolidinyl or piperazinyl being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl and $C_{1-6}$alkyloxy;
e) $R^3$ is hydrogen; $C_{1-6}$alkyl; $C_{3-7}$cycloalkyl; $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;
f) -D- is —O—, —$CH_2$— or —$NR^{20}$—, wherein $R^{20}$ is selected from hydrogen and $C_{1-6}$alkyl; preferably -D- is —O— or —$NR^{20}$—;

g)

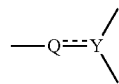

is —$CR^{19}$=C< wherein $R^{19}$ is hydrogen or $C_{1-6}$alkyl;
h) $R^4$ and $R^5$ are each independently hydrogen, halo, $C_{1-6}$alkyl, hydroxyl-$C_{1-6}$alkyl, polyhalo$C_{1-6}$alkyl, cyano, cyano$C_{1-6}$alkyl, hydroxy, amino, $C_{2-6}$alkenyl, or $C_{1-6}$alkyloxy; more preferably hydrogen, halo, $C_{1-6}$alkyl, polyhalo$C_{1-6}$alkyl, cyano, cyano$C_{1-6}$alkyl, hydroxy, amino, or $C_{1-6}$alkyloxy; even more preferably $R^4$ and $R^5$ are each independently hydrogen, halo, $C_{1-6}$alkyl, polyhalo$C_{1-6}$alkyl, hydroxy, amino or $C_{1-6}$alkyloxy;
i) Z is a radical selected from (a-1), (a-2), (a-3), (a-4) and (a-5);
j) $R^{11}$ or $R^{12}$ are each independently selected from hydrogen, halo, hydroxy, amino, $C_{1-6}$alkyl, nitro, polyhalo$C_{1-6}$ alkyl, cyano, cyano$C_{1-6}$alkyl, tetrazolo$C_{1-6}$alkyl, aryl, heteroaryl, heteroaryl$C_{1-6}$alkyl, aryl(hydroxy)$C_{1-6}$alkyl, arylcarbonyl, $C_{1-6}$alkylcarbonyl, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl, hydroxycarbonyl-$C_{1-6}$alkyl and —(CH$_2$)$_v$—(C(=O))$_r$—(CHR$^{18}$)$_u$—NR$^{14}$R$^{15}$;

v is 0 or 1;
r is 0 or 1;
u is 0 or 1;
R$^{14}$ and R$^{15}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkylcarbonyl; —(CH$_2$)$_k$—NR$^{16}$R$^{17}$; $C_{1-12}$alkyl substituted with a substituent selected from hydroxy, hydroxycarbonyl, cyano, $C_{1-6}$alkyloxycarbonyl or aryl; or R$^{14}$ and R$^{15}$ together with the nitrogen to which they are attached form morpholinyl, pyrrolidinyl, piperazinyl or piperazinyl substituted with a substituent selected from $C_{1-6}$alkyl or aryl$C_{1-6}$alkyloxycarbonyl;
k is 2;
R$^{16}$ and R$^{17}$ are each independently selected from hydrogen, $C_{1-6}$alkyl or aryl$C_{1-6}$alkyloxycarbonyl; or R$^{16}$ and R$^{17}$ together with the nitrogen to which they are attached form morpholinyl or piperazinyl, or piperazinyl substituted with $C_{1-6}$alkyloxycarbonyl;
k) R$^{13}$ is hydrogen or $C_{1-6}$alkyl;
l) X is NR$^6$.

A second group of interesting compounds (herein referred to as group "G2") consists of those compounds of formula (I) wherein any one or more or all of the following restrictions apply:
a) n is 1, 2 or 3, preferably n is 2;
b) R$^1$ on each carbon of the —(CHR$^1$)$_n$— group is each independently selected from hydrogen, hydroxy, amino, mono- or di($C_{1-6}$alkyl)amino, $C_{1-6}$alkyl, aryl$C_{1-6}$alkyl and heteroaryl$C_{1-6}$alkyl,
c) when any one R$^1$ substituent in the —(CHR$^1$)$_n$— group is different from hydrogen, the other R$^1$ substituents in the —(CHR$^1$)$_n$— group are each hydrogen;
d) s is 0;
e) t is 0 or 1, preferably t is 0;
f) R$^2$ is selected from hydrogen, halo, cyano, amino, mono- or di($C_{1-6}$alkyl)amino, $C_{1-6}$alkyl, aryl, heteroaryl, aryl$C_{1-6}$alkyl, heteroaryl$C_{1-6}$alkyl, hydroxy$C_{1-6}$alkyl, polyhalo$C_{1-6}$alkyl preferably perhalo$C_{1-6}$alkyl, $C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino, morpholinyl, piperidinyl, pyrrolidinyl and piperazinyl;
g) R$^3$ is hydrogen or $C_{1-6}$alkyl;
h) -D- is —O—, —CH$_2$— or —NR$^{20}$—, wherein R$^{20}$ is hydrogen or $C_{1-6}$alkyl; preferably -D- is —O— or —NR$^{20}$—;

i)

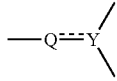

is —CR$^{19}$=C< wherein R$^{19}$ is hydrogen or $C_{1-6}$alkyl;

j) R$^4$ and R$^5$ are each independently hydrogen, halo, $C_{1-6}$alkyl, hydroxy or $C_{1-6}$alkyloxy;
k) R$^6$ is hydrogen or $C_{1-6}$alkyl;
l) Z is a radical selected from (a-1), (a-2), (a-3), (a-4) and (a-5);
m) R$^{11}$ or R$^{12}$ are each independently selected from hydrogen, hydroxy, amino, $C_{1-6}$alkyl, nitro, polyhalo$C_{1-6}$alkyl, cyano, aryl, aryl$C_{1-6}$alkyl, aryl(hydroxy)$C_{1-6}$alkyl, arylcarbonyl, $C_{1-6}$alkyloxy, $C_{1-6}$alkyloxy$C_{1-6}$alkyl, $C_{1-6}$alkyloxycarbonyl, aminocarbonyl, hydroxy$C_{1-6}$alkyl, amino$C_{1-6}$alkyl, hydroxycarbonyl and —(CH$_2$)$_v$—(C(=O))$_r$—(CH$_2$)$_u$—NR$^{14}$R$^{15}$;

v is 0 or 1;
r is 0 or 1;
u is 0;
R$^{14}$ and R$^{15}$ are each independently selected from hydrogen, $C_{1-6}$alkyl, —(CH$_2$)$_k$—NR$^{16}$R$^{17}$ and $C_{1-12}$alkyl substituted with hydroxy; or
R$^{14}$ and R$^{15}$ together with the nitrogen to which they are attached form pyrrolidinyl;
k is 2;
R$^{16}$ and R$^{17}$ are each independently hydrogen or $C_{1-6}$alkyl;

n) R$^{13}$ is hydrogen or $C_{1-6}$alkyl;
o) aryl is phenyl or phenyl substituted with halo; and
p) heteroaryl is pyridinyl, indolyl, oxadiazolyl or tetrazolyl; and each pyridinyl, indolyl, oxadiazolyl or tetrazolyl can optionally be substituted with one substituent selected from $C_{1-6}$alkyl, aryl and aryl$C_{1-6}$alkyl;
q) X is NR$^6$.

A third group of interesting compounds (herein referred to as group "G3") consists of those compounds of formula (I) wherein any one or more or all of the following restrictions apply:
a) n is 1, 2 or 3, preferably n is 2;
b) R$^1$ on each carbon of the —(CHR$^1$)$_n$— group is each independently selected from hydrogen, aryl$C_{1-6}$alkyl, hydroxy or heteroaryl$C_{1-6}$alkyl;
c) when any one R$^1$ substituent in the —(CHR$^1$)$_n$— group is different from hydrogen, the other R$^1$ substituents in the —(CHR$^1$)$_n$— group are each hydrogen;
d) s is 0;
e) t is 0;
f) R$^2$ is selected from hydrogen, halo, cyano, $C_{1-6}$alkyl, hydroxy$C_{1-6}$alkyl, polyhalo$C_{1-6}$alkyl preferably perhalo$C_{1-6}$alkyl, $C_{1-6}$alkyloxy, $C_{1-6}$alkylcarbonylamino and morpholinyl;
g) R$^3$ is hydrogen or $C_{1-6}$alkyl, preferably hydrogen;
h) -D- is —O—, —CH$_2$— or —NH—; preferably -D- is —O— or —NH—; more preferably -D- is i)

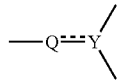

is —CH=C<;

j) R$^4$ and R$^5$ are each independently hydrogen, $C_{1-6}$alkyl or $C_{1-6}$alkyloxy;
k) R$^6$ is hydrogen or $C_{1-6}$alkyl, preferably hydrogen;
l) Z is a radical selected from (a-1), (a-2), (a-3), (a-4) and (a-5), preferably Z is a radical selected from (a-1), (a-2) and (a-4);

m) $R^{11}$ or $R^{12}$ are each independently selected from hydrogen, hydroxy and hydroxy$C_{1-6}$alkyl;

n) $R^{13}$ is hydrogen or $C_{1-6}$alkyl, preferably hydrogen;

o) aryl is phenyl or phenyl substituted with halo; and p) heteroaryl is pyridinyl or indolyl;

q) X is $NR^6$.

A fourth group of interesting compounds (herein referred to as group "G4") consists of those compounds of formula (I) wherein any one or more or all of the following restrictions apply:

a) n is 2;

b) each $R^1$ is hydrogen;

c) s is 0;

d) t is 0;

e) $R^2$ is selected from hydrogen, halo, cyano, $C_{1-6}$alkyl, hydroxy$C_{1-6}$alkyl, polyhalo$C_{1-6}$alkyl preferably perhalo$C_{1-6}$alkyl, $C_{1-6}$alkyloxy, $C_{1-6}$alkylcarbonylamino and morpholinyl, more preferably $R^2$ is selected from hydrogen, halo, $C_{1-6}$alkyl, polyhalo$C_{1-6}$alkyl preferably perhalo$C_{1-6}$alkyl, and $C_{1-6}$alkyloxy;

f) $R^3$ is hydrogen;

g) -D- is —O—, —CH$_2$— or —NH—; -D- is —O— or —NH—; more preferably -D- is —O—;

h)

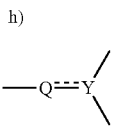

is —CH═C<;

i) $R^4$ and $R^5$ are each independently hydrogen, $C_{1-6}$alkyl or $C_{1-6}$alkyloxy;

j) $R^6$ is hydrogen;

k) Z is a radical selected from (a-1), (a-2) and (a-4), preferably Z is (a-2) or (a-4);

l) $R^{11}$ or $R^{12}$ are each independently selected from hydrogen, hydroxy and hydroxy$C_{1-6}$alkyl;

m) $R^{13}$ is hydrogen;

n) aryl is phenyl or phenyl substituted with halo; and o) heteroaryl is pyridinyl or indolyl;

p) X is $NR^6$, S or O, preferably X is $NR^6$.

A fifth group of interesting compounds (herein referred to as group "G5") consists of those compounds of formula (I) wherein any one or more or all of the following restrictions apply:

a) n is 2;

b) each $R^1$ is hydrogen;

c) s is 0;

d) t is 0;

e) $R^2$ is selected from hydrogen, fluoro, chloro, bromo, cyano, methyl, hydroxymethyl, trihalomethyl preferably trifluoromethyl, methyloxy, methylcarbonylamino and morpholinyl, more preferably $R^2$ is selected from hydrogen, fluoro, chloro, methyl, trifluoromethyl and methyloxy;

f) $R^3$ is hydrogen;

g) -D- is —O—, —CH$_2$— or —NH—; preferably -D- is —O— or —NH—, more preferably -D- is —O—;

h)

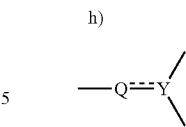

is —CH═C<;

i) $R^4$ and $R^5$ are each independently hydrogen, methyl or methyloxy;

j) $R^6$ is hydrogen;

k) Z is a radical selected from (a-1), (a-2) and (a-4), preferably Z is (a-2) or (a-4), even more preferably Z is (a-4);

l) $R^{11}$ or $R^{12}$ are each independently selected from hydrogen, hydroxy and hydroxymethyl;

m) $R^{13}$ is hydrogen;

n) aryl is phenyl or phenyl substituted with halo; and o) heteroaryl is pyridinyl or indolyl;

p) X is $NR^6$, S or O, preferably X is $NR^6$.

A sixth group of interesting compounds (herein referred to as group "G6") consists of those compounds of formula (I) or any subgroup thereof, wherein:

n is 1, 2 or 3, preferably n is 2;

$R^1$ on each carbon of the —(CHR$^1$)$_n$— group is each independently selected from hydrogen, hydroxy, amino, mono- or di($C_{1-6}$alkyl)amino, $C_{1-6}$alkyl, aryl$C_{1-6}$alkyl and heteroaryl$C_{1-6}$alkyl;

when any one $R^1$ substituent in the —(CHR$^1$)$_n$— group is different from hydrogen, the other $R^1$ substituents in the —(CHR$^1$)$_n$— group are each hydrogen;

s is 0;

t is 0 or 1, preferably t is 0;

$R^2$ is selected from hydrogen, halo, cyano, amino, mono- or di($C_{1-6}$alkyl)amino, $C_{1-6}$alkyl, aryl, heteroaryl, aryl$C_{1-6}$alkyl, heteroaryl$C_{1-6}$alkyl, hydroxy$C_{1-6}$alkyl, polyhalo$C_{1-6}$alkyl preferably perhalo$C_{1-6}$alkyl, $C_{1-6}$alkyloxy, aryl$C_{1-6}$alkyloxy, heteroaryl$C_{1-6}$alkyloxy, $C_{1-6}$alkylthio, arylthio preferably phenylthio, $C_{1-6}$alkylcarbonyl, hydroxy$C_{1-6}$alkylcarbonyl, $C_{1-6}$alkyloxycarbonyl, $C_{1-6}$alkylcarbonyloxy, $C_{1-6}$alkylcarbonylamino, morpholinyl, piperidinyl, pyrrolidinyl and piperazinyl;

$R^3$ is hydrogen or $C_{1-6}$alkyl;

-D- is —O—, —CHR$^{20}$—, or —NR$^{20}$—, wherein $R^{20}$ is selected from hydrogen and $C_{1-6}$alkyl;

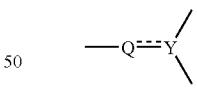

is —CR$^{19}$═C< wherein $R^{19}$ is hydrogen or $C_{1-6}$alkyl;

$R^4$ and $R^5$ are each independently hydrogen, halo, $C_{1-6}$alkyl, polyhalo$C_{1-6}$alkyl, cyano, cyano$C_{1-6}$alkyl, hydroxy, amino, or $C_{1-6}$alkyloxy;

Z is a radical selected from (a-1), (a-2), (a-3), (a-4) and (a-5);

$R^{11}$ or $R^{12}$ are each independently selected from hydrogen, hydroxy, amino, $C_{1-6}$alkyl, nitro, polyhalo$C_{1-6}$alkyl, cyano, aryl, aryl$C_{1-6}$alkyl, aryl(hydroxy)$C_{1-6}$alkyl, arylcarbonyl, $C_{1-6}$alkyloxy, $C_{1-6}$alkyloxy$C_{1-6}$alkyl, $C_{1-6}$alkyloxycarbonyl, aminocarbonyl, hydroxyl-$C_{1-6}$alkyl, amino$C_{1-6}$alkyl, hydroxycarbonyl and —(CH$_2$)$_v$, —(C(═O))$_r$—(CH$_2$)$_u$—NR$^{14}$R$^{15}$;

v is 0 or 1;

r is 0 or 1;

u is 0;

$R^{14}$ and $R^{15}$ are each independently selected from hydrogen, $C_{1-6}$alkyl, —$(CH_2)_k$—$NR^{16}R^{17}$ and $C_{1-12}$alkyl substituted with hydroxy; or $R^{14}$ and $R^{15}$ together with the nitrogen to which they are attached form pyrrolidinyl;

k is 2;

$R^{16}$ and $R^{17}$ are each independently $C_{1-6}$alkyl;

$R^{13}$ is hydrogen or $C_{1-6}$alkyl;

X is $NR^6$, S or N; preferably X is $NR^6$;

aryl is phenyl or phenyl substituted with halo; and heteroaryl is pyridinyl, indolyl, oxadiazolyl or tetrazolyl; and each pyridinyl, indolyl, oxadiazolyl or tetrazolyl can optionally be substituted with one substituent selected from $C_{1-6}$alkyl, aryl and aryl$C_{1-6}$alkyl.

A seventh group of interesting compounds (herein referred to as group "G7") consists of those compounds of formula (I) or any subgroup thereof, wherein:

n is 2;

each $R^1$ is hydrogen;

s is 0;

t is 0;

$R^2$ is selected from hydrogen halo, cyano, $C_{1-6}$alkyl, hydroxy$C_{1-6}$alkyl, polyhalo$C_{1-6}$alkyl preferably perhalo$C_{1-6}$alkyl, $C_{1-6}$alkyloxy, $C_{1-6}$alkylcarbonylamino and morpholinyl; more preferably $R^2$ is selected from hydrogen, halo, $C_{1-6}$alkyl, polyhalo$C_{1-6}$alkyl preferably perhalo$C_{1-6}$alkyl, and $C_{1-6}$alkyloxy;

$R^3$ is hydrogen;

-D- is —O—, —$CHR^{20}$—, or —$NR^{20}$—, wherein $R^{20}$ is selected from hydrogen and $C_{1-6}$alkyl;

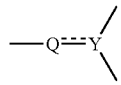

is —CH=C<;

$R^4$ and $R^5$ are each independently hydrogen, $C_{1-6}$alkyl or $C_{1-6}$alkyloxy;

$R^6$ is hydrogen;

Z is a radical selected from (a-1), (a-2) and (a-4), preferably Z is (a-2) or (a-4), even more preferably Z is (a-4); and $R^{11}$ or $R^{12}$ are each independently selected from hydrogen, hydroxy and hydroxy$C_{1-6}$alkyl;

X is $NR^6$, S or N; preferably X is $NR^6$.

Another embodiment consists of compounds of formula (I)

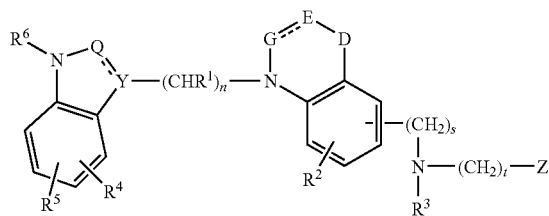

(I)

including any stereochemically isomeric form thereof, wherein n is 0, 1, 2, 3 or 4 and when n is 0 then a direct bond is intended, and wherein $R^1$ on each carbon of the —$(CHR^1)_n$— group is each independently selected from hydrogen, halo, hydroxy, amino, mono- or di($C_{1-6}$alkyl)amino, $C_{1-6}$alkyl, aryl, heteroaryl, $C_{3-7}$cycloalkyl, aryl$C_{1-6}$alkyl, heteroaryl$C_{1-6}$ alkyl, and $C_{3-7}$cycloalkyl-$C_{1-6}$alkyl, any of said mono- or di($C_{1-6}$alkyl)amino, $C_{1-6}$alkyl, heteroaryl, $C_{3-7}$cycloalkyl, aryl$C_{1-6}$alkyl, heteroaryl$C_{1-6}$alkyl or $C_{3-7}$cycloalkyl$C_{1-6}$alkyl being optionally and independently substituted with one or more, preferably one or two, substituents selected from hydroxy, amino, aryl and heteroaryl;

s is 0 or 1 and when s is 0 then a direct bond is intended;

t is 0 or 1 and when t is 0 then a direct bond is intended;

$R^2$ is selected from hydrogen, halo, cyano, amino;

polyhalo$C_{1-6}$alkyl;

$C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;

$R^3$ is hydrogen; $C_{1-6}$alkyl; aryl; heteroaryl; $C_{3-7}$cycloalkyl; $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;

is —$CR^7$=$CR^8$— and then the dotted line is a bond, —$CR^7R^9$—$CR^8R^{10}$—, —C(=O)—$CR^8R^{10}$— or —$CR^7R^9$—C(=O)—, wherein $R^7$, $R^8$, $R^9$ or $R^{10}$ are each independently selected from:

hydrogen, halo, hydroxy, cyano;

polyhalo$C_{1-6}$alkyl;

$C_{1-6}$alkyl, $C_{3-7}$cycloalkyl, $C_{2-6}$alkenyl, aryl, heteroaryl, aryl$C_{1-6}$alkyl, heteroaryl$C_{1-6}$alkyl, $C_{3-7}$cycloalkyl$C_{1-6}$ alkyl, morpholinyl, piperidinyl, pyrrolidinyl, piperazinyl, $C_{1-6}$alkyloxy, $C_{3-7}$cycloalkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, preferably one or two, substituents selected from halo, hydroxy, cyano, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;

or wherein any of $R^7$ and $R^9$ together, or $R^8$ and $R^{10}$ together form a bivalent radical selected from —(CH$_2$)$_2$—O—(CH$_2$)$_2$— and —(CH$_2$)$_2$—NR$^{21}$—(CH$_2$)$_2$— wherein $R^{21}$ is hydrogen, $C_{1-6}$alkyl or $C_{1-6}$alkyloxyalkyl;

or wherein any of $R^7$ and $R^9$ together, or $R^8$ and $R^{10}$ together form a bivalent radical —(CH$_2$)$_m$—, wherein m is 2, 3, 4, 5 or 6;

-D- is —O— or —NR$^{20}$—, wherein $R^{20}$ is selected from hydrogen, $C_{1-6}$alkyl, $C_{1-6}$alkylcarbonyl and $C_{1-6}$alkyloxycarbonyl;

$$-Q\stackrel{\cdots}{=}Y\diagup$$

is —CR$^{19}$=C< and then the dotted line is a bond, —C(=O)—CH<, —C(=O)—N<, —CHR$^{19}$—CH<, or —CHR$^{19}$—N<, wherein each $R^{19}$ is independently hydrogen or $C_{1-6}$alkyl;

$R^4$ and $R^5$ are each independently hydrogen, halo, $C_{1-6}$alkyl, polyhalo$C_{1-6}$alkyl, cyano, cyano$C_{1-6}$alkyl, hydroxy, amino, or $C_{1-6}$alkyloxy, or $R^4$ and $R^5$ together form a bivalent radical selected from methylenedioxy or ethylenedioxy;

$R^6$ is hydrogen, $C_{1-6}$alkyl, $C_{1-6}$alkylcarbonyl or $C_{1-6}$alkyloxycarbonyl;

Z is a radical selected from (a-1)

(a-2)

(a-3)

(a-4)

(a-5)

(a-6)

(a-7)

(a-8)

(a-9)

wherein $R^{11}$ or $R^{12}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo-$C_{1-6}$alkyl, aryl, heteroaryl, aryl$C_{1-6}$alkyl, heteroaryl$C_{1-6}$alkyl, aryl(hydroxy)-$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —(CH$_2$)$_v$—(C(=O))$_r$—(CHR$^{18}$)$_u$—NR$^{14}$R$^{15}$, wherein v is 0, 1, 2, 3, 4, 5, or 6 and when v is 0 then a direct bond is intended;

r is 0 or 1 and when r is 0 then a direct bond is intended;

u is 0, 1, 2, 3, 4, 5, or 6 and when u is 0 then a direct bond is intended;

$R^{18}$ is hydrogen or $C_{1-6}$alkyl;

$R^{14}$ and $R^{15}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkyl; $C_{3-7}$cycloalkylcarbonyl; —(CH$_2$)$_k$—NR$^{16}$R$^{17}$; $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl, or $R^{14}$ and $R^{15}$ together with the nitrogen to which they are attached form morpholinyl; piperidinyl; pyrrolidinyl; piperazinyl; or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$alkyl; wherein k is 0, 1, 2, 3, 4, 5, or 6 and when k is 0 then a direct bond is intended;

$R^{16}$ and $R^{17}$ are each independently selected from hydrogen; $C_{1-6}$alkyl; aryl$C_{1-6}$alkyloxycarbonyl; $C_{3-7}$cycloalkyl; $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or $R^{16}$ and $R^{17}$ together with the nitrogen to which they are attached form morpholinyl, piperazinyl, or piperazinyl substituted with $C_{1-6}$alkyloxycarbonyl;

$R^{13}$ is hydrogen; $C_{1-6}$alkyl; $C_{3-7}$cycloalkyl; $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;

aryl is phenyl or naphthalenyl;

each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and each phenyl or naphthalenyl can optionally be substituted with a bivalent radical selected from methylenedioxy and ethylenedioxy; heteroaryl is pyridinyl, indolyl, quinolinyl, imidazolyl, furanyl, thienyl, oxadiazolyl, tetrazolyl, benzofuranyl or tetrahydrofuranyl;

each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;

an N-oxide form thereof, an addition salt thereof or a solvate thereof.

Another embodiment of particularly preferred compounds (herein referred to as group "G8") consists of those compounds of formula (I) wherein t is 0; s is 0; n is 2; X is $NR^6$, S or O, in particular O; $R^1$ is hydrogen; $R^2$ is hydrogen or halo, in particular hydrogen or fluoro; $R^3$ is hydrogen; $R^4$ and $R^5$ are each independently hydrogen, $C_{1-6}$alkyl or $C_{1-6}$alkyloxy; $R^6$ is hydrogen;

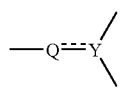

is —$CR^{19}$=C< and then the dotted line is a bond, wherein $R^{19}$ is hydrogen; D is —O—, —$CH_2$— or —$NR^{20}$— wherein $R^{20}$ is hydrogen or $C_{1-6}$alkyl, in particular D is O; Z is a radical of formula (a-2) or (a-4); $R^{11}$ and $R^{12}$ are each independently selected from hydrogen, hydroxyl and hydroxy$C_{1-6}$alkyl.

Another embodiment of particularly preferred compounds (herein referred to as group "G9") consists of those compounds of formula (I) wherein X is $NR^6$.

Another embodiment of particularly preferred compounds (herein referred to as group "G10") consists of those compounds of formula (I) wherein D is O.

Another embodiment of particularly preferred compounds (herein referred to as group "G11") consists of those compounds of formula (I) wherein

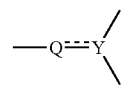

is —$CR^{19}$=C< and then the dotted line is a bond, wherein $R^{19}$ is hydrogen.

Preferably, in compounds of formula (I), and in particular in compounds of any one of the above groups "G1" to "G11" (the recitation "any one of the groups 'G1' to 'G11'" as used throughout this specification encompasses a specific reference to any one or each of the compound groups "G1", "G2", "G3", "G4", "G5", "G6", "G7", "G8", "G9", "G10", or "G11" as defined herein), the substituent —$(CH_2)_s$—$NR^3$—$(CH_2)_t$—Z may be bound on the central phenyl ring in the para (p-) position relative to the position on the central phenyl ring whereto the N atom of the substituent

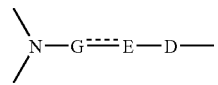

is bound.

In a preferred embodiment, in compounds of formula (I), and in particular in compounds of any one of the above groups "G1" to "G11"

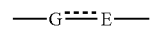

is —$CR^7$=$CR^8$—, $CR^7R^9$—$CR^8R^{10}$—, —C(=O)—$CR^8R^{10}$— or —$CR^7R^9$—C(=O)—, more preferably

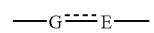

is —$CR^7R^9$—$CR^8R^{10}$— or —C(=O)—$CR^8R^{10}$—, wherein $R^7$, $R^8$, $R^9$ or $R^{10}$ are each independently selected from
hydrogen, halo, hydroxy, cyano;
polyhalo$C_{1-6}$alkyl preferably perhalo$C_{1-6}$alkyl;
$C_{1-6}$alkyl, $C_{3-7}$cycloalkyl, aryl, heteroaryl, aryl$C_{1-6}$alkyl, heteroaryl$C_{1-6}$alkyl, $C_{3-7}$cycloalkyl$C_{1-6}$alkyl, $C_{1-6}$alkyloxy, $C_{3-7}$cycloalkyl$C_{1-6}$alkyloxy, aryl$C_{1-6}$alkyloxy, heteroaryl$C_{1-6}$alkyloxy, hydroxy$C_{1-6}$alkyl, $C_{1-6}$alkylcarbonyl, hydroxyl-$C_{1-6}$alkylcarbonyl, $C_{1-6}$alkyloxycarbonyl, $C_{1-6}$alkylcarbonyloxy, mono- or di($C_{1-6}$alkyl)amino,
$C_{1-6}$alkylcarbonylamino, mono- or di($C_{1-6}$alkyl)aminocarbonyl, morpholinyl, piperidinyl, pyrrolidinyl and piperazinyl, any of said groups optionally substituted with one or more, preferably one or two, substituents selected from halo, hydroxy, cyano, amino, mono- or di($C_{1-6}$ alkyl)amino, $C_{1-6}$alkyl, polyhalo-$C_{1-6}$alkyl, aryl, heteroaryl and $C_{1-6}$alkyloxy;

or wherein any of $R^7$ and $R^9$ together, or $R^8$ and $R^{10}$ together form a bivalent radical —$(CH_2)_m$—, wherein m is 2, 3, 4, 5 or 6;

In another preferred embodiment, in compounds of formula (I), and in particular in compounds of any one of the above groups "G1" to "G11",

—G═E— is —$CR^7$═$CR^8$—, —$CR^7R^9$—$CR^8R^{10}$—, —$C(═O)$—$CR^8R^{10}$— or —$CR^7R^9$—$C(═O)$—, more preferably

—G═E— is —$CR^7R^9$—$CR^8R^{10}$— or —$C(═O)$—$CR^8R^{10}$—, wherein $R^7$, $R^8$, $R^9$ or $R^{10}$ are each independently selected from hydrogen, halo, hydroxy;

perhalo$C_{1-6}$alkyl;

$C_{1-6}$alkyl, $C_{3-7}$cycloalkyl, aryl$C_{1-6}$alkyl, heteroaryl$C_{1-6}$alkyl, $C_{1-6}$alkyloxy, aryl-$C_{1-6}$alkyloxy, heteroaryl$C_{1-6}$alkyloxy, $C_{1-6}$alkylcarbonyl, mono- or di($C_{1-6}$alkyl)amino, $C_{1-6}$alkylcarbonylamino and morpholinyl, any of said groups optionally substituted with one or more, preferably one or two, substituents selected from halo, hydroxy, amino, $C_{1-6}$alkyl, polyhalo$C_{1-6}$alkyl, aryl, heteroaryl and $C_{1-6}$alkyloxy;

or wherein any of $R^7$ and $R^9$ together, or $R^8$ and $R^{10}$ together form a bivalent radical —$(CH_2)_m$—, wherein m is 2, 3, 4, 5 or 6;

In a further preferred embodiment, in compounds of formula (I), and in particular in compounds of any one of the above groups "G1" to "G11",

—G═E— is —$CR^7$═$CR^8$—, —$CR^7R^9$—$CR^8R^{10}$—, —$C(═O)$—$CR^8R^{10}$— or —$CR^7R^9$—$C(═O)$—, more preferably

—G═E— is —$CR^7R^9$—$CR^8R^{10}$— or —$C(═O)$—$CR^8R^{10}$—, wherein $R^7$, $R^8$, $R^9$ or $R^{10}$ are each independently selected from hydrogen, halo, $C_{1-6}$alkyl, $C_{3-7}$cycloalkyl, halo$C_{1-6}$alkyl, perhalo$C_{1-6}$alkyl, hydroxy$C_{1-6}$alkyl, $C_{1-6}$alkyloxy, mono- or di($C_{1-6}$ alkyl)amino, $C_{1-6}$alkylcarbonylamino and morpholinyl, or wherein any of $R^7$ and $R^9$ together, or $R^8$ and $R^{10}$ together form a bivalent radical —$(CH_2)_m$— wherein m is 2, 3, 4, 5 or 6.

In a further preferred embodiment, in compounds of formula (I), and in particular in compounds of any one of the above groups "G1" to "G11",

—G═E— is —$CR^7$═$CR^8$—, —$CR^7R^9$—$CR^8R^{10}$—, —$C(═O)$—$CR^8R^{10}$— or —$CR^7R^9$—$C(═O)$—, more preferably

—G═E— is —$CR^7R^9$—$CR^8R^{10}$— or —$C(═O)$—$CR^8R^{10}$—, wherein $R^7$, $R^8$, $R^9$ or $R^{10}$ are each independently selected from hydrogen, halo, $C_{1-6}$alkyl, perhalo$C_{1-6}$alkyl, or wherein any of $R^7$ and $R^9$ together, or $R^8$ and $R^{10}$ together form a bivalent radical —$(CH_2)_m$— wherein m is 2, 3, 4, 5 or 6;

In a further preferred embodiment, in compounds of formula (I), and in particular in compounds of any one of the above groups "G1" to "G11",

—G═E— is —$CR^7$═$CR^8$—, —$CR^7R^9$—$CR^8R^{10}$—, —$C(═O)$—$CR^8R^{10}$— or —$CR^7R^9$—$C(═O)$—, more preferably

—G═E— is —$CR^7R^9$—$CR^8R^{10}$— or —$C(═O)$—$CR^8R^{10}$—, wherein $R^7$, $R^8$, $R^9$ or $R^{10}$ are each hydrogen.

In a preferred embodiment, in compounds of formula (I), and in particular in compounds of any one of the above groups "G1" to "G11",

—G═E— is —$CR^7CR^9$—, $CR^8R^{10}$—, wherein $R^7$, $R^8$, $R^9$ and $R^{10}$ are as defined above.

In another preferred embodiment, in compounds of formula (I), and in particular in compounds of any one of the above groups "G1" to "G11",

—G═E— is —$C(═O)$—$CR^8R^{10}$— or —$CR^7R^9$—$C(═O)$—, more preferably

—G═E— is —$C(═O)$—$CR^8R^{10}$, wherein $R^7$, $R^8$, $R^9$ and $R^{10}$ are as defined above.

In another preferred embodiment, in compounds of formula (I), and in particular in compounds of any one of the above groups "G1" to "G11",

—G═E— is —CH$_2$—CH$_2$—; —CH$_2$—CH(CH$_3$)—; —CH$_2$—C(CH$_3$)$_2$—; —CH$_2$—CH(CH$_2$OH)—; —CH$_2$—C(CH$_3$)(CH$_2$CH$_3$)—; —C(═O)—CH$_2$—; —C(═O)—CH(CH$_3$)—; —C(═O)—C(CH$_3$)$_2$—; —C(═O)—CF$_2$—;

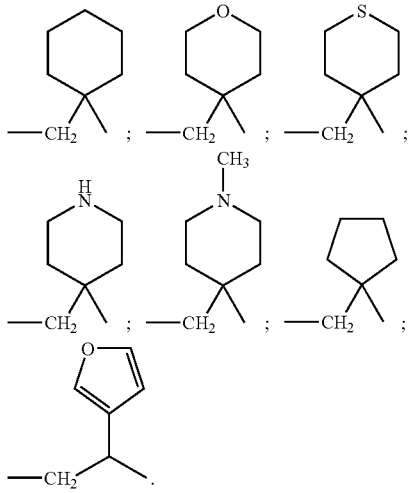

Further, in some embodiments, when

—G═E— is —CR$^7$R$^9$—CR$^8$R$^{10}$—, either one of the following restrictions may preferably apply:
a) when any one or both of R$^7$ and R$^9$ is different from hydrogen, then at least one and preferably both of R$^8$ and R$^{10}$ are hydrogen; or
b) when any one or both of R$^8$ and R$^{10}$ is different from hydrogen, then at least one and preferably both of R$^7$ and R$^9$ are hydrogen; or
c) when two substituents of R$^7$, R$^8$, R$^9$ and R$^{10}$ are different from hydrogen, then R$^7$ or R$^9$ is one of said two substituents, and R$^8$ or R$^{10}$ is the other one of said two substituents; or
d) preferably, when one or two substituents of R$^7$, R$^8$, R$^9$ and R$^{10}$ are different from hydrogen, then said one or two substituents are selected from R$^8$ and R$^{10}$.

Further, in some embodiments, when

—G═E— is —CR$^7$═CR$^8$—, either one of the following restrictions may preferably apply:
a) when R$^7$ is different from hydrogen, then R$^8$ is hydrogen; or
b) when R$^8$ is different from hydrogen, then R$^7$ is hydrogen.

In a further embodiment, when

—G═E— is —C(═)—CR$^8$R$^{10}$, at least one of R$^8$ and R$^{10}$ is hydrogen.
In a further embodiment, when

—G═E— is —CR$^7$R$^9$—C(═O)—, at least one of R$^7$ and R$^9$ is hydrogen.

Table 1 lists several non-limiting examples of

—G═E— groups suitable herein:

| Ex. | G | E | R$^7$ | R$^9$ | R$^8$ | R$^{10}$ |
|---|---|---|---|---|---|---|
| 1 | —CR$^7$R$^9$— | CR$^8$R$^{10}$— | —H | —H | —H | —H |
| 2 | —CR$^7$R$^9$— | CR$^8$R$^{10}$— | —H | —H | —CH$_3$ | —H |
| 3 | —CR$^7$R$^9$— | CR$^8$R$^{10}$— | —H | —H | —CH$_3$ | —CH$_3$ |
| 4 | —CR$^7$R$^9$— | CR$^8$R$^{10}$— | —H | —H | —CH$_2$CH$_3$ | —H |
| 5 | —CR$^7$R$^9$— | CR$^8$R$^{10}$— | —H | —H | —CH$_2$CH$_3$ | —CH$_3$ |
| 6 | —CR$^7$R$^9$— | CR$^8$R$^{10}$— | —H | —H | —CH$_2$CH$_3$ | —CH$_2$CH$_3$ |
| 7 | —CR$^7$R$^9$— | CR$^8$R$^{10}$— | —CH$_3$ | —H | —H | —H |
| 8 | —CR$^7$R$^9$— | CR$^8$R$^{10}$— | —CH$_2$CH$_3$ | —H | —H | —H |
| 9 | —CR$^7$R$^9$— | CR$^8$R$^{10}$— | —H | —H | —CF$_3$ | —H |
| 10 | —CR$^7$R$^9$— | CR$^8$R$^{10}$— | —H | —H | —CF$_3$ | —CF$_3$ |
| 11 | —CR$^7$R$^9$— | CR$^8$R$^{10}$— | —CF$_3$ | —H | —H | —H |
| 12 | —CR$^7$R$^9$— | CR$^8$R$^{10}$— | —CF$_3$ | —CF$_3$ | —H | —H |
| 13 | —CR$^7$R$^9$— | CR$^8$R$^{10}$— | —H | —H | —F | —H |
| 14 | —CR$^7$R$^9$— | CR$^8$R$^{10}$— | —H | —H | —F | —F |
| 15 | —CR$^7$R$^9$— | CR$^8$R$^{10}$— | —H | —H | —Cl | —H |
| 16 | —CR$^7$R$^9$— | CR$^8$R$^{10}$— | —H | —H | —Cl | —Cl |
| 17 | —CR$^7$R$^9$— | CR$^8$R$^{10}$— | —F | —H | —H | —H |
| 18 | —CR$^7$R$^9$— | CR$^8$R$^{10}$— | —Cl | —H | —H | —H |
| 19 | —CR$^7$R$^9$— | CR$^8$R$^{10}$— | —H | —H | —CH$_2$OH | —H |
| 20 | —CR$^7$R$^9$— | CR$^8$R$^{10}$— | —H | —H | —CH$_2$OH | —CH$_3$ |
| 21 | —CR$^7$R$^9$— | CR$^8$R$^{10}$— | —H | —H | —CH$_2$OH | —CH$_2$OH |
| 22 | —CR$^7$R$^9$— | CR$^8$R$^{10}$— | —CH$_2$OH | —H | —H | —H |
| 23 | —CR$^7$R$^9$— | CR$^8$R$^{10}$— | —H | —H | —OCH$_3$ | —H |
| 24 | —CR$^7$R$^9$— | CR$^8$R$^{10}$— | —H | —H | —OCH$_3$ | —CH$_3$ |
| 25 | —CR$^7$R$^9$— | CR$^8$R$^{10}$— | —H | —H | —OCH$_3$ | —OCH$_3$ |
| 26 | —CR$^7$R$^9$— | CR$^8$R$^{10}$— | —OCH$_3$ | —H | —H | —H |

-continued

| Ex. | G | E | R⁷ | R⁹ | R⁸ | R¹⁰ |
|---|---|---|---|---|---|---|
| 27 | —CR⁷R⁹— | —CR⁸R¹⁰— | —H | —H | —N(morpholine)— | —H |
| 28 | —CR⁷R⁹— | —CR⁸R¹⁰— | —N(morpholine)— | —H | —H | —H |
| 29 | —CR⁷R⁹— | —CR⁸R¹⁰— | —H | —H | R⁸ and R¹⁰ together form: —(CH₂)ₘ—, wherein m is 2, 3, 4, 5 or 6 | |
| 30 | —CR⁷R⁹— | —CR⁸R¹⁰— | R⁷ and R⁹ together form: —(CH₂)ₘ—, wherein m is 2, 3, 4, 5 or 6 | | —H | —H |
| 31 | —C(=O)— | —CR⁸R¹⁰— | | | —H | —H |
| 32 | —C(=O)— | —CR⁸R¹⁰— | | | —CH₃ | —H |
| 33 | —C(=O)— | —CR⁸R¹⁰— | | | —CH₃ | —CH₃ |
| 34 | —C(=O)— | —CR⁸R¹⁰— | | | —CH₂CH₃ | —H |
| 35 | —C(=O)— | —CR⁸R¹⁰— | | | —CH₂CH₃ | —CH₃ |
| 36 | —C(=O)— | —CR⁸R¹⁰— | | | —CH₂CH₃ | —CH₂CH₃ |
| 37 | —C(=O)— | —CR⁸R¹⁰— | | | —CF₃ | —H |
| 38 | —C(=O)— | —CR⁸R¹⁰— | | | —CF₃ | —CF₃ |
| 39 | —C(=O)— | —CR⁸R¹⁰— | | | —F | —H |
| 40 | —C(=O)— | —CR⁸R¹⁰— | | | —F | —F |
| 41 | —C(=O)— | —CR⁸R¹⁰— | | | —Cl | —H |
| 42 | —C(=O)— | —CR⁸R¹⁰— | | | —Cl | —Cl |
| 43 | —C(=O)— | —CR⁸R¹⁰— | | | —CH₂OH | —H |
| 44 | —C(=O)— | —CR⁸R¹⁰— | | | —CH₂OH | —CH₃ |
| 45 | —C(=O)— | —CR⁸R¹⁰— | | | —CH₂OH | —CH₂OH |
| 46 | —C(=O)— | —CR⁸R¹⁰— | | | —OCH₃ | —H |
| 47 | —C(=O)— | —CR⁸R¹⁰— | | | —OCH₃ | —CH₃ |
| 48 | —C(=O)— | —CR⁸R¹⁰— | | | —OCH₃ | —OCH₃ |
| 49 | —C(=O)— | —CR⁸R¹⁰— | | | —N(morpholine)— | —H |
| 50 | —C(=O)— | —CR⁸R¹⁰— | | | R⁸ and R¹⁰ together form: —(CH₂)ₘ—, wherein m is 2, 3, 4, 5 or 6 | |
| 51 | —CR⁷R⁹— | —C(=O)— | —H | —H | | |
| 52 | —CR⁷R⁹— | —C(=O)— | —CH₃ | —H | | |
| 53 | —CR⁷R⁹— | —C(=O)— | —CH₃ | —CH₃ | | |
| 54 | —CR⁷R⁹— | —C(=O)— | —CH₂CH₃ | —H | | |
| 55 | —CR⁷R⁹— | —C(=O)— | —CH₂CH₃ | —CH₃ | | |
| 56 | —CR⁷R⁹— | —C(=O)— | —CH₂CH₃ | —CH₂CH₃ | | |
| 57 | —CR⁷R⁹— | —C(=O)— | —CF₃ | —H | | |
| 58 | —CR⁷R⁹— | —C(=O)— | —CF₃ | —CF₃ | | |
| 59 | —CR⁷R⁹— | —C(=O)— | —F | —H | | |
| 60 | —CR⁷R⁹— | —C(=O)— | —F | —F | | |
| 61 | —CR⁷R⁹— | —C(=O)— | —Cl | —H | | |
| 62 | —CR⁷R⁹— | —C(=O)— | —Cl | —F | | |
| 63 | —CR⁷R⁹— | —C(=O)— | —Cl | —Cl | | |
| 64 | —CR⁷R⁹— | —C(=O)— | —CH₂OH | —H | | |
| 65 | —CR⁷R⁹— | —C(=O)— | —CH₂OH | —CH₃ | | |
| 66 | —CR⁷R⁹— | —C(=O)— | —CH₂OH | —CH₂OH | | |
| 67 | —CR⁷R⁹— | —C(=O)— | —OCH₃ | —H | | |
| 68 | —CR⁷R⁹— | —C(=O)— | —OCH₃ | —CH₃ | | |
| 69 | —CR⁷R⁹— | —C(=O)— | —OCH₃ | —OCH₃ | | |
| 70 | —CR⁷R⁹— | —C(=O)— | —NC(=O)CH₃ | —H | | |
| 71 | —CR⁷R⁹— | —C(=O)— | —NC(=O)CH₃ | —CH₃ | | |
| 72 | —CR⁷R⁹— | —C(=O)— | —N(morpholine)— | —H | | |
| 73 | —CR⁷R⁹— | —C(=O)— | R⁷ and R⁹ together form: —(CH₂)ₘ—, wherein m is 2, 3, 4, 5 or 6 | | | |

With any one option listed in Table 1, -D- may be —O—, —CHR$^{20}$—, or —NR$^{20}$— wherein R$^{20}$ is selected from hydrogen, C$_{1-6}$alkyl, C$_{1-6}$alkylcarbonyl and C$_{1-6}$alkyloxycarbonyl, preferably R$^{20}$ is selected from hydrogen and C$_{1-6}$alkyl, more preferably R$^{20}$ is hydrogen; and even more preferably -D- is —O—.

Thus, exemplary preferred groups of compounds consists of those compounds of formula (I) or any subgroup thereof, wherein:

n is 2; each R$^1$ is hydrogen; s is 0; t is 0; R$^2$ is selected from hydrogen, halo, cyano, C$_{1-6}$alkyl, hydroxyC$_{1-6}$alkyl, polyhaloC$_{1-6}$alkyl preferably perhaloC$_{1-6}$alkyl, C$_{1-6}$alkyloxy, C$_{1-6}$alkylcarbonylamino and morpholinyl; R$^3$ is hydrogen; -D- is —O— or —NR$^{20}$— wherein R$^{20}$ is hydrogen or C$_{1-6}$alkyl;

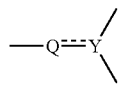

is —CR$^{19}$═C< wherein R$^{19}$ is hydrogen or C$_{1-6}$alkyl; R$^4$ and R$^5$ are each independently hydrogen, C$_{1-6}$alkyl or C$_{1-6}$alkyloxy; R$^6$ is hydrogen; Z is a radical selected from (a-1), (a-2), (a-3), (a-4) and (a-5); R$^{11}$ or R$^{12}$ are each independently selected from hydrogen, hydroxy and hydroxyC$_{1-6}$alkyl; R$^{13}$ is hydrogen; and

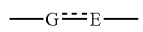

is —CR$^7$═CR$^8$—, —CR$^7$R$^9$—CR$^8$R$^{10}$—, —C(═O)—CR$^8$R$^{10}$— or —CR$^7$R$^9$—C(═O)—, more preferably

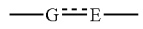

is —CR$^7$R$^9$—CR$^8$R$^{10}$— or —C(═O)—CR$^8$R$^{10}$—, wherein R$^7$, R$^8$, R$^9$ or R$^{10}$ are each independently selected from
  hydrogen, halo, hydroxy, cyano;
  polyhaloC$_{1-6}$alkyl preferably perhaloC$_{1-6}$alkyl;
  C$_{1-6}$alkyl, C$_{3-7}$cycloalkyl, aryl, heteroaryl, arylC$_{1-6}$alkyl, heteroarylC$_{1-6}$alkyl, C$_{3-7}$cycloalkylC$_{1-6}$alkyl, C$_{1-6}$alkyloxy, C$_{3-7}$cycloalkylC$_{1-6}$alkyloxy, arylC$_{1-6}$alkyloxy, heteroarylC$_{1-6}$alkyloxy, hydroxyC$_{1-6}$alkyl, C$_{1-6}$alkylcarbonyl, hydroxyC$_{1-6}$alkylcarbonyl, C$_{1-6}$alkyloxycarbonyl, C$_{1-6}$alkylcarbonyloxy, mono- or di(C$_{1-6}$alkyl)amino,
  C$_{1-6}$alkylcarbonylamino, mono- or di(C$_{1-6}$alkyl)aminocarbonyl, morpholinyl, piperidinyl, pyrrolidinyl and piperazinyl, any of said groups optionally substituted with one or more, preferably one or two, substituents selected from halo, hydroxy, cyano, amino, mono- or di(C$_{1-6}$alkyl)amino, C$_{1-6}$alkyl, polyhalo-C$_{1-6}$alkyl, aryl, heteroaryl and C$_{1-6}$alkyloxy;
  or wherein any of R$^7$ and R$^9$ together, or R$^8$ and R$^{10}$ together form a bivalent radical —(CH$_2$)$_m$—, wherein m is 2, 3, 4, 5 or 6;
more preferably wherein R$^7$, R$^8$, R$^9$ or R$^{10}$ are each independently selected from
  hydrogen, halo, hydroxy;
  perhaloC$_{1-6}$alkyl;
  C$_{1-6}$alkyl, C$_{3-7}$cycloalkyl, arylC$_{1-6}$alkyl, heteroarylC$_{1-6}$alkyl, C$_{1-6}$alkyloxy, aryl-C$_{1-6}$alkyloxy, heteroarylC$_{1-6}$alkyloxy, C$_{1-6}$alkylcarbonyl, mono- or di(C$_{1-6}$alkyl)amino,
  C$_{1-6}$alkylcarbonylamino and morpholinyl, any of said groups optionally substituted with one or more, preferably one or two, substituents selected from halo, hydroxy, amino, C$_{1-6}$alkyl, polyhaloC$_{1-6}$alkyl, aryl, heteroaryl and C$_{1-6}$alkyloxy;
  or wherein any of R$^7$ and R$^9$ together, or R$^8$ and R$^{10}$ together form a bivalent radical —(CH$_2$)$_m$—, wherein m is 2, 3, 4, 5 or 6.

Further exemplary preferred groups of compounds consists of those compounds of formula (I) or any subgroup thereof, wherein:

n is 2; each R$^1$ is hydrogen; s is 0; t is 0; R$^2$ is selected from hydrogen, halo, C$_{1-6}$alkyl, polyhaloC$_{1-6}$alkyl preferably perhaloC$_{1-6}$alkyl, and C$_{1-6}$alkyloxy; R$^3$ is hydrogen; -D- is —O— or —NH—, preferably -D- is —O—;

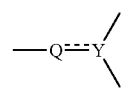

is —CH═C<; R$^4$ and R$^5$ are each independently hydrogen, C$_{1-6}$alkyl or C$_{1-6}$alkyloxy; R$^6$ is hydrogen; Z is a radical selected from (a-1), (a-2) and (a-4), preferably Z is (a-2) or (a-4), even more preferably Z is (a-4); R$^{11}$ or R$^{12}$ are each independently selected from hydrogen, hydroxy and hydroxyC$_{1-6}$alkyl; and

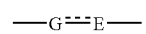

is —CR$^7$═CR$^8$—, —CR$^7$R$^9$—CR$^8$R$^{10}$—, —C(═O)—CR$^8$R$^{10}$— or —CR$^7$R$^9$—C(═O)—, more preferably

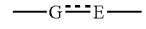

is —CR$^7$R$^9$—CR$^8$R$^{10}$— or —C(═O)—CR$^8$R$^{10}$—, wherein R$^7$, R$^8$, R$^9$ or R$^{10}$ are each independently selected from hydrogen, halo, C$_{1-6}$alkyl, C$_{3-7}$cycloalkyl, haloC$_{1-6}$alkyl, perhaloC$_{1-6}$alkyl, hydroxyC$_{1-6}$alkyl, C$_{1-6}$alkyloxy, mono- or di(C$_{1-6}$alkyl)amino, C$_{1-6}$alkylcarbonylamino and morpholinyl, or wherein any of R$^7$ and R$^9$ together, or R$^8$ and R$^{10}$ together form a bivalent radical —(CH$_2$)$_m$— wherein m is 2, 3, 4, 5 or 6;

more preferably wherein R$^7$, R$^8$, R$^9$ or R$^{10}$ are each independently selected from hydrogen, halo, C$_{1-6}$alkyl, perhaloC$_{1-6}$alkyl, or wherein any of R$^7$ and R$^9$ together, or R$^8$ and R$^{10}$ together form a bivalent radical —(CH$_2$)$_m$—, wherein m is 2, 3, 4, 5 or 6;

also preferably wherein each R$^7$, R$^8$, R$^9$ or R$^{10}$ is hydrogen.

Table 2 lists preferred albeit non-limiting examples of compounds of formula (I) that were prepared in the present invention.

TABLE 2
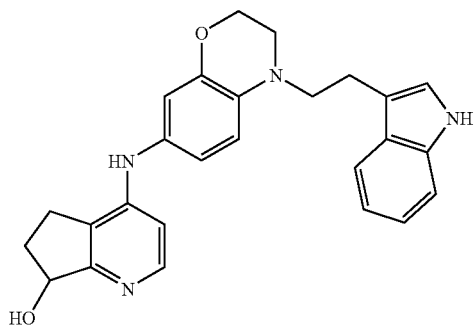
Comp. No. 1
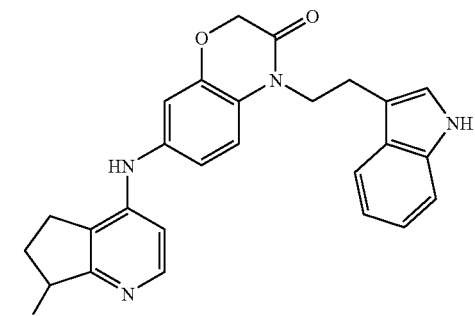
Comp. No. 2
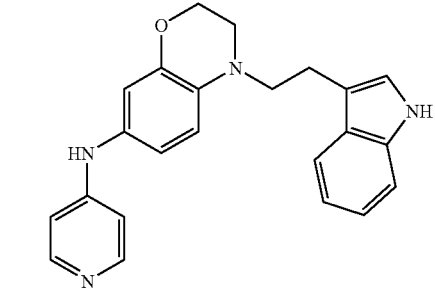
Comp. No. 3
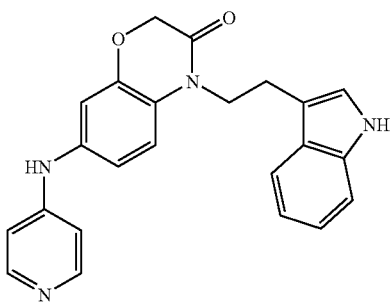
Comp. No. 4
Particularly preferred are compounds No. 1 and 2, more preferably compound No. 1, which may achieve especially pronounced desired biological effects.
Further preferred compounds are compounds No. 22, 13, 25, 34, 27, 5, 12, 11, which may achieve especially pronounced desired biological effects. Thus, preferred compounds are selected from:
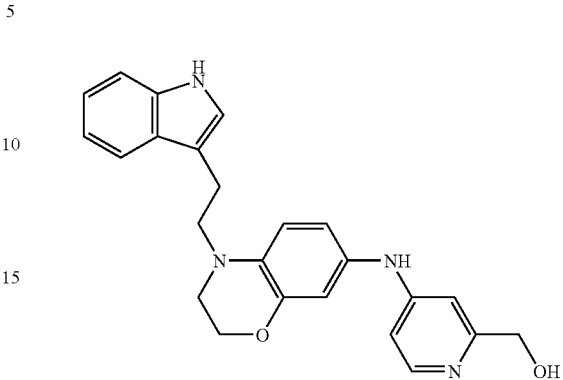
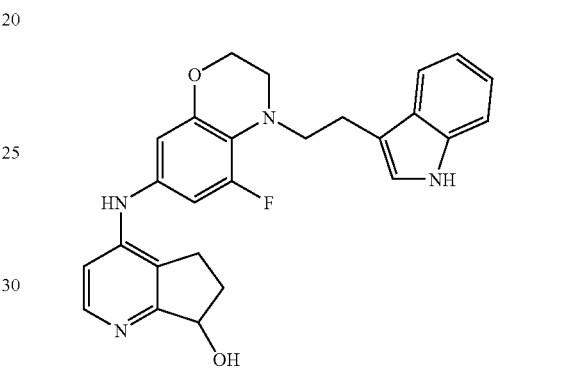
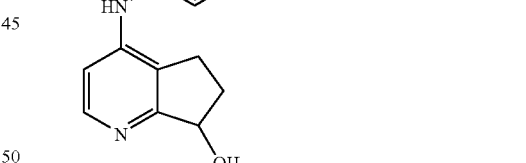
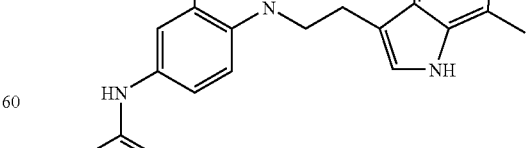

-continued

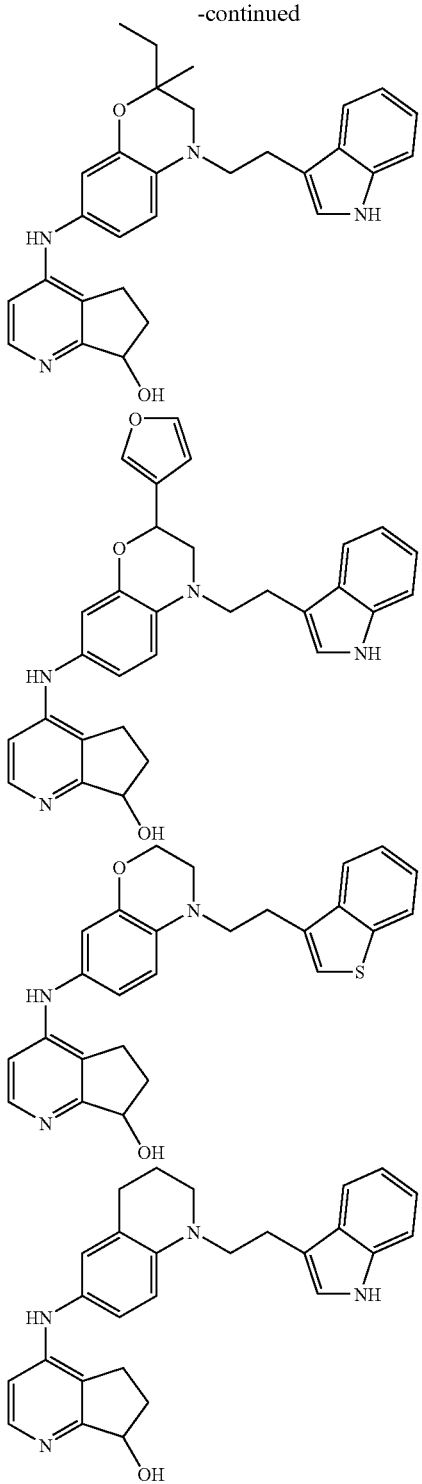

including any stereochemically isomeric form thereof;
an N-oxide form thereof, an addition salt thereof or a solvate thereof.

The compounds of formula (I), their N-oxides, pharmaceutically acceptable salts, solvates, and stereochemically isomeric forms thereof may be prepared in conventional manner. The starting materials and some of the intermediates are known compounds and are commercially available or may be prepared according to conventional reaction procedures as generally known in the art.

A number of such preparation methods will be described hereinafter in more detail. Other methods for obtaining final compounds of formula (I) are described in the examples.

The compounds of formula (I) can be prepared by reacting an intermediate of formula (II) with an intermediate of formula (III) or an appropriate acid addition salt thereof, wherein W is an appropriate leaving group such as, for example, halo, e.g., fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g., methanol, ethanol, 2-methoxy-ethanol, propanol, butanol and the like; an ether, e.g., 1,4-dioxane optionally in mixture with hydrochloric acid, 1,1'-oxybispropane and the like; a ketone, e.g., 4-methyl-2-pentanone; or N,N-dimethylformamide, nitrobenzene, acetonitrile, acetic acid and the like. The addition of an appropriate base such as, for example, an alkali or earth alkaline metal carbonate or organic base, e.g., triethylamine, N,N-diisopropylethanamine or sodium carbonate, may be utilized to neutralise the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

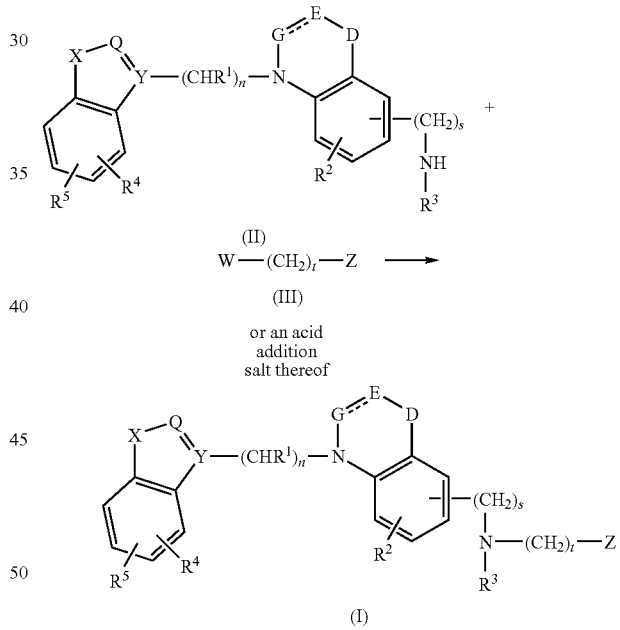

The above reaction can also be used to prepare compounds of formula (I) wherein

—G≡E— is —$CR^7R^9$—$CR^8R^{10}$—, wherein $R^8$ and $R^{10}$ together form a bivalent radical —$(CH_2)_2$—$NR^{21}$—$(CH_2)_2$— wherein $R^{21}$ represents hydrogen and $R^7$ and $R^9$ represent hydrogen, herein referred to as compounds of formula (I-d), starting from the corresponding intermediate of formula (XIX) wherein P represents a suitable protective group, e.g. $C_{1-6}$alkyloxycarbonyl

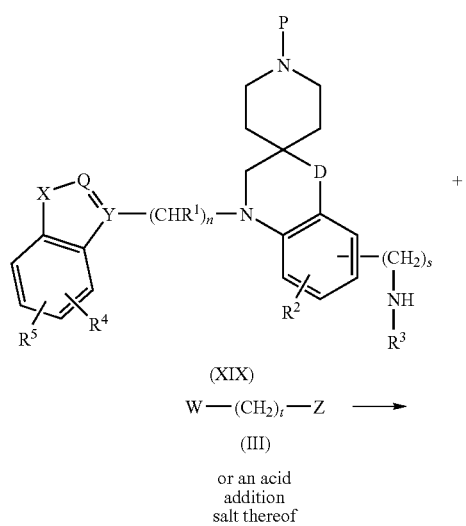

(XIX)

W—(CH$_2$)$_t$—Z (III)

or an acid
addition
salt thereof

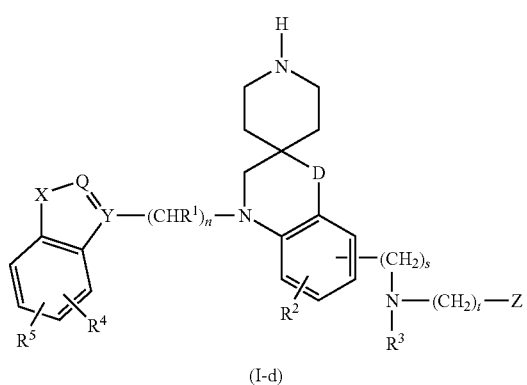

(I-d)

The above reaction can also be used to prepare compounds of formula (I) wherein

—G≡E— is —CR$^7$R$^9$—CR$^8$R$^{10}$—, herein R$^8$ represents hydroxyC$_{1-6}$ alkyl and R$^7$, R$^9$ and R$^{10}$ represent hydrogen, herein referred to as compounds of formula (I-e), starting from the corresponding intermediate of formula (XX).

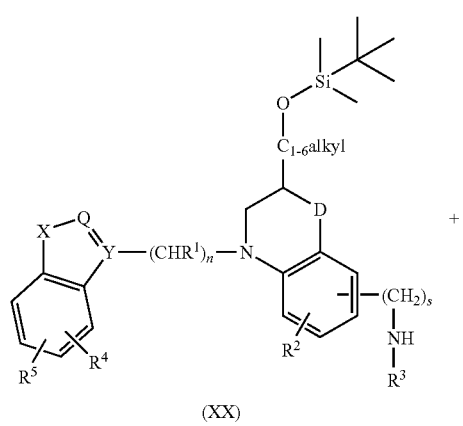

(XX)

+

W—(CH$_2$)$_t$—Z (III)

or an acid
addition
salt thereof

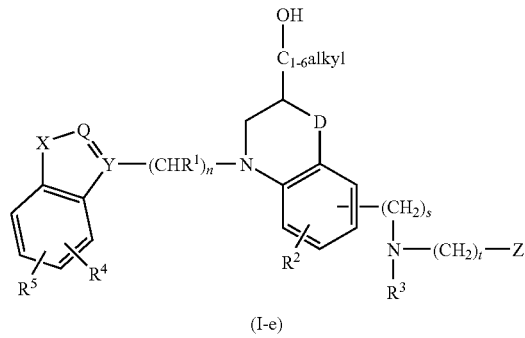

(I-e)

The compounds of formula (I-e) can also be prepared reacting the corresponding intermediate of formula (XXI) with a suitable deprotection agent for the alcohol function, e.g. tetrabutylammonium fluoride, in the presence of a suitable solvent, e.g. tetrahydrofuran.

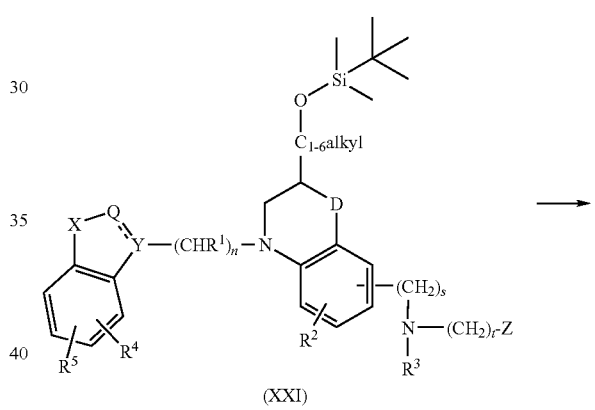

(XXI)

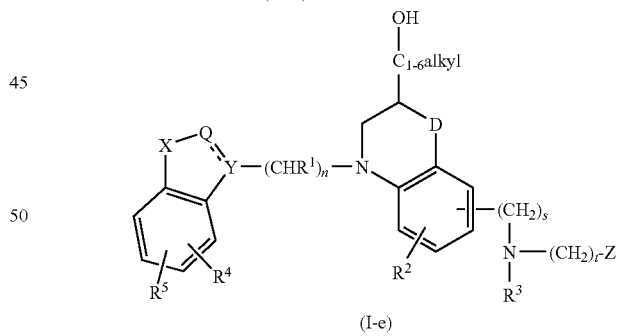

(I-e)

The compounds of formula (I) can be prepared by reacting an intermediate of formula (IV), wherein A is an appropriate leaving group such as, for example, halo, e.g., fluoro, chloro, bromo or iodo, or a sulfonyloxy radical such as methylsulfonyloxy, 4-methylphenylsulfonyloxy and the like, with an intermediate of formula (V). The addition of an appropriate base such as, for example, an alkali or earth alkaline metal carbonate or organic base, e.g., cesium carbonate, may be utilised to neutralise the acid which is liberated during the course of the reaction. The reaction can be performed in a reaction-inert solvent such as, for example, N,N-dimethylformamide, tetrahydrofuran, and the like.

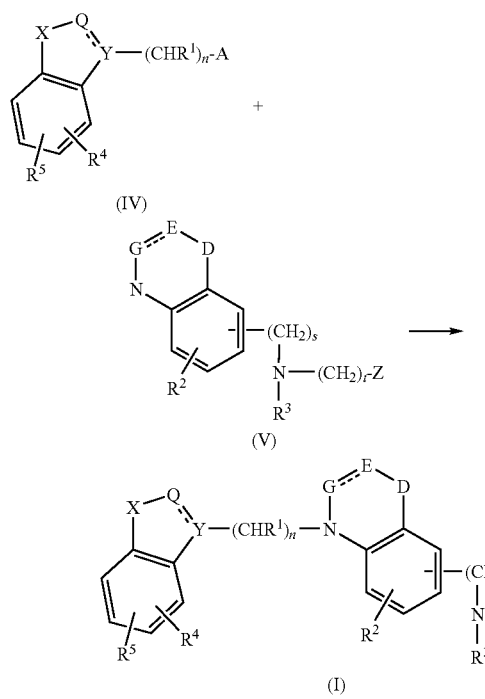

(IV)

(V)

(I)

The compounds of formula (I), wherein —(CHR¹)$_n$— is (CHR¹)$_{n-1}$CH$_2$—, herein referred to as compounds of formula (I-a), can be prepared by reducing an intermediate of formula (VI) with lithium aluminium hydride in a suitable solvent such as tetrahydrofuran.

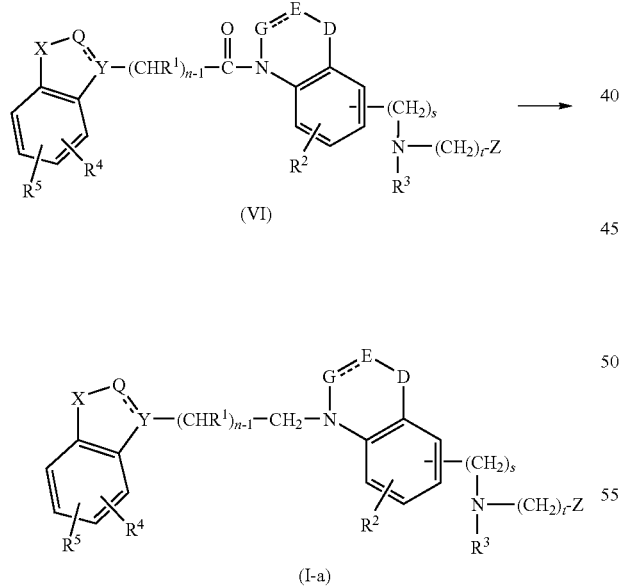

(VI)

(I-a)

The compounds of formula (I-a) can also be prepared by reacting an appropriate carboxaldehyde of formula (VII), with an intermediate of formula (V), in the presence of an appropriate reducing reagent, such as a sodium borohydride, e.g., sodium tetrahydroborate or polymer supported cyanotrihydroborate, in a suitable solvent, such as an alcohol, e.g., methanol, and an acid, e.g. acetic acid.

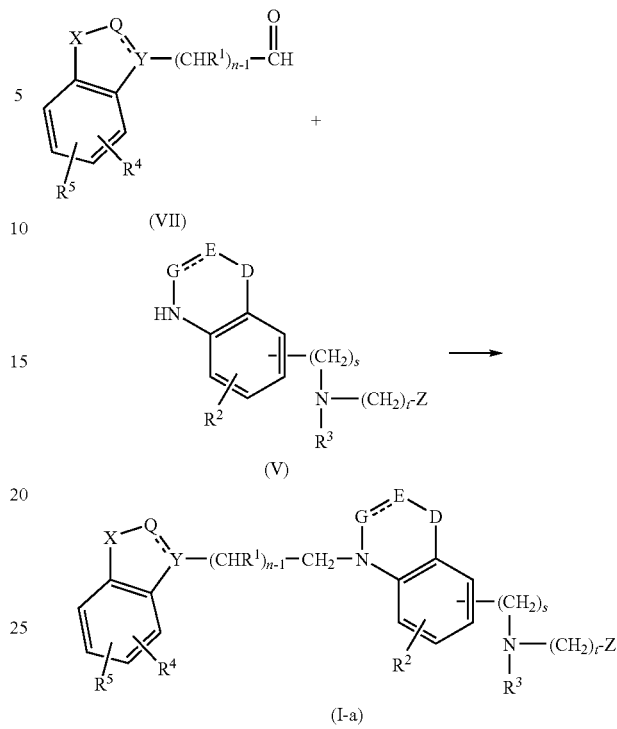

(VII)

(V)

(I-a)

In an identical way the compounds of formula (I) wherein t is 1, herein referred to as compounds of formula (I-b), may be prepared by reacting an intermediate of formula (II) with an appropriate carboxaldehyde of formula HC(=O)Z.

The compounds of formula (I), wherein s is 1, herein referred to as compounds of formula (I-c), can be prepared by reducing an intermediate of formula (VIII) with lithium aluminium hydride in a suitable solvent such as tetrahydrofuran.

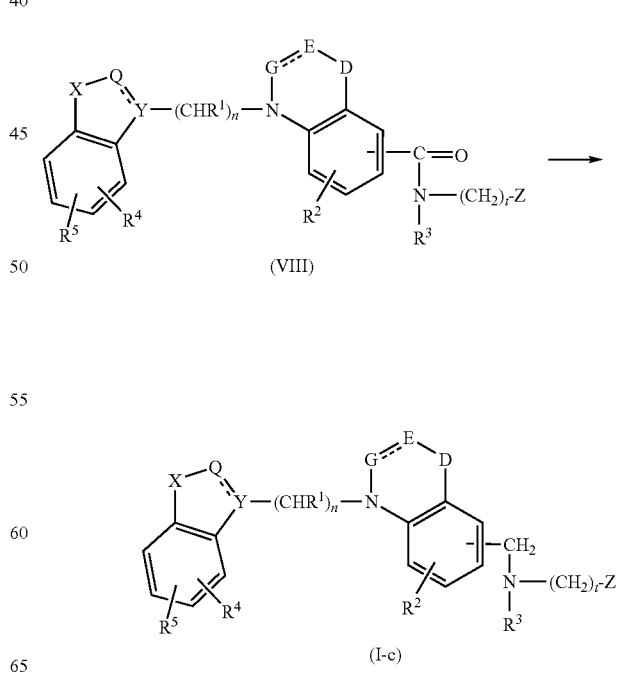

(VIII)

(I-c)

The compounds of formula (I) wherein

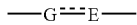

is —C(=O)—CR$^8$R$^{10}$—, with R$^8$ and R$^{10}$ representing hydrogen, herein referred to as compounds of formula (I-f), can be converted into a compound of formula (I) wherein

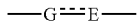

is —CH$_2$—CH$_2$—, herein referred to as compounds of formula (I-g), by reaction with a suitable reducing agent, e.g. tetrahydrofuran-trihydroborane complex.

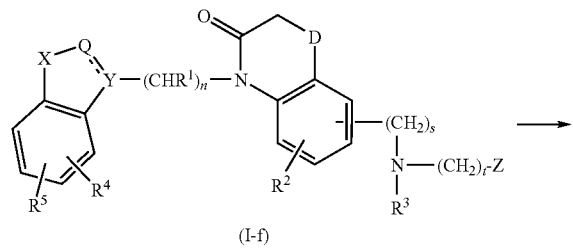

(I-f)

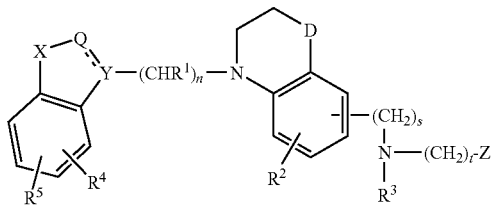

(I-g)

The compounds of formula (I) and their intermediates may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst; etc.

Intermediates of formula (II), wherein s is 0 and R$^3$ is hydrogen, herein referred to as intermediates of formula (II-a), can be prepared by a nitro to amine reduction reaction starting with an intermediate of formula (IX), in the presence of a metal catalyst such as Raney Nickel or palladium on carbon (Pd/C), and an appropriate reductant such as hydrogen, in a suitable solvent such as methanol or ethanol or tetrahydrofuran.

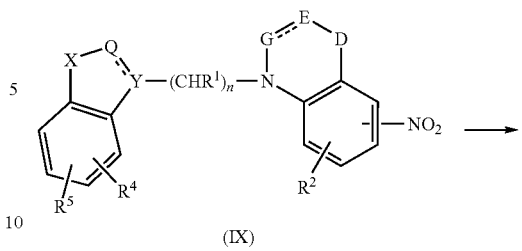

(IX)

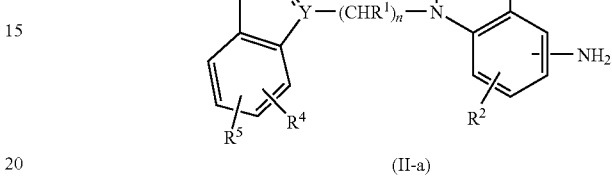

(II-a)

Intermediates of formula (II-a) wherein —(CHR$^1$)$_n$— is (CHR$^1$)$_{n-1}$CH$_2$—, herein referred to as intermediates of formula (II-a-1), can also be prepared by deprotecting an intermediate of formula (XXVII) wherein P represents a suitable protective group, e.g. C$_{1-6}$alkyloxycarbonyl, in the presence of a suitable acid, e.g. hydrochloric acid, and a suitable solvent, e.g. dioxane. Intermediate of formula (XXVII) can be prepared by reacting an intermediate of formula (VII) with an intermediate of formula (XXVIII) in the presence of a suitable reducing agent, e.g. sodium cyanotrihydroborate.

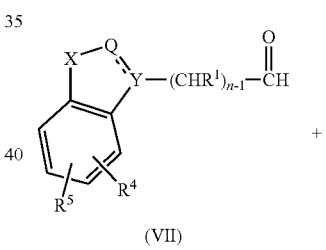

(VII)

+

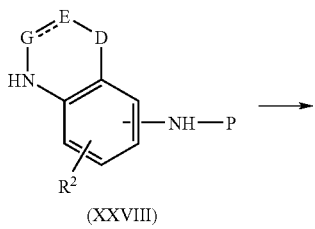

(XXVIII)

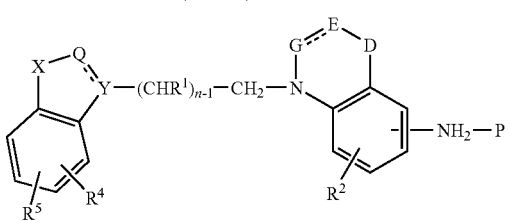

(XXVII)

↓ deprotection

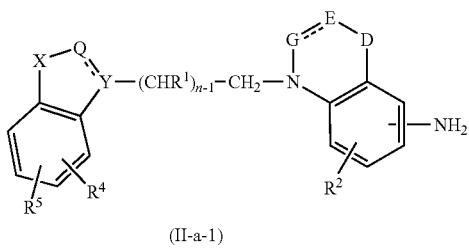

(II-a-1)

Intermediates of formula (VI) can be prepared by reacting an intermediate of formula (VII) with an intermediate of formula (V) in the presence of appropriate dehydrating reagents such as N'-(ethylcarbonimidoyl)-N,N-dimethyl-1,3-propanediamine monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

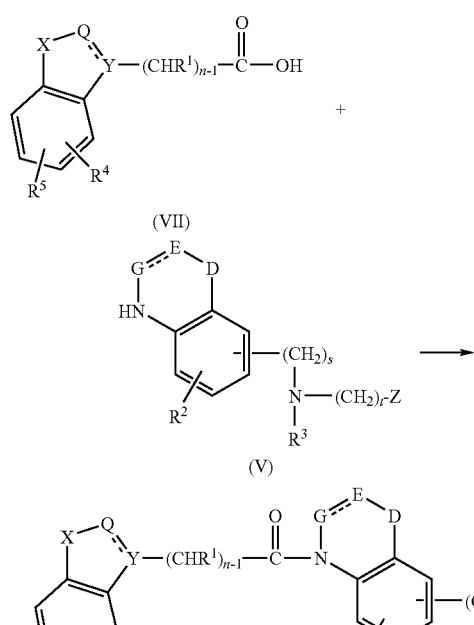

The intermediates of formula (VII) can be prepared by reacting intermediates of formula (XI) with lithium aluminium hydride in a suitable solvent such as tetrahydrofuran.

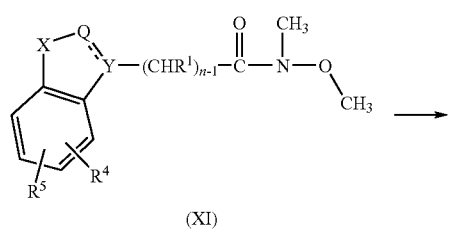

(XI)

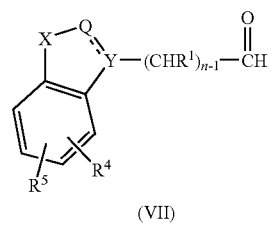

(VII)

The intermediates of formula (VIII) can be prepared by reacting an intermediate of formula (XII) with an intermediate of formula (XIII) in the presence of a suitable dehydrating agent such as 2-chloro-1-methylpyridinium iodide and triethylamine in a suitable solvent such as acetonitrile.

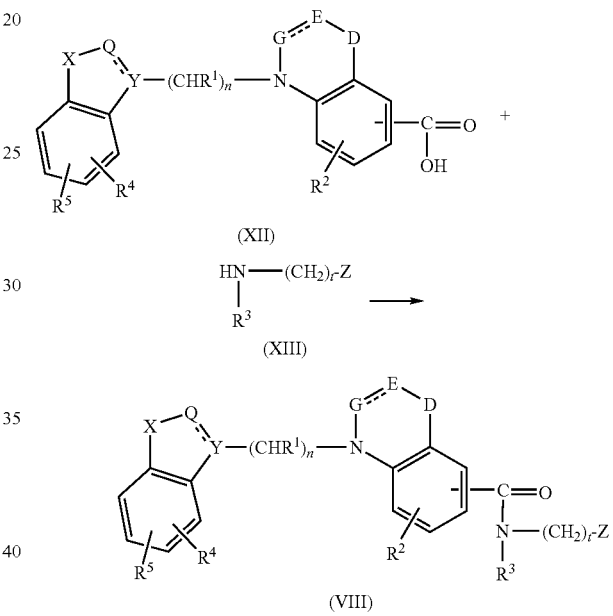

The intermediates of formula (IX) can be prepared by reacting an intermediate of formula (IV) wherein A is an appropriate leaving group as above, with an intermediate of formula (XIV) in an appropriate solvent such as for example, N,N-dimethylformamide, tetrahydrofuran, and the like, preferably in the presence of a suitable base, e.g. $Cs_2CO_3$.

Intermediates of formula (IX) wherein

—G═E— is —C(═O)—$CR^8R^{10}$— or —$CR^7R^9$—C(═O)—, can be converted into an intermediate of formula (IX) wherein

—G═E— is —$CH_2$—$CR^8R^{10}$— or —$CR^7R^9$—$CH_2$—, by reaction with a suitable reducing agent, e.g. tetrahydrofuran-trihydroborane complex.

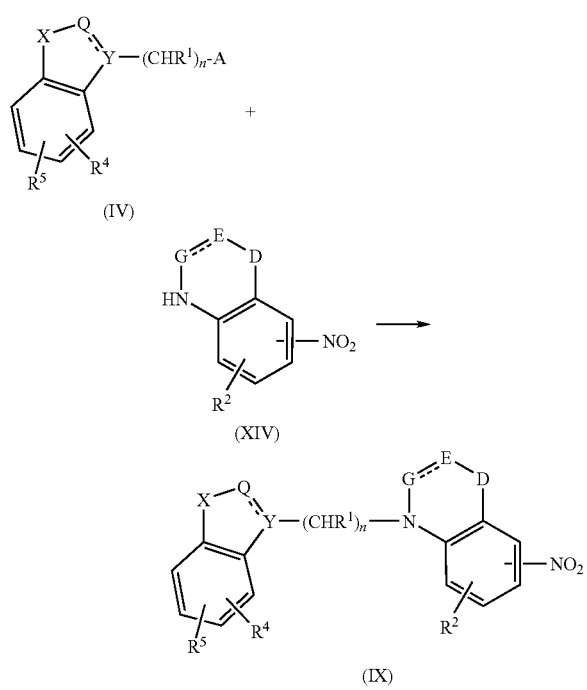

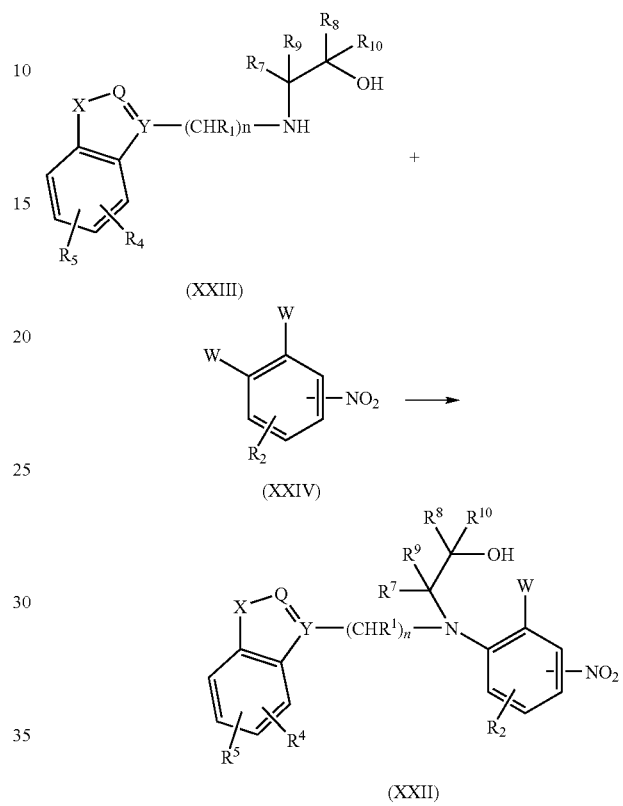

The intermediates of formula (IX) wherein D is O and

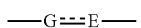

is —CR$^7$R$^9$—CR$^8$R$^{10}$—, herein referred to as intermediates of formula (IX-a), can also be prepared by cyclization of an intermediate of formula (XXII) wherein W is as defined above, in the presence of a suitable base, e.g. sodium hydride or potassium hydroxide, and a suitable solvent, e.g. tetrahydrofuran or N,N-dimethylsulfoxide.

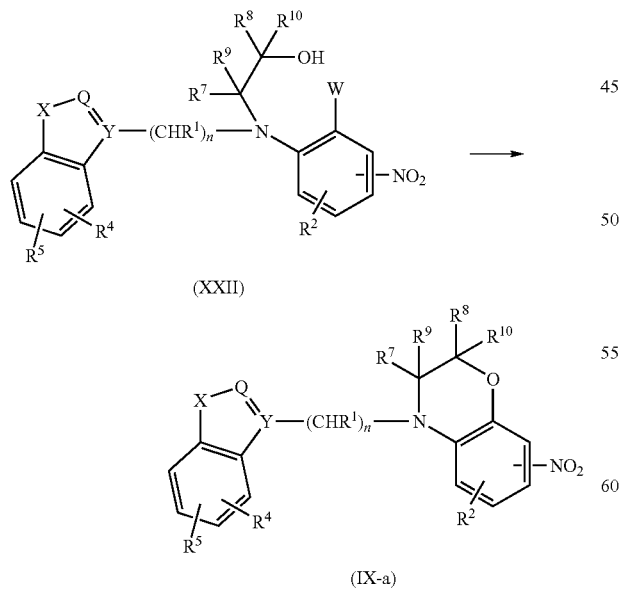

The intermediates of formula (XXII) can be prepared by reacting an intermediate of formula (XXIII) with an intermediate of formula (XXIV) with W as defined above, in the presence of a suitable solvent, e.g. N,N-dimethylsulfoxide. The addition of a suitable base, e.g. sodium bicarbonate, may be utilized to neutralise the acid which is liberated during the course of the reaction.

The intermediates of formula (XXIII) can be prepared by reacting an intermediate of formula (XXV) with an intermediate of formula (XXVI) in the presence of a suitable solvent, e.g. an alcohol, e.g. ethanol.

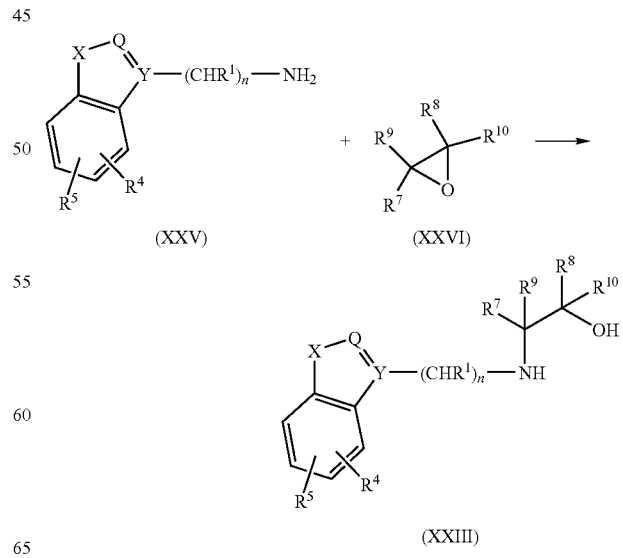

The intermediates of formula (XXVI) wherein $R^7$ and $R^9$ are hydrogen, can be prepared by reacting

with trimethylsulphoxonium iodide in the presence of a suitable base, e.g. potassium hydroxide or sodium hydride, and a suitable solvent, e.g. acetonitrile, N,N-dimethylsulfoxide.

The intermediates of formula (IX-a) can also be prepared by reacting an intermediate of formula (XVII) wherein W is as defined above, with an intermediate of formula (XXV) in the presence of a suitable solvent, e.g. N,N-dimethylsulfoxide, then by addition of an intermediate of formula (XXIV) and a suitable base, e.g. sodium bicarbonate or potassium hydroxide.

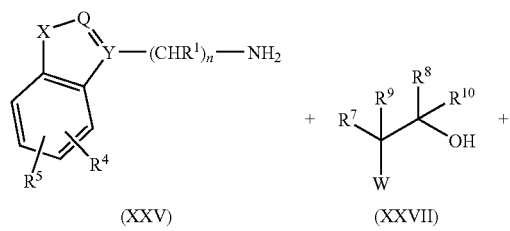

(XXV)        (XXVII)

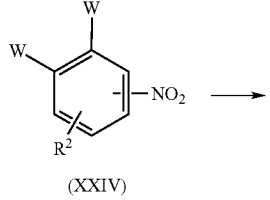

(XXIV)

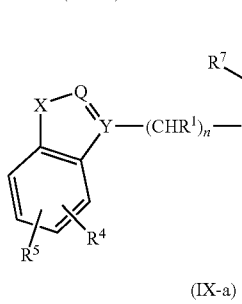

(IX-a)

The intermediates of formula (XII) can be prepared by converting an intermediate of formula (XV) in the presence of sodium hydroxide and water, in a suitable solvent, such as ethanol.

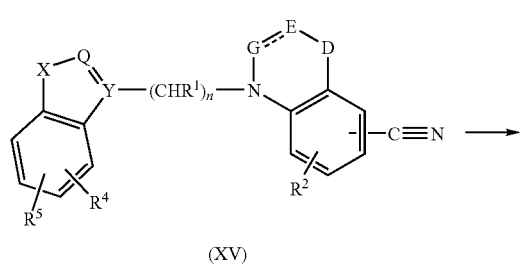

(XV)

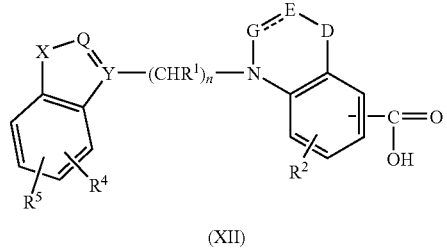

(XII)

The intermediates of formula (XV) can be prepared by reacting an intermediate of formula (IV) wherein A is an appropriate leaving group as above, with an intermediate of formula (XVI) in an appropriate solvent, such as for example, N,N-dimethylformamide, tetrahydrofuran, and the like.

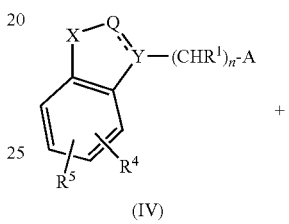

(IV)

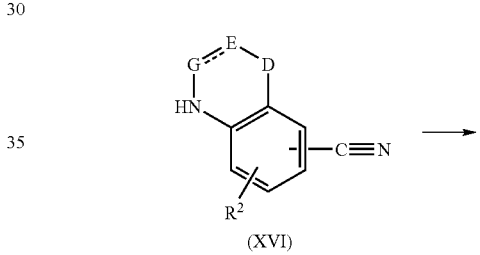

(XVI)

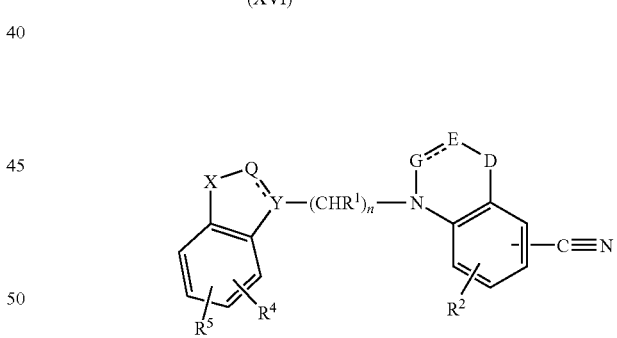

(XV)

The intermediates of any of formulas (V), (XIV) or (XVI) may be prepared inter alia by cyclo-condensation of an intermediate of formula (XVII) wherein T is any of —$(CH_2)_s$—$NR^3$—$(CH_2)_t$—Z, —$NO_2$ or —CN, respectively, and -DH is —OH or —$NH_2$, with any intermediate of formula (XVIII-a), (XVIII-b), (XVIII-c) or (XVIII-d) wherein $L^1$ to $L^8$ are each independently a suitable leaving group, such as for example halo, e.g., fluoro, chloro, bromo, iodo or $C_{1-6}$alkyloxy, e.g. methyloxy, more preferably chloro or bromo, preferably in the presence of a base, e.g. $K_2CO_3$, to neutralise the acid formed during the reaction, in an appropriate inert solvent, e.g. N,N-dimethylformamide.

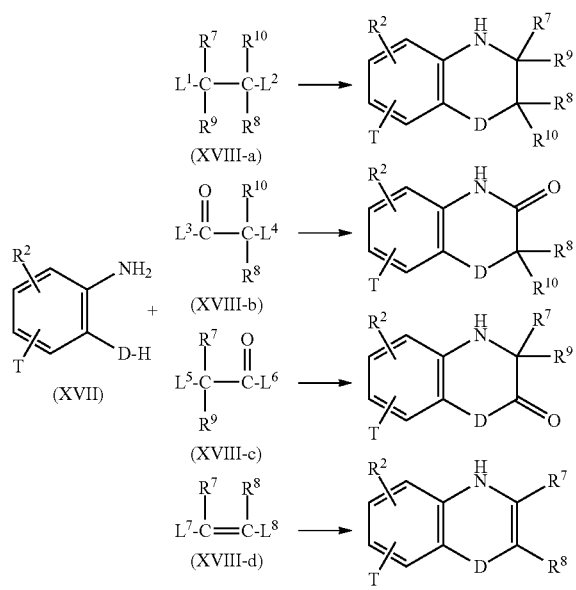

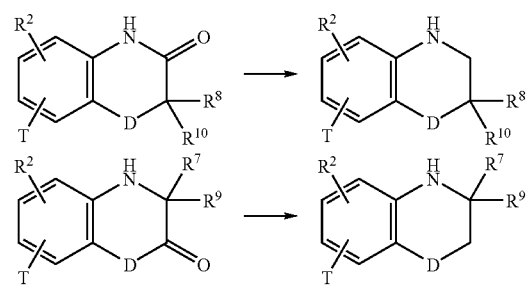

wherein T is any of —(CH$_2$)$_s$—NR$^3$—(CH$_2$)$_t$—Z, —NO$_2$ or —CN.

Intermediates of formula (V) wherein D is N—C$_{1-6}$alkyl and R$^3$ is hydrogen and s is 0, herein referred to as intermediates of formula (V-a), can also be prepared according to the following reaction scheme wherein in step (a) an intermediate of formula (XXIX) is protected with a suitable protective group, e.g. C$_{1-6}$alkyloxycarbonyl, by reaction with e.g. di-tert-butyl-dicarbonate, in a suitable solvent, e.g. dichloromethane, and a suitable base, e.g. triethylamine or 4-dimethylaminopyridine, resulting in an intermediate of formula (XXX) which is alkylated in a next step (b) to an intermediate of formula (XXXI) by reaction with a suitable alkylating agent, e.g. C$_{1-6}$alkyl iodide, in the presence of a suitable base, e.g. di potassium carbonate, and a suitable solvent, e.g. acetonitrile. In step (c), the intermediate of formula (XXXI) is hydrogenated to the corresponding amine of formula (XXXII) in the presence of a suitable catalyst, e.g. Raney nickel, and a suitable solvent, e.g. an alcohol, e.g. methanol. In step (d), the intermediate of formula (XXXII) is reacted with an intermediate of formula (III) according to the reaction procedure described above for compounds of formula (II) starting from intermediates of formula (II) and (III) resulting in an intermediate of formula (V-a).

The intermediates of any of formulas (V), (XIV) or (XVI) wherein

—G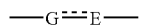E— is —CH$_2$—CR$^8$R$^{10}$— or —CR$^7$R$^9$—CH$_2$— can be prepared from the corresponding intermediates of any of formulas (V), (XIV) or (XVI) wherein —G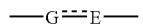E—

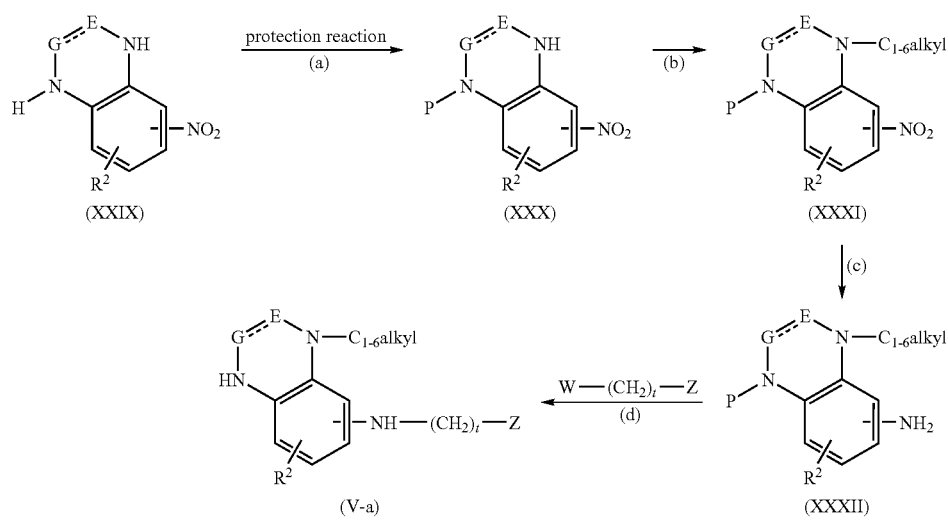

is —C(=)—CR$^8$R$^{10}$— or —CR$^7$R$^9$—C(=O)—, respectively, in the presence of an appropriate reducing reagent, such as borohydride, in a suitable solvent, such as an alcohol, e.g., methanol.

Intermediates of formula (XXI) can be prepared according to the synthesis protocol described above for compounds of formula (I) but starting from the appropriate Si derivative of intermediate (II). This appropriate Si derivative of formula (II) can be prepared according to the protocols above described for intermediate (II).

Some compounds of formula (I) and some of the intermediates may have at least one stereogenic centre in their structure. Any such stereogenic centre may be independently present in an R or an S configuration.

Some of the compounds of formula (I) and some of the intermediates in the present invention may contain an asymmetric carbon atom. Such compounds as prepared in the hereinabove described processes may generally be racemic mixtures of enantiomers or diastereoisomers, which can be separated from one another following art-known resolution procedures. For example, diastereoisomers can be separated by physical methods such as selective crystallization or chromatographic techniques, e.g., counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g., liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The compounds of formula (I), pharmaceutically acceptable acid or base addition salts, solvates, N-oxides and stereoisomeric forms thereof have valuable pharmacological properties in that they inhibit the interaction between p53 and MDM2.

The term "MDM2" (Murine Double Minute2) is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX.

The term "inhibiting the interaction" or "inhibitor of the interaction" is used herein to mean preventing or reducing the direct or indirect association of one or more molecules, peptides, proteins, enzymes or receptors; or preventing or reducing the normal activity of one or more molecules, peptides, proteins, enzymes, or receptors.

The term "inhibitor of the interaction of p53 with MDM2" or "p53-MDM2 inhibitor" is used herein to describe an agent which increases the expression of p53 in the assay described in C.1. This increase may be caused by, but is not limited to, one or more of the following mechanisms of action:

inhibiting the interaction between p53 and MDM2,
direct association with either the MDM2 or the p53 protein,
interactions with upstream or downstream targets, e.g. kinases, or enzyme activities involved in ubiquitination or SUMO modification,
sequestering or transportation of MDM2 and p53 into different cellular compartments,
modulation of proteins associating with MDM2, for example (but not limited to), p63, p73, E2F-1, Rb, p21waf1 or cip1, HIF1alpha, Foxo3A, p14ARF,
downregulating or interference with MDM2 expression and/or MDM2 activity, for example (but not limited to), impacting on its cellular localisation, post-translational modification, nuclear export, ubiquitin ligase activity or interference with binding of MDM2 with the proteasome, modulating the MDM2-proteasome interaction,
direct or indirect stabilization of the p53 protein, e.g. by keeping it in its functional structural form, or by preventing misfolding,
enhancing p53 expression or expression of p53 family members, e.g. p63 and p73.
increasing p53 activity, for example by (but not limited to), enhancing its transcriptional activity and/or
increasing expression of genes and proteins of the p53-signalling pathway, for example (but not limited to) p21waf1, cip1, MIC-1 (GDF-15), PIG-3, Bax, Puma, Noxa, and ATF-3.

Hence, the present invention discloses the compounds of formula (I) for use as a medicine, in particular for the treatment of cancer or related diseases, for inhibiting tumour growth, for inhibiting the interaction between MDM2 and p53, for modulating the MDM2-proteasome interaction.

Furthermore, the invention also concerns the use of a compound for the manufacture of a medicament for the treatment of a disorder mediated through a p53-MDM2 interaction, wherein said compound is a compound of formula (I)

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

With the term "a disorder mediated through a p53-MDM2 interaction" is meant any undesired or detrimental condition that results from the interaction between the MDM2 protein and p53 or other cellular proteins that induce apoptosis, induce cellular death, or regulate the cell cycle.

This invention also provides a method for treating a disorder mediated through a p53-MDM2 interaction by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type or mutant p53 and/or in tumours overexpressing MDM2.

Thus, this invention also provides a method for inhibiting tumour growth by administering an effective amount of a compound of the present invention, to a subject, e.g. a mammal (and more particularly a human) in need of such treatment.

Examples of tumours including adult and pediatric malignancies, which may be inhibited by the compounds of the present invention include, but are not limited to, lung cancer including small cell lung cancer and non-small cell lung cancer (e.g. adenocarcinoma), pancreatic cancers, colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, gliomas, benign tumour of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions by administering an effective amount of a compound of the present invention, to a subject, e.g. a mammal (and more particularly a human) in need of such treatment.

The compounds of the present invention can also be useful for the treatment of diseases associated with conformational unstable or misfolded proteins.

Examples of diseases associated with conformational unstable or misfolded proteins include but are not limited to: cystic fibrosis (CFTR), Marfan syndrom (fibrillin), Amyotrophic lateral sclerosis (superoxide dismutase), scurvy (collagen), maple syrup urine disease (alpha-ketoacid dehydrogenase complex), osteogenesis imperfecta (type) procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), αI-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit the interaction between MDM2 and p53 or other cellular proteins that induce apoptosis, induce cellular death, regulate the cell cycle, regulate tumor cell migration or invasion or metastasis, in particular an amount sufficient to modulate the MDM2-proteasome interaction.

The oncogenic potential of MDM2 is not only determined by its ability to suppress p53, but also by its ability to regulate other tumour suppressor proteins, e.g. the retinoblastoma protein pRb and the closely associated E2F1 transcription factor, p63, p73.

Thus, the compound of the invention is administered in an amount sufficient to modulate the interaction between MDM2 and the E2F1 transcription factors.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a p53-MDM2 inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoklen for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, caminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

As stated above, the compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the p53-MDM2 inhibitor according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the p53-MDM2 inhibitor according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a p53-MDM2 inhibitor according to the invention and as further active ingredient one or more anticancer agent, as a combined preparation for simultaneous, separate or sequential use in the treatment of patients suffering from cancer.

The one or more other medicinal agents and p53-MDM2 inhibitor may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and p53-MDM2 inhibitor being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment. These dosages may be administered for example once, twice or more per course of treatment, which may be repeated for example every 7, 14, 21 or 28 days.

The compounds of formula (I), the pharmaceutically acceptable acid addition salts and stereoisomeric forms thereof can have valuable diagnostic properties in that they can be used for detecting or identifying a p53-MDM2 interaction in a biological sample comprising detecting or measuring the formation of a complex between a labelled compound and/or p53 and/or MDM2 and or other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^{3}$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Biological samples can be defined as body tissue or body fluids. Examples of body fluids are cerebrospinal fluid, blood, plasma, serum, urine, sputum, saliva and the like. The following examples illustrate the present invention.

EXPERIMENTAL PART

Hereinafter, "DCM" is defined as dichloromethane, "DMF" is defined as N,N-dimethylformamide, "DMSO" is defined as dimethylsulfoxide, "DIEA" is defined as diisopropylethylamine, "DIPE" is defined as diisopropyl ether, "EtOAc" is defined as ethyl acetate, "Et$_2$O" is defined as diethyl ether, "EtOH" is defined as ethanol, "MeOH" is defined as methanol, and "THF" is defined as tetrahydrofuran.

A. Preparation of the Intermediate Compounds

Example A1 a) Preparation of Intermediate 1

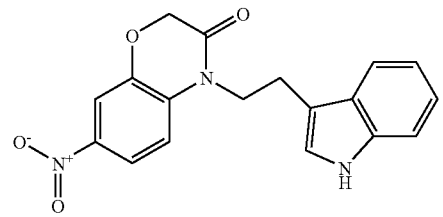

A mixture of 7-nitro-2H-1,4-benzoxazin-3(4H)-one (0.0051 mol), 3-(2-bromoethyl)-1H-indole (0.0062 mol) and cesium carbonate (0.0062 mol) was dried for 40 minutes. DMF dry (16 ml) and THF dry (4 ml) were added. The mixture was stirred at 85° C. for 2 hours and half, cooled to room temperature, poured out into ice water (160 ml), stirred at room temperature for 1 hour, filtered off, washed with ether (3 times 80 ml). The residue was collected and dried for a night, yielding 1.63 g (94%) of intermediate 1.

b) Preparation of Intermediate 2

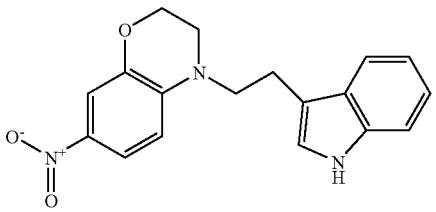

Intermediate 1 (0.0037 mol) was added portion wise to borohydride (1M in THF/0.018 mol) at 0° C. The mixture was stirred at 60° C. for 1 hour and half, cooled to 0° C. Methanol dry (3.5 ml) was added. The mixture was stirred at 60° C. for 1 hour, cooled to room temperature. The solvent was evaporated under reduced pressure. The residue was taken up with NH$_4$OH (15%, 4 ml) and water, extracted with chloroform (4 times 80 ml). The organic layers were combined, extracted, dried over MgSO$_4$, filtered off and the solvent was evaporated. The residue was purified by column chromatography over silica gel (eluent: DCM/cyclohexane/EtOH 50/50/0.1 to 50/50/0.15). The residue was purified by column chromatography over silica gel (eluent: cyclohexane/EtOAc 60/40 to 50/50). The pure fractions were collected and the solvent was evaporated, yielding 0.779 g (65%) of intermediate 2.

c) Preparation of Intermediate 3

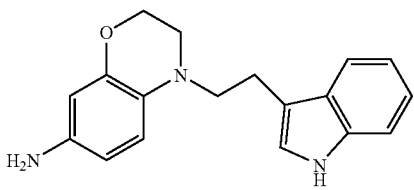

A solution of intermediate 2 (0.0022 mol) and Pd/C 10% (0.712 g) in THF dry (25 ml) was hydrogenated for 1 hour and half, filtered over celite. Celite was washed with THF. The solvent was evaporated. The residue (0.692 g) was purified by column chromatography over silica gel (eluent: cyclohexane/EtOAc 60/40 to 50/50). The pure fractions were collected and the solvent was evaporated, yielding 0.405 g (62%) of intermediate 3.

Example A2

Preparation of Intermediate 4

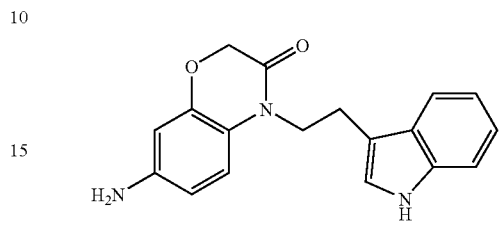

A solution of intermediate 1 (0.0032 mol) and Pd/C (1.04 g) in THF dry (20 ml) and methanol dry (10 ml) was hydrogenated for 2 hours and 40 minutes, filtered over celite. Celite was washed with methanol (250 ml in average). The solvent was evaporated under reduced pressure. The residue (0.92 g) was purified by column chromatography over silica gel (eluent: DCM/methanol 100/0 to 99/1). The pure fractions were collected and the solvent was evaporated, yielding 0.789 g (77%) of intermediate 4.

Example A3 a 1) Preparation of Intermediate 5

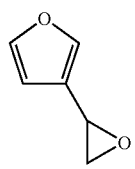

Potassium hydroxide (124.889 mmol) was added to a mixture of trimethylsulphoxonium iodide (20.815 mmol) in acetonitrile (40 ml) and water (5.204 mmol) at 40° C. The reaction mixture was stirred at 40° C. for 30 minutes. A solution of 3-furaldehyde (20.815 mmol) in acetonitrile (20 ml) was added dropwise. The reaction mixture was stirred at this temperature for 18 hours more. The reaction mixture was filtered through a pad of celite and the insoluble material was washed with Et$_2$O. The filtrate was evaporated to dryness, yielding 4.5 g of (>100%) of intermediate 5.

a 2) Preparation of Intermediate 37

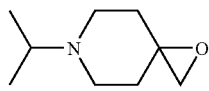

Trimethylsulphoxonium iodide (24.432 mmol) was added portionwise at 5° C. under N$_2$ flow to a suspension of sodium hydride 60% in oil (23.369 mmol) in DMSO (30 ml). The reaction mixture was stirred for 30 minutes and a solution of 1-(1'methylethyl)-4-piperidone in DMSO (10 ml) was added. The reaction mixture was stirred at room temperature for 18 hours more. The reaction mixture was poured onto water and extracted with Et₂O. The organic layer was decanted, washed with a saturated solution of NaCl, dried over MgSO₄, filtered and evaporated to dryness, yielding 2.5 g (76%) of intermediate 37.

b 1) Preparation of Intermediate 6

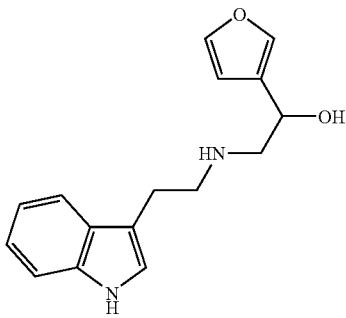

A mixture of tryptamine 98% (13.873 mmol) and intermediate 5 (20.81 mmol) in EtOH was stirred at 60° C. for 18 hours. The reaction mixture was evaporated to dryness and the residue was purified by high-performance liquid chromatography (Irregular SiOH 20-45 μm 450 g MATREX mobile phase: NH₄OH 0.5%; DCM 92% MeOH 8%), yielding 650 mg of intermediate 6.

b 2) Preparation of Intermediate 10

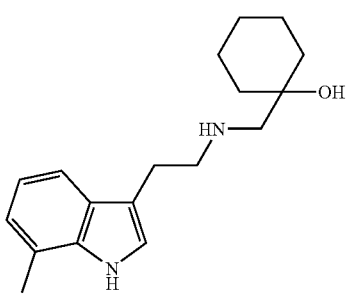

A mixture of 7-methyltryptamine 98% (11.478 mmol) and 1-oxaspiro(2.5)octane (17.217 mmol) in EtOH (40 ml) was stirred at 60° C. for 18 hours. The reaction mixture was cooled to room temperature and evaporated to dryness. The residue was purified by HPLC (H647 300 g SiO₂ 15/40 μm—eluent: DCM/MeOH/NH₄OH 90/10/1). The pure fractions were collected and evaporated to dryness, yielding 2.7 g (82%) of intermediate 10.

c) Preparation of Intermediate 7

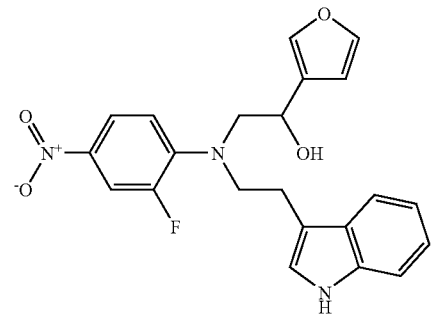

A mixture of intermediate 6 (2.404 mmol), 3,4-difluoronitrobenzene (3.126 mmol) and NaHCO₃ (4.809 mmol) in DMSO (6 ml) was stirred at 80° C. for 18 hours. The reaction mixture was cooled to room temperature, poured onto iced water and extracted with EtOAc. The organic layer was decanted, dried over MgSO₄, filtered and evaporated to dryness. The residue was purified by HPLC (30 g SiO₂ 15/40 μm—eluent: DCM 100). The pure fractions were collected and evaporated to dryness, yielding 420 mg (42%) of intermediate 7.

d) Preparation of Intermediate 8

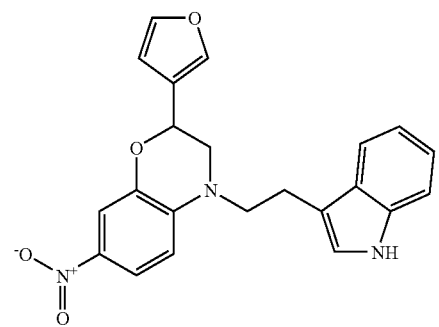

A mixture of intermediate 7 (1.026 mmol) and sodium hydride 60% in oil (3.59 mmol) in THF (10 ml) was refluxed for 30 minutes. The reaction mixture was cooled to room temperature, quenched with water and extracted with DCM. The organic layer was decanted, dried over MgSO₄, filtered and evaporated to dryness. The residue was purified by HPLC (30 g SiO$_2$ 15/40 μm—eluent: DCM 100). The pure fractions were collected and evaporated to dryness, yielding 130 mg (32%) of intermediate 8.

e) Preparation of Intermediate 9

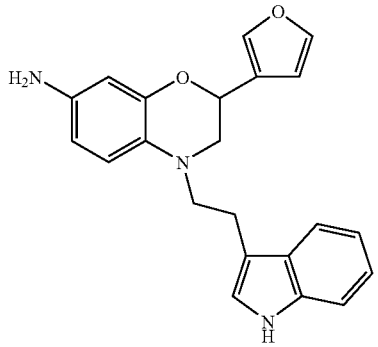

A mixture of intermediate 8 (0.334 mmol) and Raney Nickel (0.2 g) in MeOH (20 ml) was hydrogenated at room temperature under atmosphere pressure of H$_2$ for 2 hours. The catalyst was removed by filtration over a pad of celite and the filtrate was evaporated to dryness, yielding 100 mg (83%) of intermediate 9.

Following intermediates are prepared according to A3

Intermediate 15

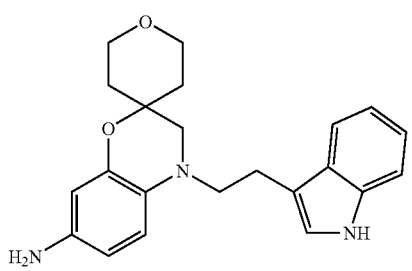

Intermediate 14

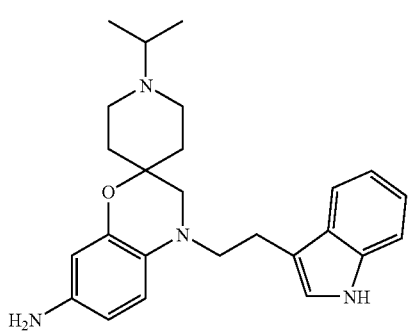

Intermediate 30

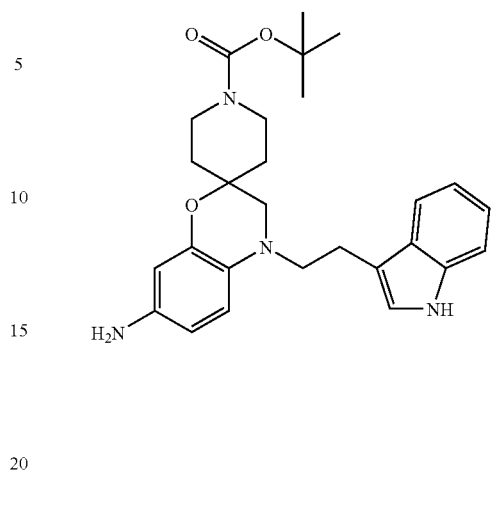

Intermediate 31

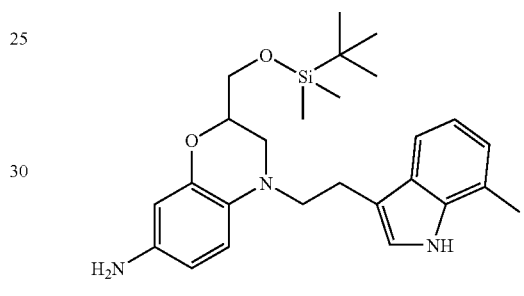

Example A a) Preparation of Intermediate 11

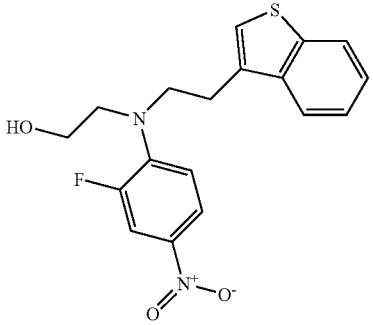

A mixture of benzo[b]thiophene-3-ethanamine (0.0274 mol) and 2-chloroethanol (0.0274 mol) in DMSO (20 ml) was heated at 80° C. overnight and cooled to room temperature. 3,4-difluoronitrobenzene (0.0411 mol) and NaHCO$_3$ (0.0411 mol) were added. The mixture was heated at 60° C. for 2 hours, cooled to room temperature, poured out into ice and extracted with EtOAc. The organic layer was dried over MgSO$_4$, filtered and evaporated till dryness. The residue (12.5 g) was purified by high-performance liquid chromatography (Irregular SiOH 20-45 μm 450 g MATREX mobile phase; cyclohexane 60% EtOAc 40%). The pure fractions were collected and the solvent was evaporated, yielding 2.95 g (30%) of intermediate 11.

b) Preparation of Intermediate 12

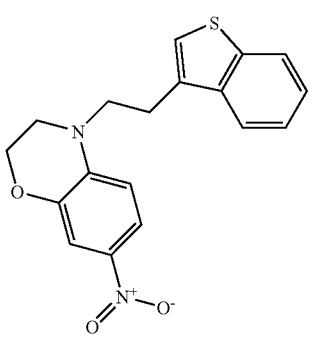

Sodium hydride (0.0286 mol) was added portionwise to intermediate 11 (0.00819 mol) in THF (30 ml). The mixture was heated at 65° C. overnight, poured out into ice and extracted with EtOAc. The organic layer was dried over MgSO$_4$, filtered and evaporated. The residue (3.06 g) was purified by high-performance liquid chromatography (Irregular SiOH 15-40 μm 300 g MERCK mobile phase; Cyclohexane 80% DCM 20%). The pure fractions were collected and the solvent was evaporated, yielding 1.1 g (39%) of intermediate 12.

c) Preparation of Intermediate 13

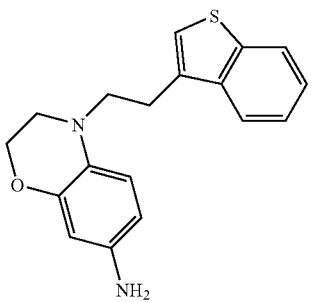

A solution of intermediate 12 (0.00323 mol) in MeOH (50 ml) was hydrogenated for one hour at room temperature with Raney Nickel (0.9 g) as a catalyst under a 2 bar pressure. The catalyst was filtered off and the filtrate was evaporated till dryness, yielding 0.9 g (90%) of intermediate 13. This product was used without further purification in the next step.

Example A5 a) Preparation of Intermediate 16

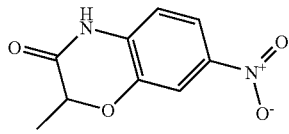

2-bromo-propanoic acid, methyl ester (0.03 mol) was added to a solution of potassium fluoride (0.075 mol) in DMF (25 ml). The mixture was stirred at room temperature for 15 minutes. 2-amino-5-nitro-phenol (0.03 mol) was added. The mixture was stirred at 60° C. for 6 hours, poured out into ice water (150 ml), filtered, washed with water and dried, yielding 7 g of intermediate 16.

b) Preparation of Intermediate 17

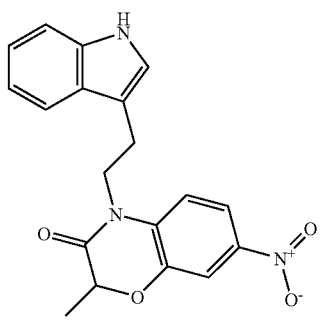

A mixture of intermediate 16 (0.0144 mol), 3-(2-bromoethyl)-1H-Indole (0.0173 mol) and cesium carbonate (0.0173 mol) was added to a solution of DMF (96 ml) in THF (24 ml). The mixture was stirred at 85° C. for 2 hours and half, cooled to room temperature, poured out into ice water, stirred at room temperature for 1 hour, filtered off, washed with ether (3 times) and dried, yielding 3.9 g (77%) of intermediate 17.

c) Preparation of Intermediate 18

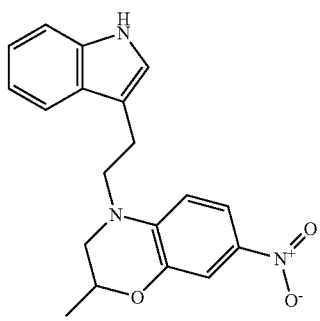

Intermediate 17 (0.0043 mol) was added portion wise to a solution of tetrahydrofuran-borane (0.0205 mol) at 0° C. The mixture was stirred at 60° C. for one hour and half. Water was added at 0° C. The mixture was filtered over celite. The organic layer was extracted with EtOAc, dried (MgSO₄), filtered and the solvent was evaporated in vacuum. The residue (2 g) was purified by column chromatography over silica gel (90 g) (eluent: Cyclohexane/EtOAc 70/30; 15-40 μm). The pure fractions were collected and the solvent was evaporated, yielding 1 g (70%) of intermediate 18.

Preparation of Intermediate 19

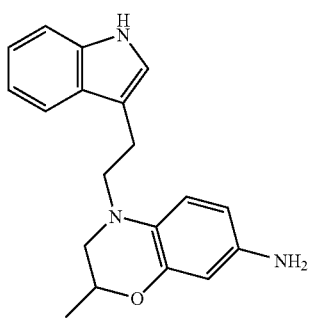

Palladium (0) (0.1 g) was added in a solution of intermediate 18 (0.003 mol) in MeOH/THF (10/20) (50 ml) under nitrogen flow. The mixture was hydrogenated at room temperature for a night under a 1 bar pressure. The mixture was filtered over celite and the solvent was evaporated, yielding 0.8 g of intermediate 19.

Following intermediate is prepared according to A5.

Intermediate 20

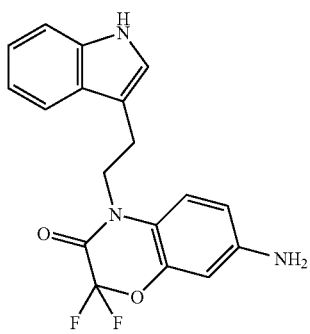

Example A6 a) Preparation of Intermediate 21

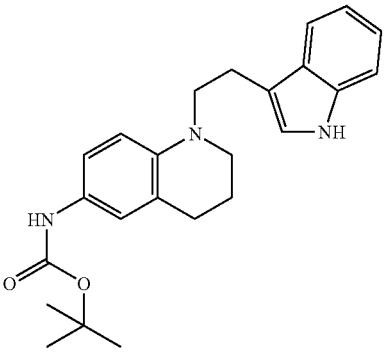

A mixture of N-(1,2,3,4-tetrahydro-6-quinolinyl)-carbamic acid, 1,1-dimethylethyl ester (2.819 mmol), 1H-Indole-3-acetaldehyde (5.638 mmol), sodium cyanotrihydroborate (3.805 mmol) and acetic acid (100 μl) in MeOH (10 ml) was stirred at room temperature for 18 hours. The reaction mixture was quenched with a 10% solution of potassium carbonate and extracted with DCM. The organic layer was decanted, dried over MgSO₄, filtered and evaporated to dryness. The residue was purified by HPLC (30 g SiO₂ 15/40 μm—eluent: DCM 100). The pure fractions were collected and evaporated to dryness, yielding 888 mg (80%) of intermediate 21.

b) Preparation of Intermediate 22

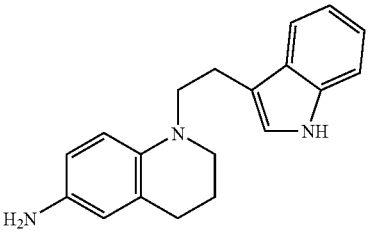

A mixture of intermediate 21 (2.043 mmol) and HCl 3N (10 ml) in dioxane (10 ml) was heated at 65° C. for 30 minutes. The reaction mixture was cooled to room temperature, poured onto a 10% solution of potassium carbonate and extracted with DCM. The organic layer was decanted, dried over MgSO₄, filtered and evaporated to dryness, yielding 600 mg (100%) of intermediate 22.

Example A7 a) Preparation of Intermediate 24

A mixture of tryptamine (0.0125 mol) and 2-chloroethanol (0.00892 mol) in DMSO (15 ml) was heated to 80° C. for 18 hours and cooled to room temperature. 3,4-5-trifluoronitrobenzene (0.0125 mol) and NaHCO₃ (0.0125 mol) were added. The mixture was heated at 60° C. overnight and cooled to room temperature. A solution of potassium hydroxide (0.0267 mol) in water (2 ml) was added. The mixture was heated at 100° C. overnight, cooled to room temperature, poured out into ice and extracted with EtOAc. The organic layer was dried over MgSO₄, filtered and evaporated till dryness. The residue was purified by HPLC(H651 300 g SiO₂ 15/40 μm—eluent: DCM/cyclohexane 70/30). The pure fractions were collected and evaporated to dryness, yielding 323 mg (10% over 3 steps) of intermediate 24.

b) Preparation of Intermediate 25

A mixture of intermediate 24 and Raney Nickel (280 mg) in MeOH/THF 90/10 (20 ml) was hydrogenated at room temperature under atmospheric pressure of H₂ for 1.5 hours. The catalyst was removed by filtration and the filtrate was evaporated to dryness, yielding 213 mg (83%) of intermediate 25.

Example A8 a) Preparation of Intermediate 26

A mixture of 7-methyltryptamine (0.00574 mol) and 2-chloroethanol (0.00383 mol) in DMSO (6 ml) was heated to 80° C. for 5 hours, cooled to room temperature, poured out into ice and extracted with EtOAc. The organic layer was dried over MgSO₄, filtered and evaporated till dryness, yielding 0.83 g (99%) of intermediate 26.

This product was used without further purification in the next step.

b) Preparation of Intermediate 27

A mixture of 3,4-difluoronitrobenzene (0.0057 mol), NaHCO₃ (0.0057 mol) and intermediate 26 (0.0038 mol) in DMSO (7 ml) was heated at 60° C. for 2 hours, cooled to room temperature, poured onto ice-water and extracted with EtOAc. The organic layer was dried over MgSO₄, filtered and evaporated till dryness. The residue was purified by column chromatography over 300 g of silica gel 15-40 μm (eluent:

DCM/MeOH: 99/1). The pure fractions were collected and the solvent was evaporated, yielding 0.418 g (31%) of intermediate 27.

c) Preparation of Intermediate 28

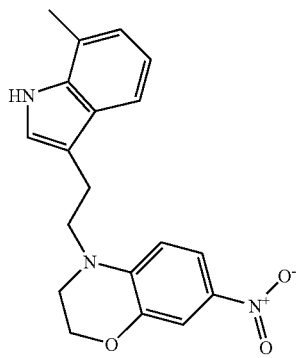

To intermediate 27 (0.000227 mol) in DMSO (6 ml) was added potassium hydroxide (0.00068 mol) in water (few drops). The mixture was stirred at room temperature overnight, poured out into ice and extracted with EtOAc. The organic layer was dried over MgSO₄, filtered and evaporated till dryness, yielding 0.07 g (91%) of intermediate 28.

d) Preparation of Intermediate 29

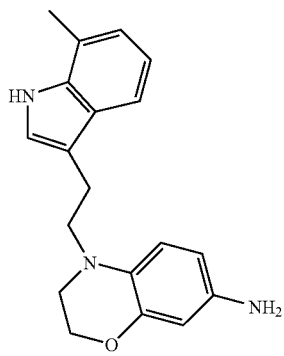

A solution of intermediate 28 (0.000978 mol) in MeOH (10 ml) was hydrogenated for one hour at room temperature with Raney Nickel (0.3 g) as a catalyst under a 2 bar pressure. The catalyst was filtered off and the filtrate was evaporated till dryness, yielding 0.3 g (100%) of intermediate 29. This product was used without further purification in the next step.

Example A9

Preparation of Intermediate 32

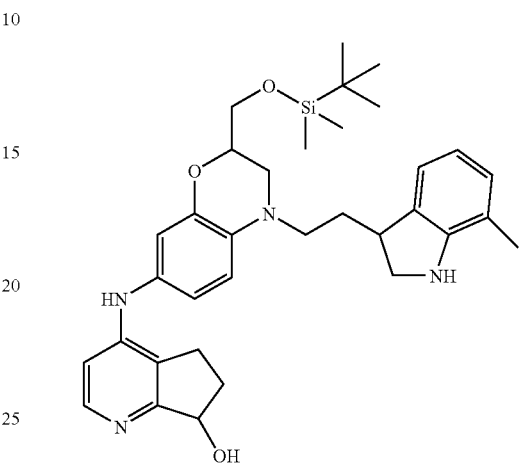

A mixture of intermediate 31 (see Example A3) (0.432 mmol), 4-chloro-6,7-dihydro-5H-cyclopenta[b]pyridin-7-ol (0.518 mmol) and HCl/dioxane 4N (0.0863 mmol) in acetonitrile (2 ml) and EtOH (16 ml) was heated at 65° C. for 18 hours. The reaction mixture was cooled to room temperature, diluted with DCM and quenched with a 10% solution of potassium carbonate. The organic layer was decanted, dried over MgSO₄, filtered and evaporated to dryness. The residue was purified by HPLC (10 g SiO₂ 15/40 µm—eluent: DCM/MeOH/NH₄OH 95/5/0.5). The pure fractions were collected and evaporated to dryness, yielding 163 mg (64%) of intermediate 32.

a) Preparation of Intermediate 33

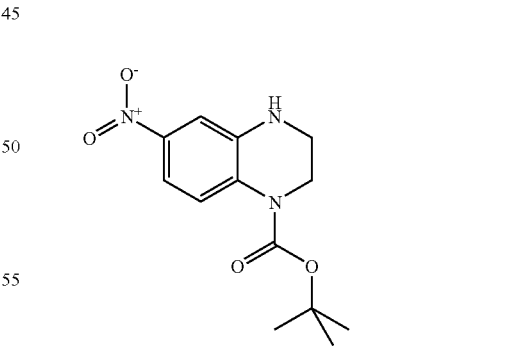

A mixture of 1,2,3,4-tetrahydro-6-nitro-quinoxaline (22.324 mmol), di-tert-butyl dicarbonate (22.324 mmol), triethylamine (44.648 mmol) and 4-dimethylaminopyridine (4.465 mmol) in DCM (40 ml) was stirred at room temperature for 2 hours. The reaction mixture was poured onto water and extracted with DCM. The organic layer was decanted, dried over MgSO₄, filtered and evaporated to dryness. The residue (7.7 g) was purified by HPLC (90 g SiO₂ 15/40

μm—eluent: DCM 100 to DCM/MeOH 99/1). The pure fractions were collected and evaporated to dryness, yielding 3.55 g (57%) of intermediate 33.

b) Preparation of Intermediate 34

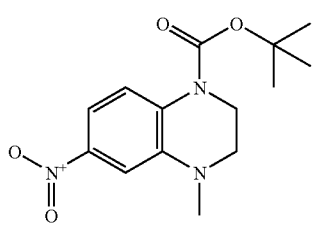

A mixture of intermediate 33 (10.383 mmol), iodomethane (14.537 mmol) and $K_2CO_3$ (16.613 mmol) in acetonitrile (30 ml) was heated at 90° C. all over the weekend. The reaction mixture was quenched with water and extracted with DCM. The organic layer was decanted, dried over $MgSO_4$, filtered and evaporated to dryness. The residue was purified by HPLC (90 g $SiO_2$ 15/40 μm—eluent: DCM 100). The pure fractions were collected and evaporated to dryness, yielding 2.15 g (70%) of intermediate 34.

c) Preparation of Intermediate 35

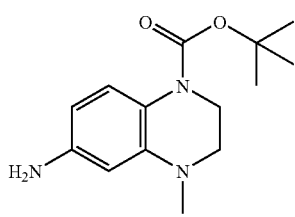

A mixture of intermediate 34 (3.409 mmol), Raney Nickel (1 g) in MeOH (10 ml) was hydrogenated at room temperature under atmospheric pressure for 1 hour. The catalyst was removed by filtration and the filtrate was evaporated to dryness, yielding 814 mg (90%) of intermediate 35.

d) Preparation of Intermediate 36

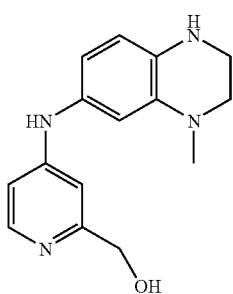

A mixture of intermediate 35 (1.029 mmol), 4-chloro-2-pyridinemethanol (1.235 mmol) and HCl/dioxane 4N (1.235 mmol) in acetonitrile (3 ml) and EtOH (2.4 ml) was heated at 65° C. for 18 hours. The reaction mixture was cooled to room temperature and HCl 3N (2 ml) was added. The reaction mixture was heated at 65° C. for 4 hours more. The reaction mixture was diluted with EtOAc and quenched with a 10% solution of potassium carbonate. The organic layer was decanted, dried over $MgSO_4$, filtered and evaporated to dryness. The residue was purified by HPLC (30 g $SiO_2$ 15/40 μm—eluent: DCM/MeOH/$NH_4OH$ 90/10/1). The pure fractions were collected and evaporated to dryness, yielding 185 mg (66%) of intermediate 36.

B. Preparation of the Final Compounds

Example B1

Preparation of Compound 1

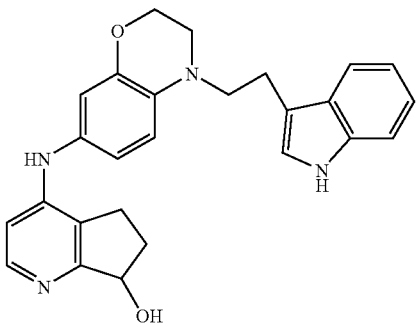

A mixture of intermediate 3 (0.0004 mol) and 4-chloro-6,7-dihydro-5H-cyclopenta[b]pyridin-7-ol (0.0005 mol) was stirred at 150° C. for 20 minutes, cooled to room temperature, extracted with $NaHCO_3$/DCM/methanol (few drops) (4 times 40 ml). The organic layers were combined, dried over $MgSO_4$, filtered off and the solvent was evaporated. The residue (0.218 g) was purified by column chromatography over silica gel (DCM/methanol 95/5, 93/7 to 90/1). The pure fraction was collected and the solvent was evaporated, yielding 0.150 g (86%) of compound 1.

Example B2

Preparation of Compound 2

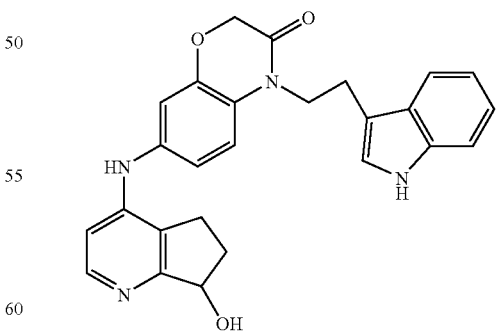

A mixture of intermediate 4 (0.0003 mol) and 4-chloro-6,7-dihydro-5H-cyclopenta[b]pyridin-7-ol (0.0003 mol) was stirred at 150° C. for 20 minutes, cooled to room temperature, extracted with $NaHCO_3$/DCM/methanol (few drops). The organic layers were combined, dried over $MgSO_4$, filtered off and the solvent was evaporated. The residue (0.174 g) was purified by column chromatography over silica gel (DCM/methanol 95/5, 93/7 to 90/1). The pure fraction was collected and the solvent was evaporated, yielding 0.097 g (68%) of compound 2.

Example B3

Preparation of Compound 3

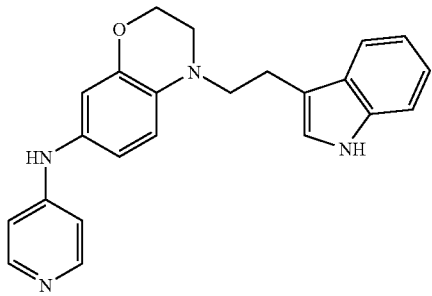

A mixture of intermediate 3 (0.0006 mol) and 4-chloropyridine hydrochloride (0.018 mol) was stirred at 150° C. for 20 minutes, cooled to room temperature, extracted with NaHCO$_3$/DCM/methanol (few drops) (4 times 40 ml). The organic layers were combined, dried over MgSO$_4$, filtered off and the solvent was evaporated. The residue (0.276 g) was purified by column chromatography over silica gel (DCM/methanol 95/5, 93/7 to 90/1). The pure fraction was collected and the solvent was evaporated, yielding 0.118 g (51%) of compound 3.

Example B4

Preparation of Compound 4

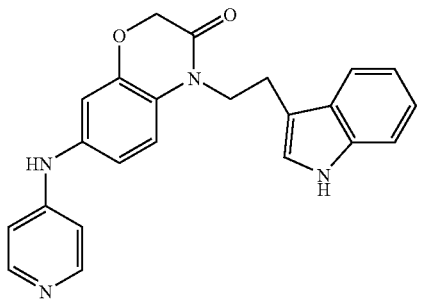

A mixture of intermediate 4 (0.0005 mol) and 4-chloropyridine hydrochloride (0.0015 mol) was stirred at 180° C. for 15 minutes, stirred at 120° C. for 15 minutes, cooled to room temperature. The residue was taken up with saturated NaHCO$_3$, extracted with DCM/methanol (few drops). The organic layer was dried over MgSO$_4$, filtered off and the solvent was evaporated. The residue was purified by column chromatography over silica gel (DCM/methanol 95/5, 93/7 to 90/1). The pure fraction was collected and the solvent was evaporated, yielding 0.068 g (30%) of compound 4.

Example B5

Preparation of Compound 5

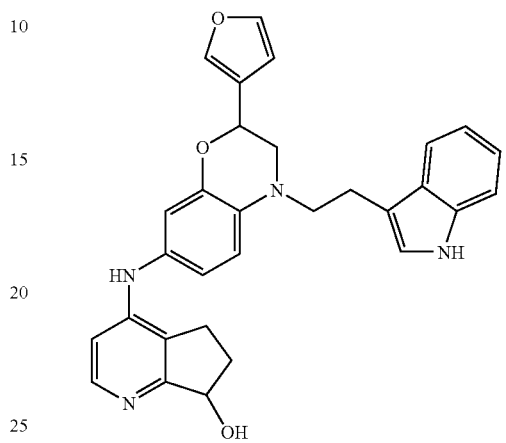

A mixture of intermediate 9 (0.139 mmol) and 4-chloro-6,7-dihydro-5H-cyclopenta[b]pyridin-7-ol (0.167 mmol) in HCl/dioxane 4N (0.0278 mmol) and acetonitrile (1 ml) was heated at 65° C. for 18 hours. The reaction mixture was cooled to room temperature, diluted with DCM and quenched with a 10% solution of potassium carbonate. The organic layer was decanted, dried over MgSO$_4$, filtered and evaporated to dryness. The residue was purified by high-performance liquid chromatography (X-Terra-C18 10 μm 19×150 mm mobile phase: NH$_4$HCO$_3$ 0.5%; Gradient from 40% to 100 of acetonitrile), yielding 24 mg (35%) of compound 5.

Example B6 a) Preparation of Compound 6

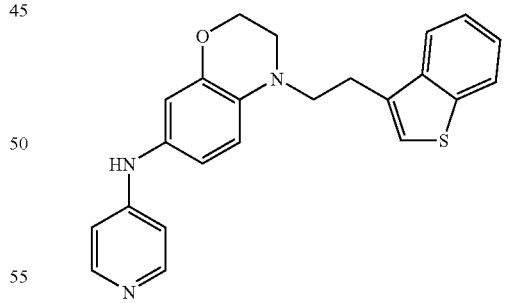

A mixture of intermediate 13 (0.000966 mol), 4-bromopyridine hydrochloride (0.00116 mol) and DIEA (0.000773 mol) in acetonitrile (3.3 ml) and EtOH (2.6 ml) was heated at 80° C. for 18 hours. The mixture was cooled to room temperature, quenched with a 10% solution of potassium carbonate and extracted with DCM. The organic layer was decanted, dried over MgSO$_4$, filtered and evaporated till dryness. The residue (0.36 g) was purified by high-performance liquid chromatography (Spherical SiOH 10 μm 60 g PharmPrep MERCK mobile phase: NH$_4$OH 0.2%; DCM 92% MeOH 8%). The pure fractions were collected and the solvent was evaporated. The residue (0.207 g) was crystallized from Et₂O and dried, yielding 0.161 g (43%) of compound 6.

b) Preparation of Compound 7

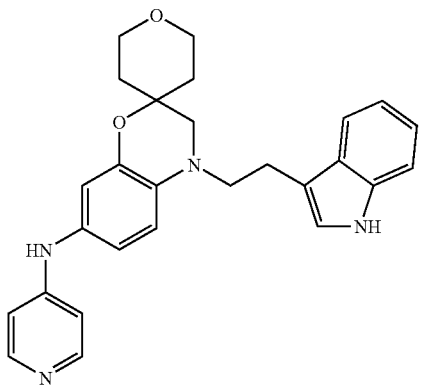

A mixture of intermediate 15 (see Example A3) (0.239 mmol), 4-bromopyridine hydrochloride (0.287 mmol) and DIEA (0.191 mmol) in acetonitrile (1 ml) and EtOH (0.8 ml) was heated at 65° C. for 18 hours. The reaction mixture was cooled to room temperature, diluted with EtOAc and quenched with a 10% solution of potassium carbonate. The organic layer was decanted, dried over MgSO₄, filtered and evaporated to dryness. The residue was purified by HPLC (H663-30 g SiO2 15/40 μm—eluent: DCM/MeOH/NH₄OH 95/5/0.5 then XBridge C18—eluent: CH₃CN/NH₄CO₃ 40/60 to CH₃CN 100). The pure fractions were collected and evaporated to dryness, yielding 40 mg (38%) of compound 7.

Example B7

Preparation of Compound 8

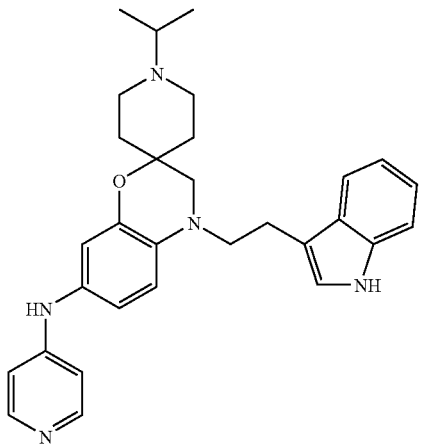

A mixture of intermediate 14 (see Example A3) (0.336 mmol) and 4-bromopyridine hydrochloride (0.403 mmol) in acetonitrile (2 ml) and EtOH (1.6 ml) was heated at 65° C. for 18 hours. The reaction mixture was cooled to room temperature, quenched with a 10% solution of potassium carbonate and extracted with DCM. The organic layer was decanted, dried over MgSO₄, filtered and evaporated to dryness. The residue was purified by HPLC(H693—XTerra MS C18 10 μm—eluent: CH₃CN/NH₄HCO₃ 0.5% 20/80 to CH₃CN 100). The pure fractions were collected and evaporated to dryness, yielding 58 mg (36%) of compound 8.

Example B8 a) Preparation of Compound 9

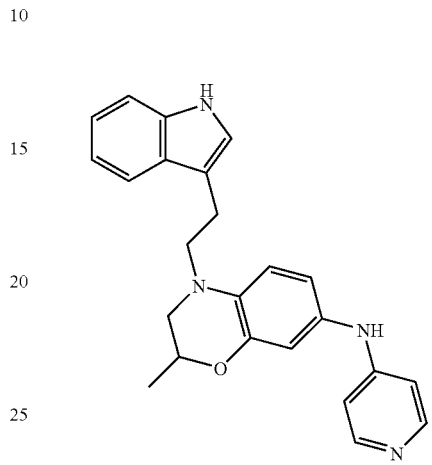

A mixture of intermediate 19 (0.0006 mol), 4-bromo-pyridine, hydrochloride (1:1) (0.0007 mol) and DIEA (0.0005 mol) in acetonitrile (20 ml) and EtOH (5 ml) was stirred at 65° C. overnight. Potassium carbonate 10% solution was added. The organic layer was extracted with EtOAc, dried (MgSO₄), filtered and the solvent was evaporated. The residue (0.6 g) was purified by column chromatography over silica gel (300 g) (eluent: DCM/MeOH/NH₄OH 92/8/1; 15-40 μm). The pure fractions were collected and the solvent was evaporated, yielding 0.192 g (77%) of compound 9.

b) Preparation of Compound 24

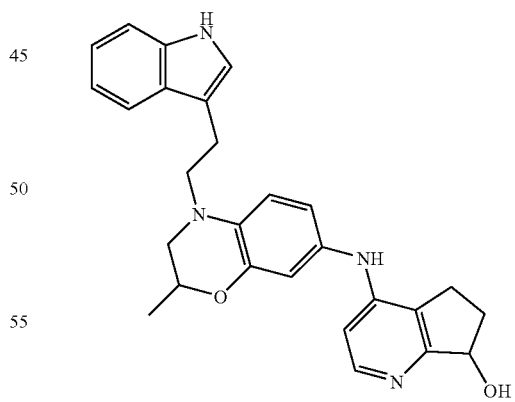

A mixture of intermediate 19 (0.00114 mol), 4-chloro-6,7-dihydro-5H-cyclopenta[b]pyridin-7-ol (0.00137 mol) and HCl 4M in dioxane (0.000228 mol) in acetonitrile (3.5 ml) and EtOH (2.8 ml) was heated at 80° C. overnight. The mixture was cooled to room temperature, quenched with a 10% solution of potassium carbonate and extracted with DCM. The organic layer was decanted, dried over MgSO₄, filtered and evaporated till dryness. The residue (0.56 g) was purified by high-performance liquid chromatography (Spherical SiOH 10 μm 60 g PharmPrep MERCK mobile phase: NH₄OH 0.5%; DCM 95% MeOH 5%). The pure fractions were collected and the solvent was evaporated. The residue (200 mg) was crystallized from Et₂O and dried, yielding 0.164 g (33%) of compound 24.

Example B9

Preparation of Compound 10

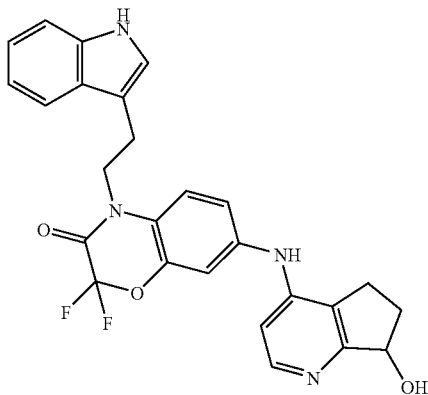

A mixture of intermediate 20 (0.0006 mol), 4-chloro-6,7-dihydro-5H-cyclopenta[b]pyridin-7-ol (0.0006 mol) and HCl/dioxane 4M (0.0002 mol) in acetonitrile/EtOH 4/1 (25 ml) was stirred at 65° C. overnight. The residue was purified by column chromatography over silica gel (eluent: DCM/MeOH/NH₄OH from 96/4/0.4 to 86/13/1.2; Sunfire 5 μm). The pure fractions were collected and the solvent was evaporated, yielding 0.073 g of compound 10.

Example B10 a) Preparation of Compound 11

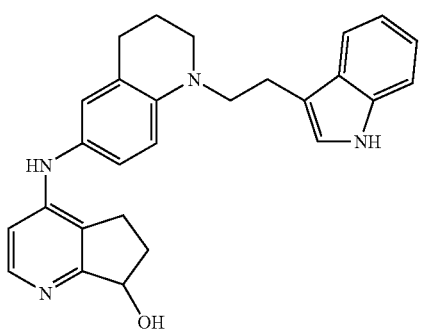

A mixture of intermediate 22 (0.68 mmol) 4-chloro-6,7-dihydro-5H-cyclopenta[b]pyridin-7-ol (0.816 mmol) and HCl/dioxane 4N (34 μl) in acetonitrile (3 ml) and EtOH (2.4 ml) was heated at 65° C. for 18 hours. The reaction mixture was quenched with a 10% solution of potassium carbonate and extracted with DCM. The organic layer was decanted, dried over MgSO₄, filtered and evaporated to dryness. The residue (321 mg) was purified by high-performance liquid chromatography (Spherical SiOH 10 μm 60 g PharmPrep MERCK mobile phase: NH₄OH 0.5%; DCM94% MeOH6%). The pure fractions were collected and the solvent was evaporated. The residue (124 mg) was crystallized from CH₃CN/DIPE. The precipitate was filtered off and dried, yielding 93 mg (32%) of compound 11.

b) Preparation of Compound 23

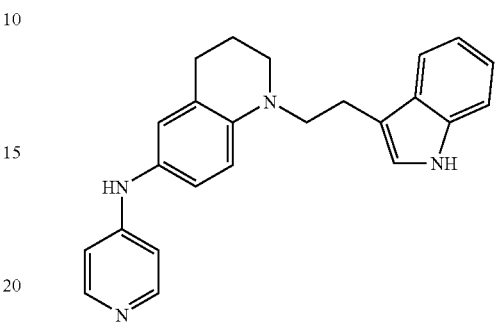

A mixture of intermediate 22 (0.68 mmol), 4-bromopyridine hydrochloride (0.748 mmol) and DIEA (0.544 mmol) in acetonitrile (3 ml) and EtOH (2.4 ml) was heated at 65° C. for 18 hours. The reaction mixture was quenched with a 10% solution of potassium carbonate and extracted with DCM. The organic layer was decanted, dried over MgSO₄, filtered and evaporated to dryness. The residue (250 mg) was purified by high-performance liquid chromatography (Spherical SiOH 10 μm 60 g PharmPrep MERCK mobile phase: NH₄OH 0.5%; DCM 92% MeOH 8%). The pure fractions were collected and the solvent was evaporated. The residue (147 mg) was crystallized from CH₃CN/DIPE. The precipitate was filtered off and dried, yielding 103 mg (41%) of compound 23.

Example B11

Preparation of Compound 12

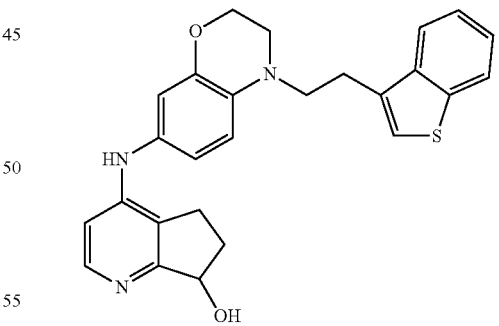

A mixture of intermediate 13 (0.000966 mol), 4-chloro-6,7-dihydro-5H-cyclopenta[b]pyridin-7-ol (0.00116 mol) and HC/dioxane 4M (0.000193 mol) in acetonitrile (3.3 ml) and EtOH (2.6 ml) was heated at 80° C. for 18 hours. The mixture was cooled to room temperature, quenched with a 10% solution of potassium carbonate and extracted with DCM. The organic layer was decanted, dried over MgSO₄, filtered and evaporated till dryness. The residue (0.48 g) was purified by high-performance liquid chromatography (Spherical SiOH 10 μm 60 g PharmPrep MERCK mobile phase: NH₄OH 0.1%; DCM 92% MeOH 8%). The pure fractions were collected and the solvent was evaporated. The residue (0.202 g) was crystallized from Et$_2$O and dried, yielding 0.139 g (32%) of compound 12.

Example B12

Preparation of Compound 13

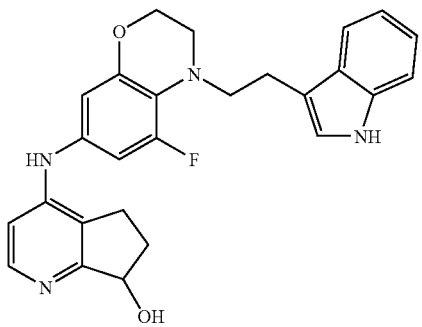

A mixture of intermediate 25 (0.228 mmol), 4-chloro-6,7-dihydro-5H-cyclopenta[b]pyridin-7-ol (0.274 mmol) and HCl/dioxane 4M (0.0456 mmol) in acetonitrile (1 ml) and EtOH (0.8 ml) was heated at 65° C. for 18 hours. The reaction mixture was cooled to room temperature, diluted with EtOAc and quenched with a 10% solution of potassium, carbonate. The organic layer was decanted, dried over MgSO$_4$, filtered and evaporated to dryness. The residue was purified by HPLC (H660—kromasil 3.5 μm—eluent: DCM/MeOH/NH$_4$OH 99/1/0.1 to 93/7/0.7). The pure fractions were collected and evaporated to dryness, yielding 77 mg (76%) of compound 13.

Example B13

Preparation of Compound 14

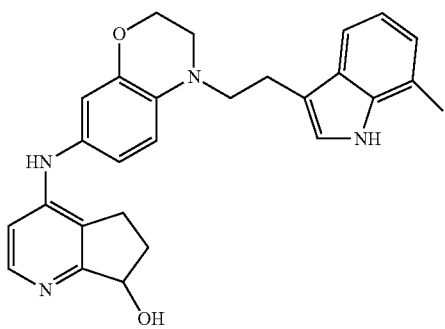

A mixture of 4-chloro-6,7-dihydro-5H-cyclopenta[b]pyridin-7-ol (0.00039 mol), HCl/dioxane 4M (0.0000651 mol) and intermediate 29 (0.000325 mol) in acetonitrile (1 ml) and EtOH (0.8 ml) was heated at 65° C. for 18 hours. The mixture was cooled to room temperature, quenched with a 10% solution of potassium carbonate and extracted with DCM. The organic layer was decanted, dried over MgSO$_4$, filtered and evaporated till dryness. The residue was purified by high-performance liquid chromatography over XTerra (eluent: CH$_3$CN/0.5% NaHCO$_3$: 30/70 to 100/0). The pure fractions were evaporated till dryness, yielding 0.013 g (8%) of compound 14.

Example B14 a) Preparation of Compound 15

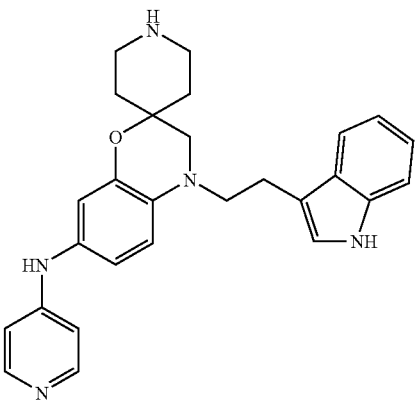

A mixture of intermediate 30 (0.236 mmol), 4-bromopyridine hydrochloride (0.283 mmol) and DIEA (0.189 mmol) in acetonitrile (1 ml) and EtOH (0.8 ml) was heated at 65° C. for 18 hours. The reaction mixture was cooled to room temperature and HCl 3N (0.5 ml) was added to complete the reaction at 65° C. for 18 hours. The reaction mixture was cooled to room temperature, diluted with DCM and quenched with a 10% solution of potassium carbonate. The organic layer was decanted, dried over MgSO$_4$, filtered and evaporated to dryness. The residue was purified by HPLC(H677—XTerra MSC18—eluent: CH$_3$CN/NH$_4$CO$_3$ 0.5% 20/80 to CH$_3$CN 100). The pure fractions were collected and evaporated to dryness, yielding 38 mg (37%) of compound 15.

b) Preparation of Compound 16

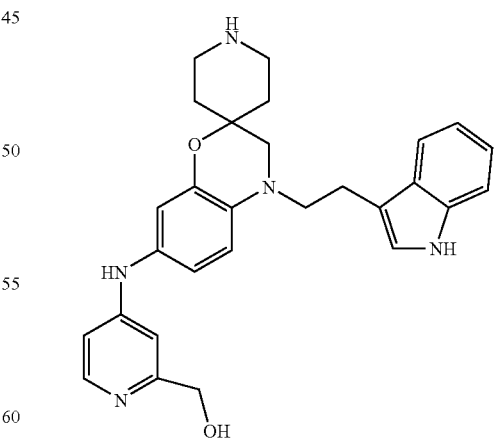

A mixture of intermediate 30 (0.236 mmol), 4-chloro-2-pyridinemethanol (0.283 mmol) and HCl/dioxane 4M (0.0471 mmol) in acetonitrile (1 ml) and EtOH (0.8 ml) was heated at 65° C. for 18 hours. The reaction mixture was cooled to room temperature and HCl 3N (0.5 ml) was added to complete the reaction at 65° C. for 18 hours. The reaction mixture was cooled to room temperature, diluted with DCM and quenched with a 10% solution of potassium carbonate. The organic layer was decanted, dried over MgSO$_4$, filtered and evaporated to dryness. The residue was purified by HPLC (H679—XTerra MSC18—eluent: CH$_3$CN/NH$_4$CO$_3$ 0.5% 20/80 to CH$_3$CN 100). The pure fractions were collected and evaporated to dryness, yielding 41 mg of (37%) of compound 16.

Example B15 a) Preparation of Compound 17

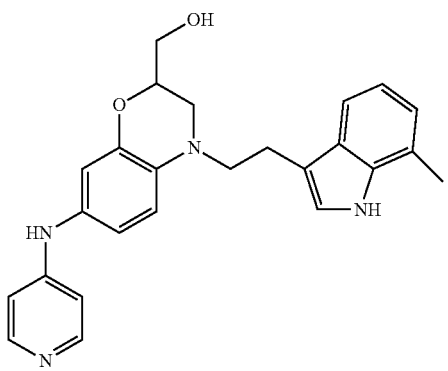

A mixture of intermediate 31 (0.465 mmol), 4-bromopyridine hydrochloride (0.511 mmol) and DIEA (0.372 mmol) in acetonitrile (2 ml) and EtOH (1.6 ml) was heated at 65° C. for 18 hours. The reaction mixture was cooled to room temperature, diluted with DCM and quenched with a 10% solution of potassium carbonate. The organic layer was decanted, dried over MgSO$_4$, filtered and evaporated to dryness. The residue was purified by Normal phase on (Cartridge 15-40 µm 30 g Mobile phase: 1% NH$_4$OH, 90% DCM, 10% MeOH). The pure fractions were collected and evaporated to dryness. The residue (107 mg) was taken up with DIPE, filtered and dried, yielding 70 mg (36%) of compound 17.

b) Preparation of Compounds 18 and 19 compound 18

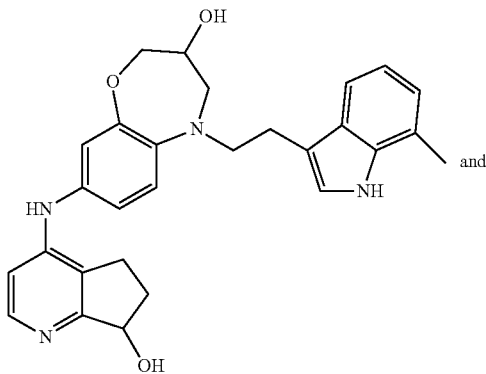

and compound 19

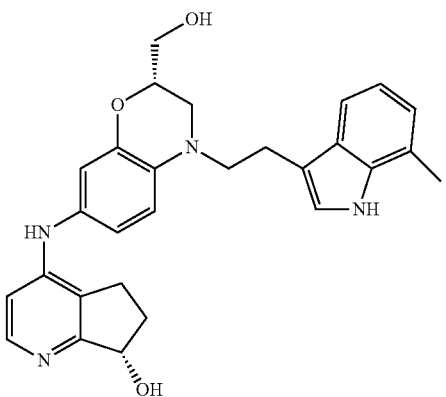

A mixture of intermediate 32 (0.274 mmol) and Tetra-n-butylammonium fluoride 1M in THF (0.274 mmol) in THF (2 ml) was stirred at room temperature overnight. The reaction mixture was quenched with a 10% solution of potassium carbonate and extracted with EtOAc. The organic layer was decanted, dried over MgSO$_4$, filtered and evaporated to dryness. The residue was purified by Normal phase on (Cartridge 15-40 µm 30 g mobile phase: 1% NH$_4$OH, 10% MeOH, 90% DCM) followed by Normal phase on (Stability 5 µm 150 30, Mobile phase: 0.3% NH$_4$OH, 3% MeOH, 97% DCM to 1.4/14/86)

The pure fractions were collected and evaporated to dryness, yielding 24 mg (12%) of compound 19 and 75 mg (37%) of compound 18.

Example B16

Preparation of Compound 20

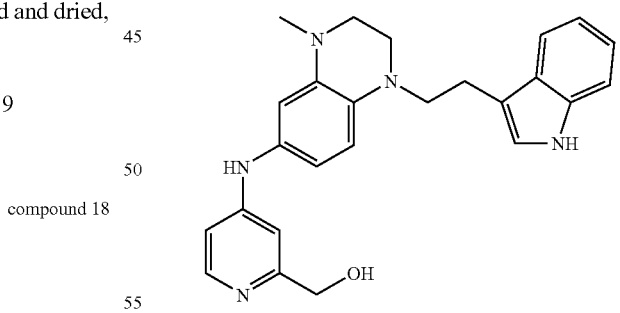

A mixture of intermediate 36 (0.692 mmol), 1H-Indole-3-acetaldehyde (1.383 mmol), sodium cyanotrihydroborate (0.934 mmol) and acetic acid (20 µl) in MeOH (3 ml) was stirred at room temperature for 18 hours. The reaction mixture was quenched with a 10% solution of potassium carbonate and extracted with DCM. The organic layer was decanted, dried over MgSO$_4$, filtered and evaporated to dryness. The residue (400 mg) was purified by high-performance liquid chromatography (X-Bridge-C18 5 µm 30*150 mm mobile phase: NH$_4$HCO$_3$ 0.5%; Gradient from 30% to 100% of CH₃CN). The pure fractions were collected and the solvent was evaporated, yielding 15 mg of compound 20.

Example B17

Preparation of Compound 22

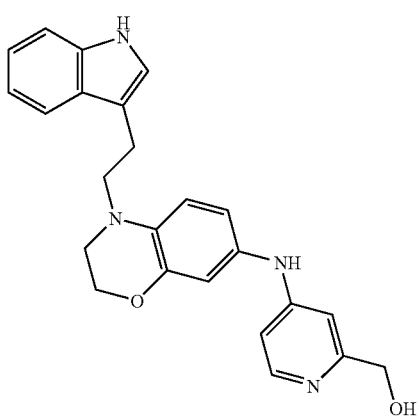

Compound 21 (0.0013 mol) was added portionwise at 0° C. to trihydro(tetrahydrofuran)boron (0.0062 mol). The mixture was stirred at 60° C. for one hour and 30 minutes, then poured out into water at 0° C. and filtered over celite. The organic layer was extracted with EtOAc, dried (MgSO₄), filtered and the solvent was evaporated in vacuo. The residue (0.55 g) was purified by column chromatography over silica gel (eluent: DCM/MeOH/NH₄OH from 98/2/0.2 to 88/11/1.1, Sunfire 5 μm). The pure fractions were collected and the solvent was evaporated, yielding 0.205 g (40%) of compound 22.

Table 3 lists the compounds that were prepared according to one of the above Examples (Ex.)

TABLE 3

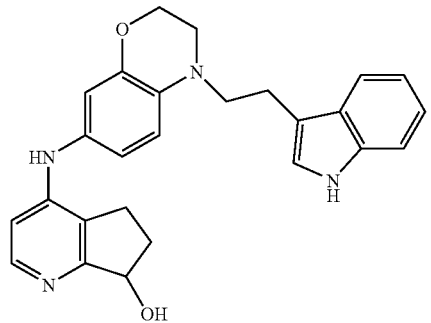

Co. No. 1; Ex. [B1]

TABLE 3-continued

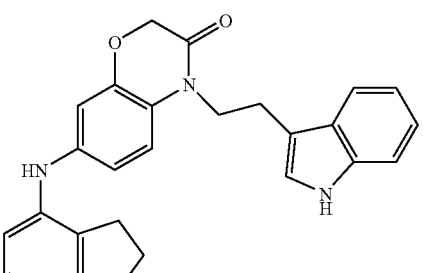

Co. No. 2; Ex. [B2]

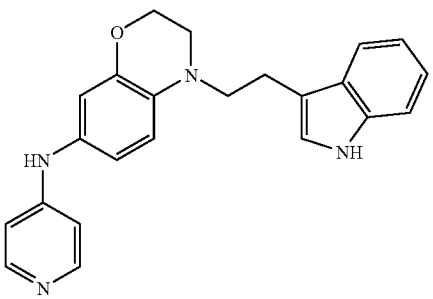

Co. No. 3; Ex. [B3]

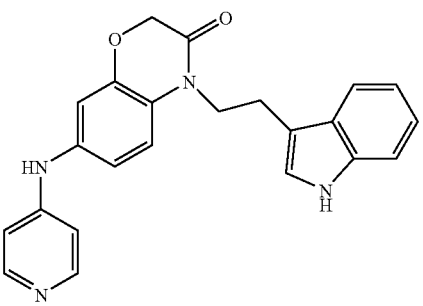

Co. No. 4; Ex. [B4]

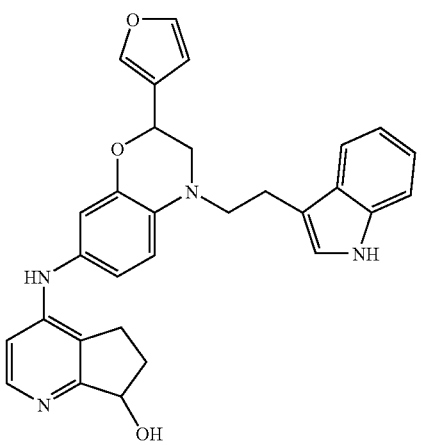

Co. No. 5; Ex. [B5]

TABLE 3-continued
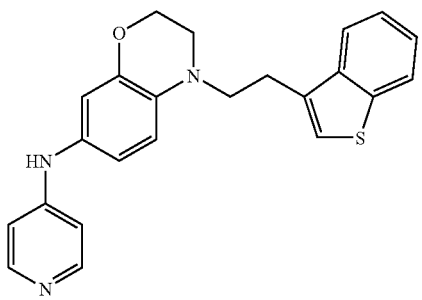
Co. No. 6; Ex. [B6], mp. 154° C.
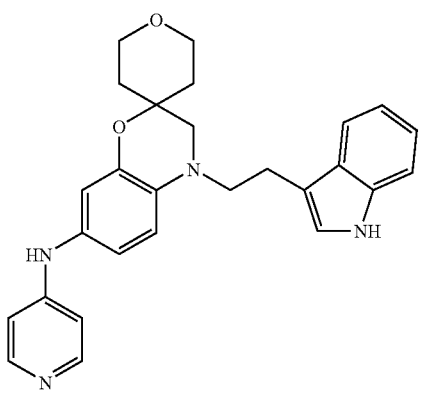
Co. No. 7; Ex. [B6b]
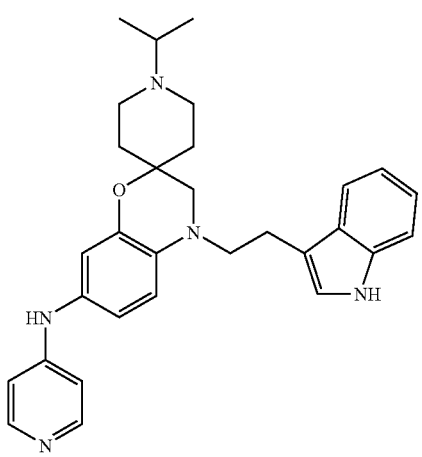
Co. No. 8; Ex. [B7]
TABLE 3-continued
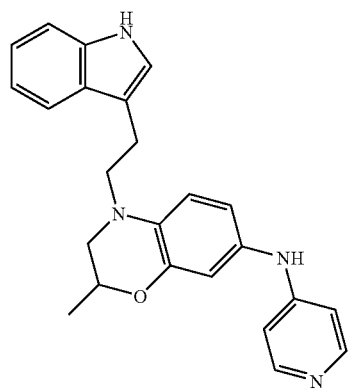
Co. No. 9; Ex. [B8a]
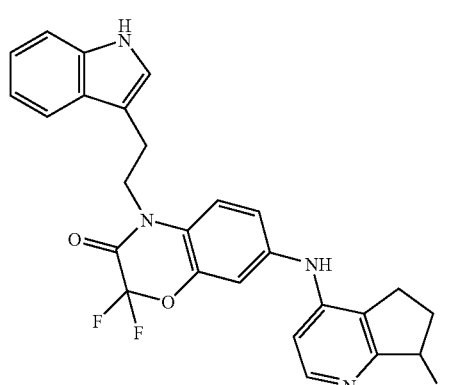
Co. No. 10; Ex. [B9], mp. 170° C.
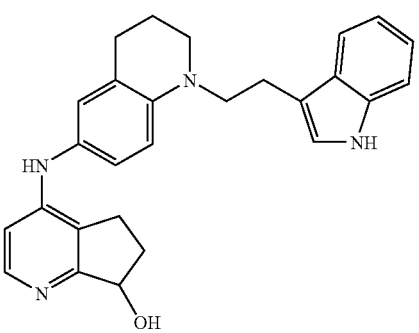
Co. No. 11; Ex. [B10a]; mp. 246° C.
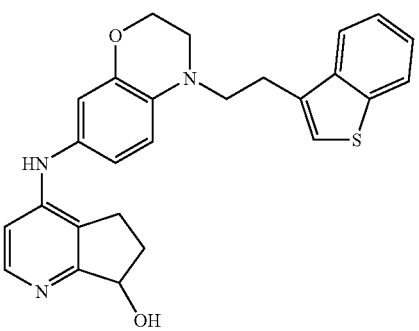
Co. No. 12; Ex. [B11], mp. 178° C.

TABLE 3-continued
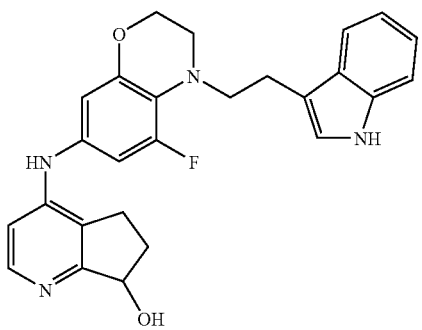
Co. No. 13; Ex. [B12], mp. 160° C.
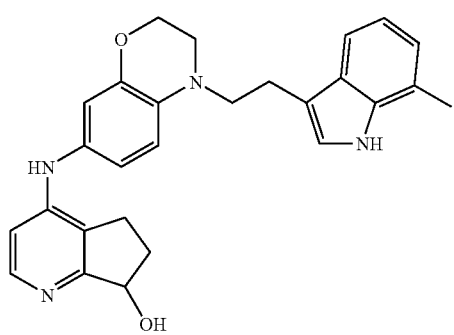
Co. No. 14; [Ex. B13]
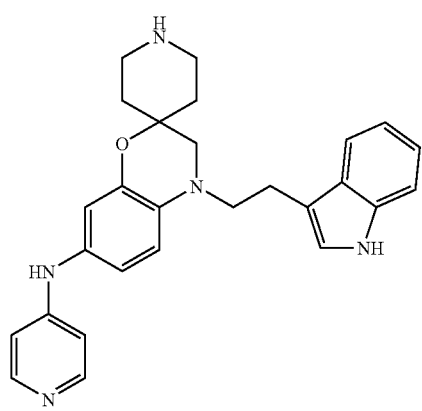
Co. No. 15; Ex. [B14a]
TABLE 3-continued
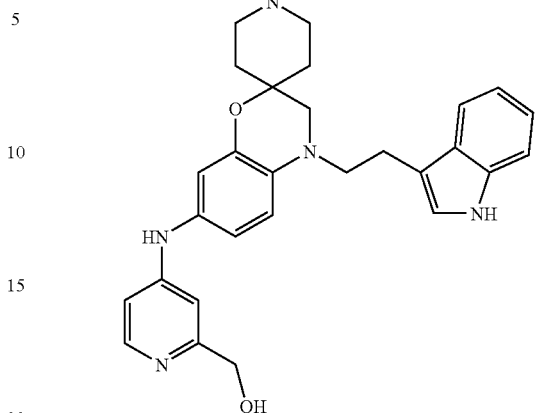
Co. No. 16; Ex. [B14b]
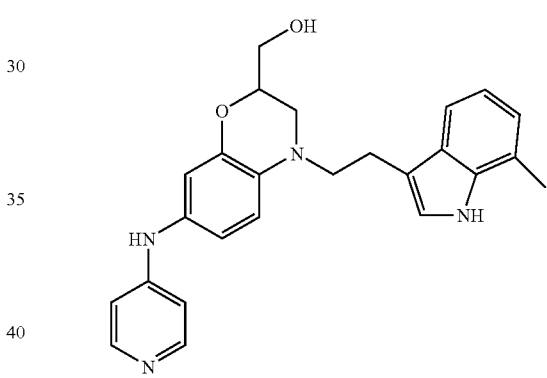
Co. No. 17; Ex. [B15a]; mp, 100° C. (gum)
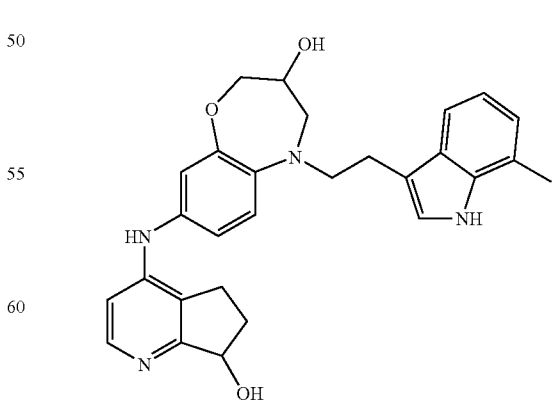
Co. No. 18; Ex. [B15b]

TABLE 3-continued
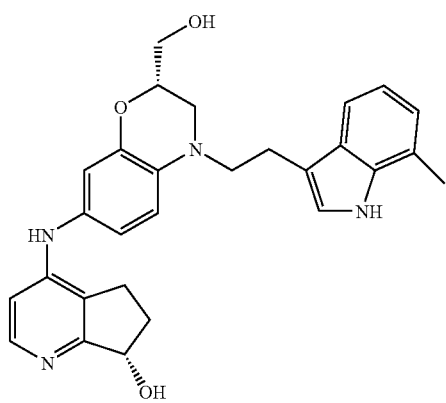
Co. No. 19; Ex. [B15b]
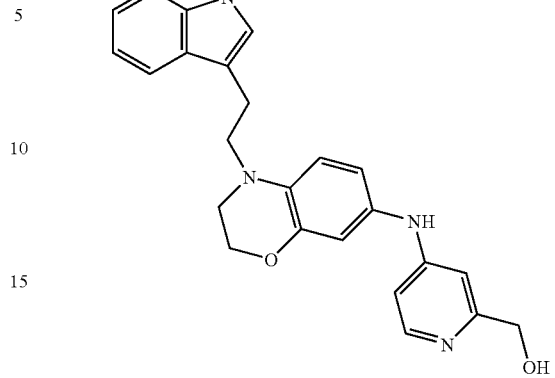
Co. No. 22; Ex. [B17]
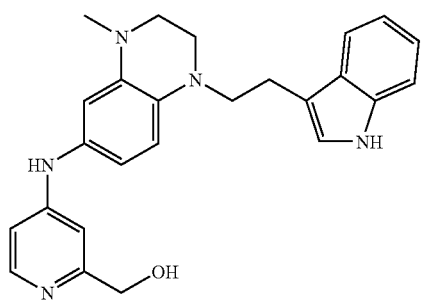
Co. No. 20; Ex. [B16]; mp. 128° C.
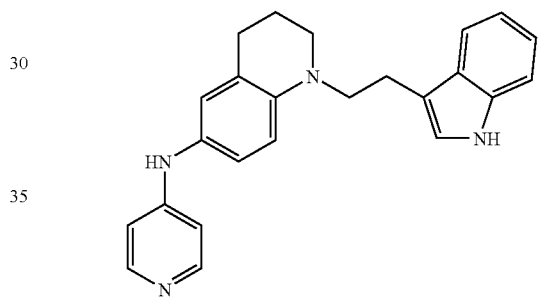
Co. No. 23; Ex. [B10b]; mp. 224° C.
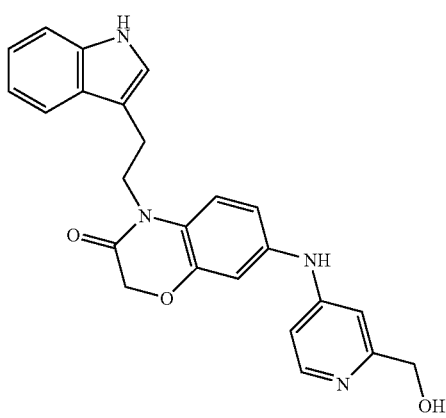
Co. No. 21; Ex. [B9]
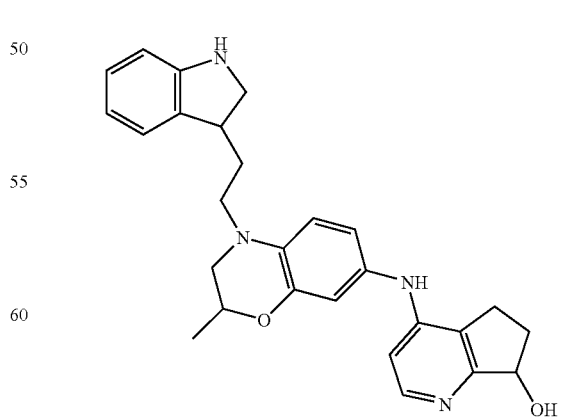
Co. No. 24; [B8b] and [B17]

TABLE 3-continued
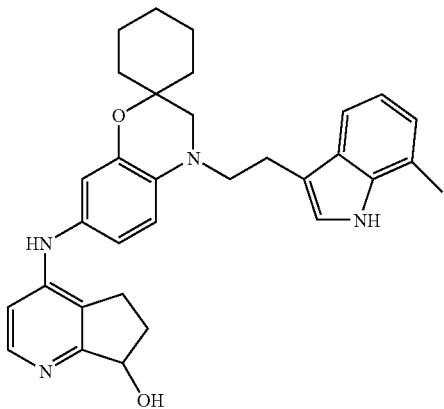
Co. No. 25; Ex. [B5]; mp. 250° C.
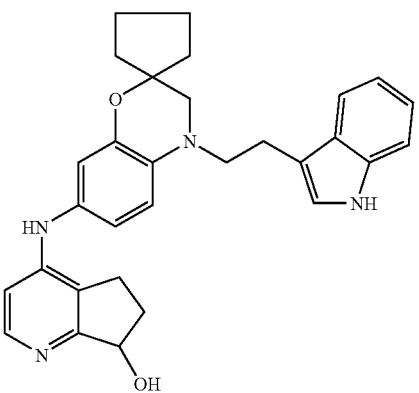
Co. No. 28; Ex. [B5]; mp. 240° C.
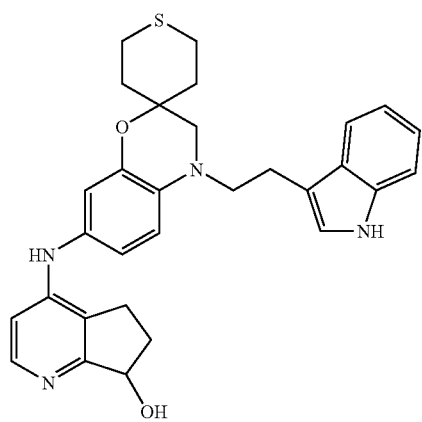
Co. No. 26; Ex. [B5]; mp. 215° C.
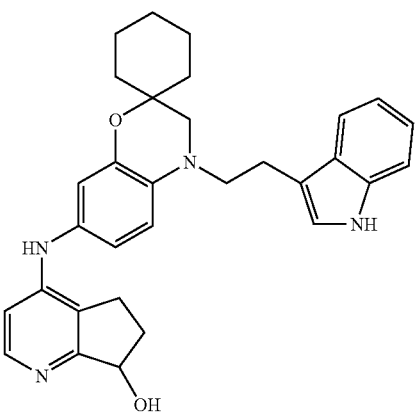
Co. No. 29; Ex. [B5]
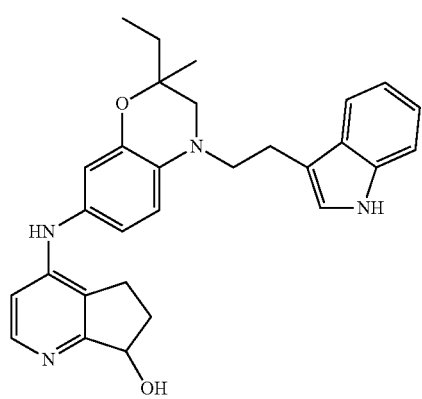
Co. No. 27; Ex. [B5]; mp. 190° C.
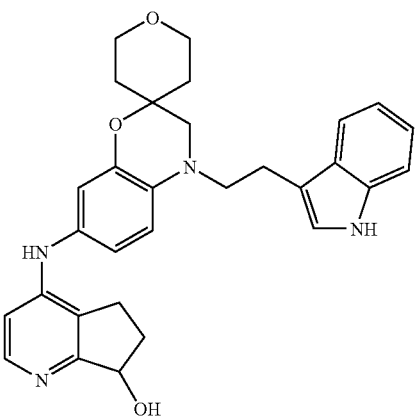
Co. No. 30; Ex. [B5]; mp. 140° C. (gum)

TABLE 3-continued
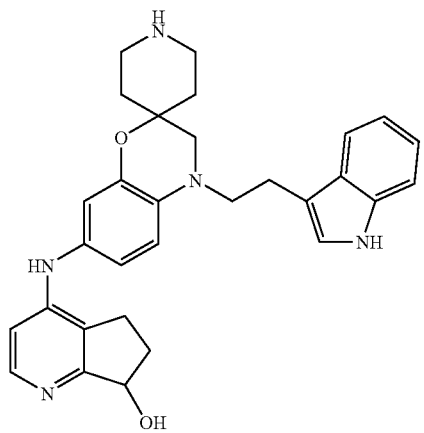
Co. No. 31; Ex. [B5]
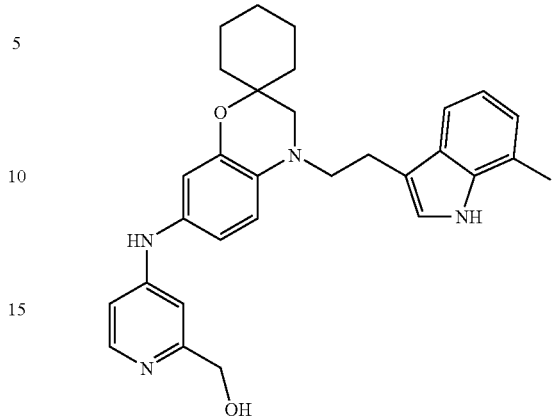
Co. No. 34; Ex. [B5]
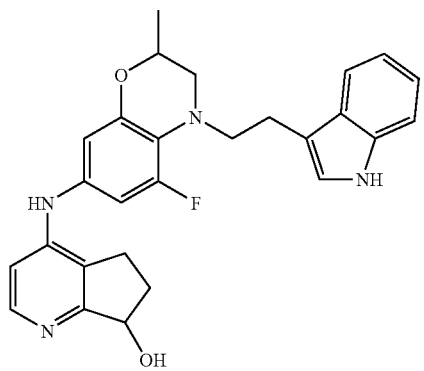
Co. No. 32; Ex. [B5]; mp. 140° C.
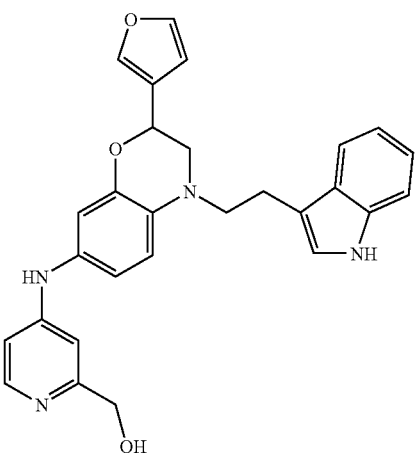
Co. No. 35; Ex. [B5]
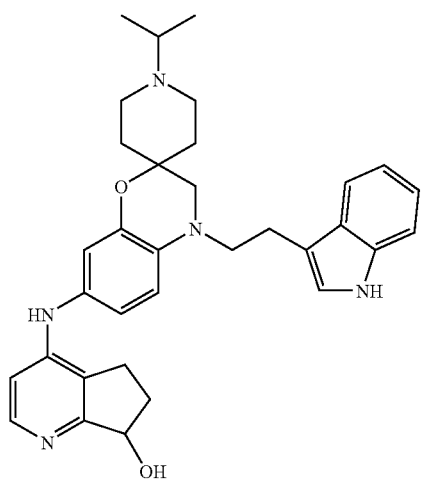
Co. No. 33; Ex. [B5]
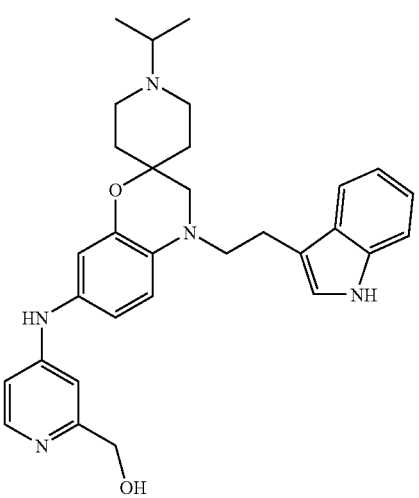
Co. No. 36; Ex. [B5]

TABLE 3-continued
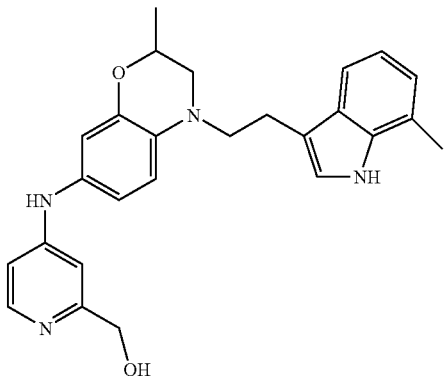
Co. No. 37; Ex. [B5]; mp. 126° C.
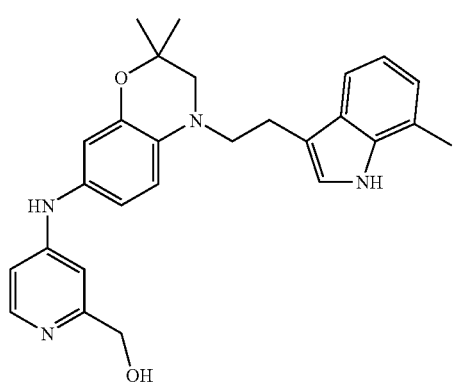
Co. No. 38; Ex. [B5]; mp. 165° C.
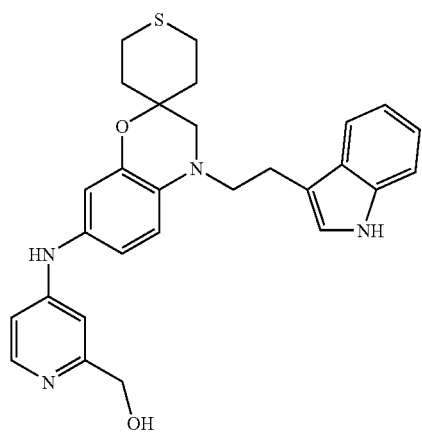
Co. No. 39; Ex. [B5]
TABLE 3-continued
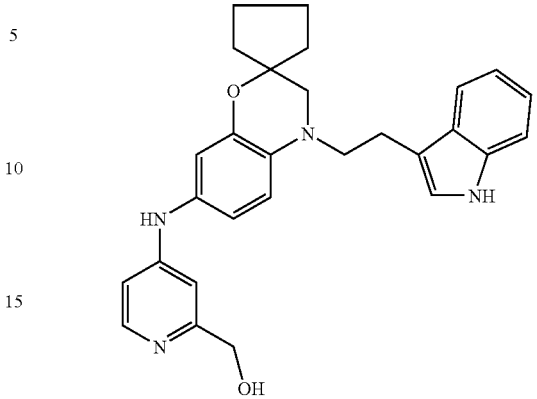
Co. No. 40; Ex. [B5]; mp. 120° C. (gum)
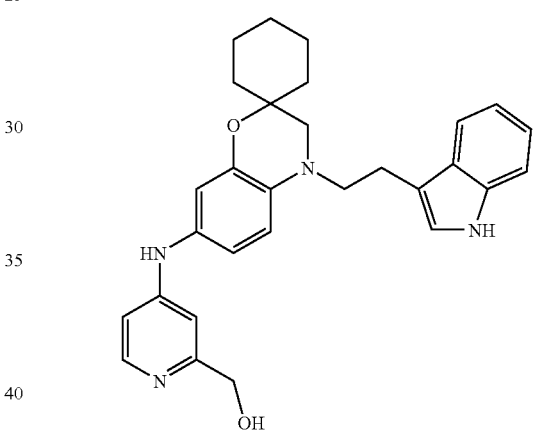
Co. No. 41; Ex. [B5]
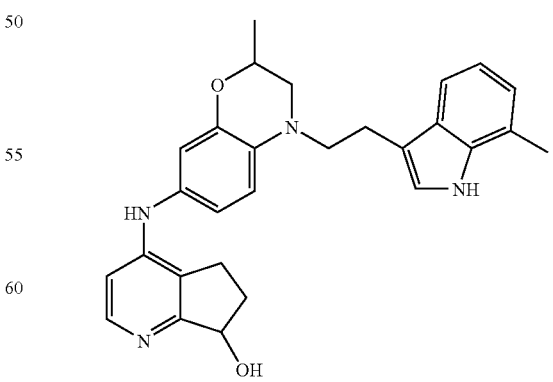
Co. No. 42; Ex. [B5], mp. 227° C.

TABLE 3-continued
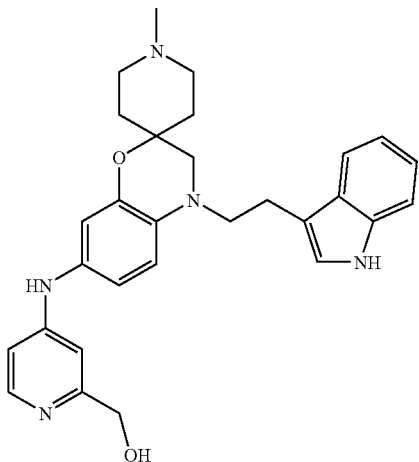
Co. No. 43; Ex. [B5]
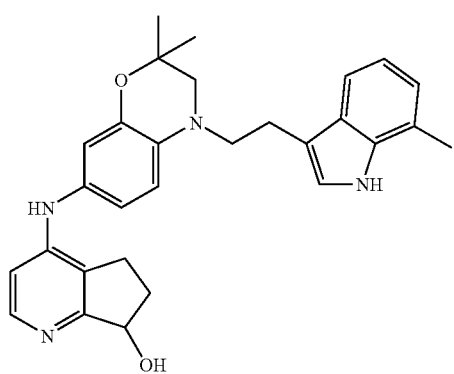
Co. No. 44; Ex. [B5], mp. 233° C.
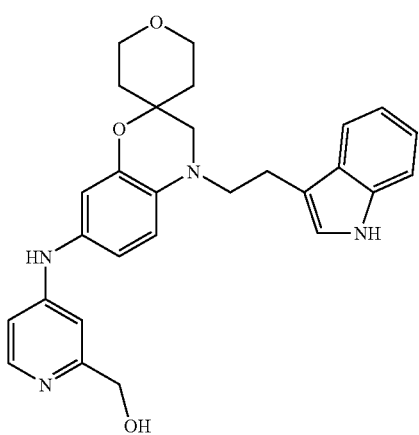
Co. No. 45; Ex. [B5]; mp. 221° C.
TABLE 3-continued
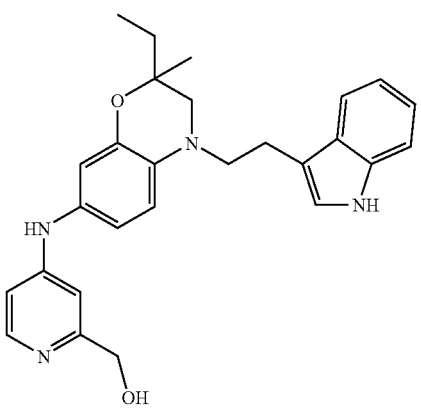
Co. No. 46; Ex. [B5]; mp. 161° C.
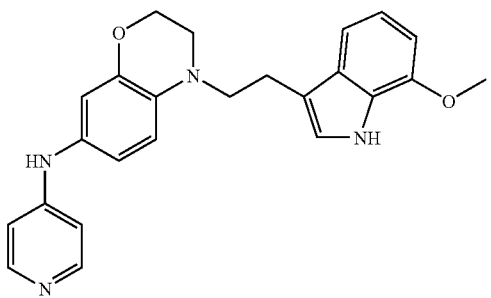
Co. No. 47; Ex. [B6a]; mp. 95° C. (gum)
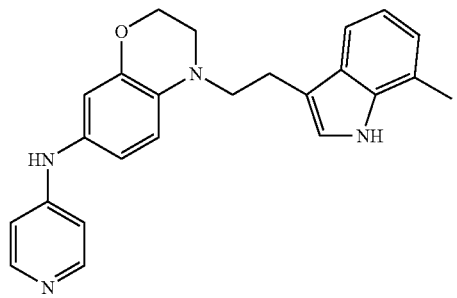
Co. No. 48; [Ex. B6a]
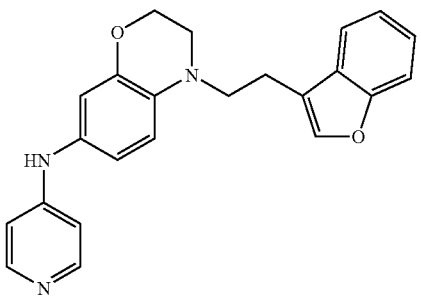
Co. No. 49; Ex. [B6a]

TABLE 3-continued
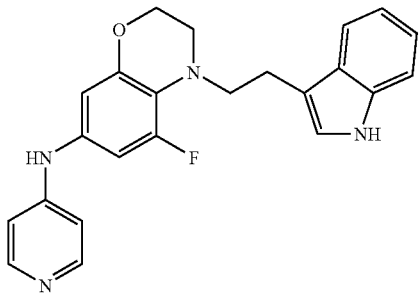
Co. No. 50; Ex. [B6a], mp. 209° C.
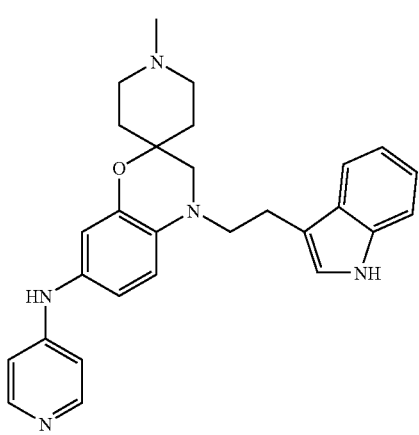
Co. No. 51; Ex. [B6b]
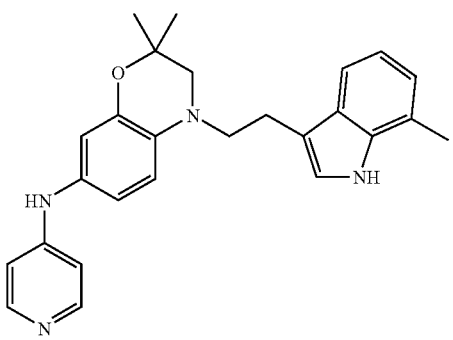
Co. No. 52; Ex. [B6b], mp. 165° C.
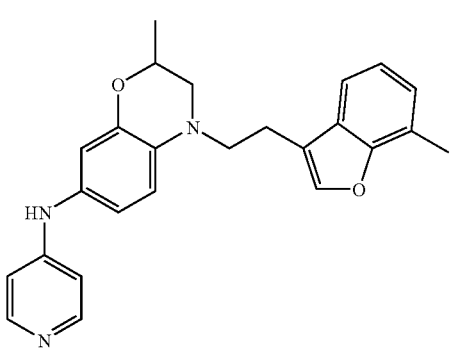
Co. No. 53; Ex. [B6b]; mp. 201° C.
TABLE 3-continued
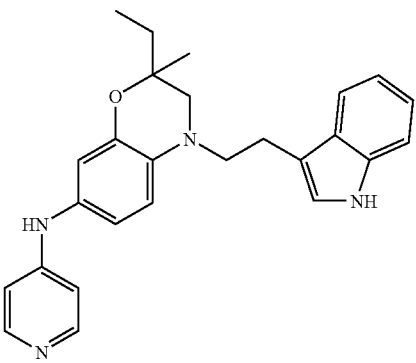
Co. No. 54; Ex. [B6b]; mp. 170° C.
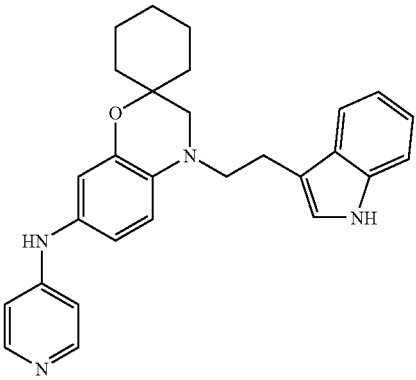
Co. No. 55; Ex. [B6b]
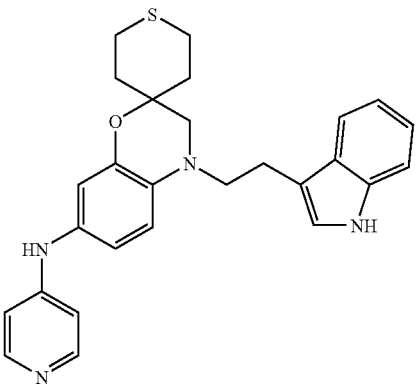
Co. No. 56; Ex. [B6b]
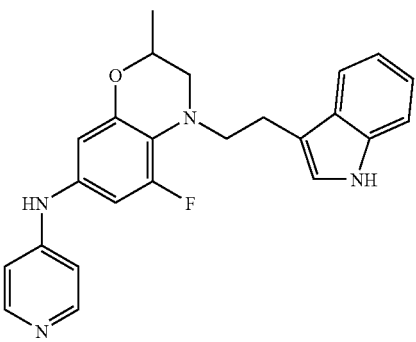
Co. No. 57; Ex. [B6b]

TABLE 3-continued
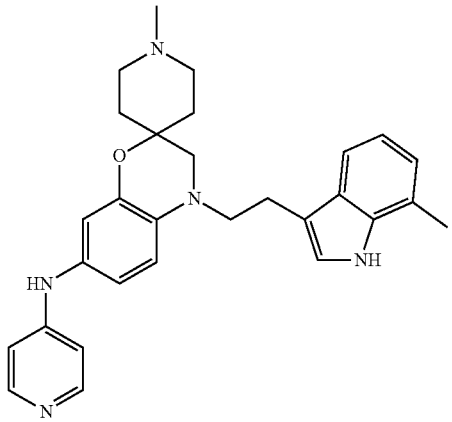
Co. No. 58; Ex. [B6b]
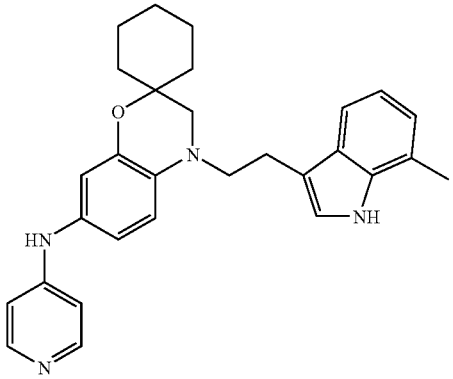
Co. No. 59; Ex. [B6b]
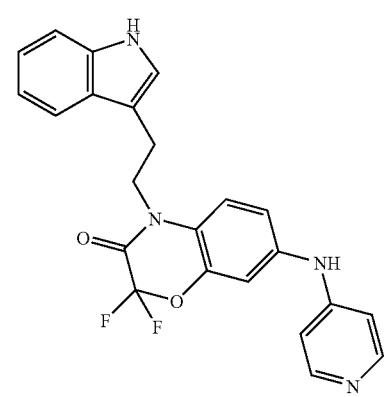
Co. No. 60; Ex. [B8a]
TABLE 3-continued
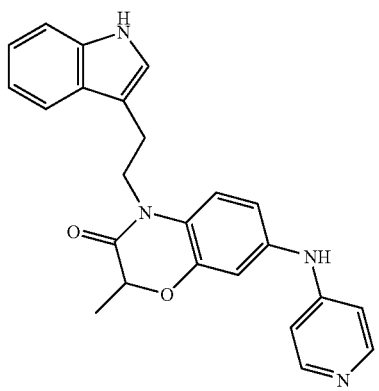
Co. No. 61; Ex. [B8a]
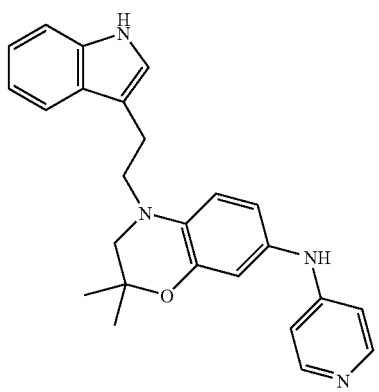
Co. No. 62; Ex. [B8a]
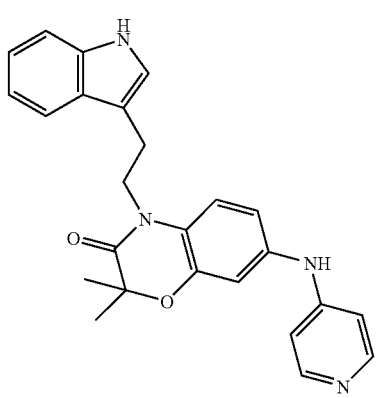
Co. No. 63; Ex. [B8a]

TABLE 3-continued
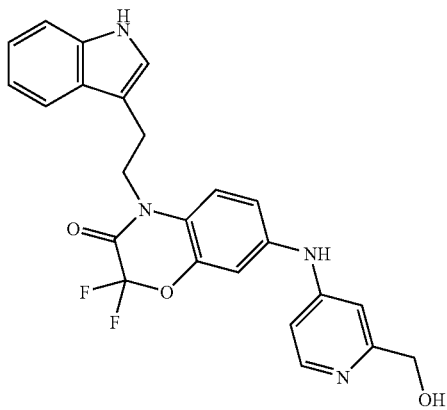
Co. No. 64; Ex. [B9]
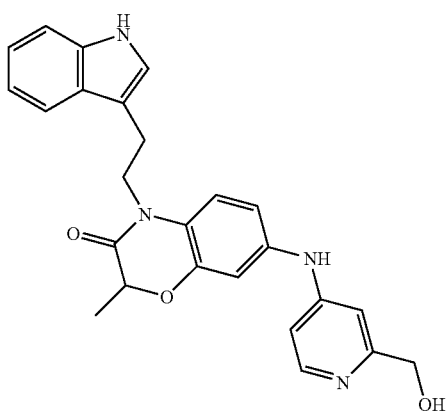
Co. No. 65; Ex. [B9]
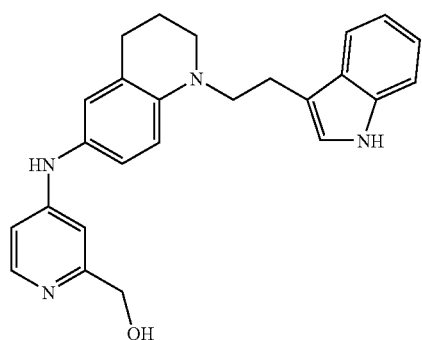
Co. No. 66; [Ex. B10a]; mp. 158° C.
TABLE 3-continued
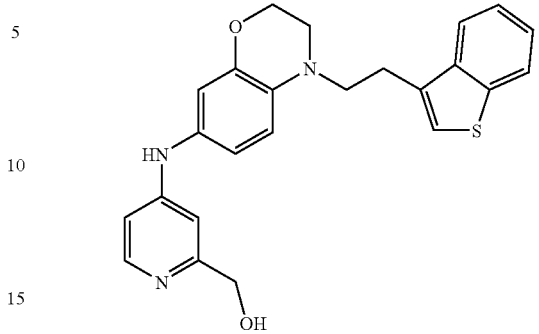
Co. No. 67; [Ex. B11], MP. 170° C.
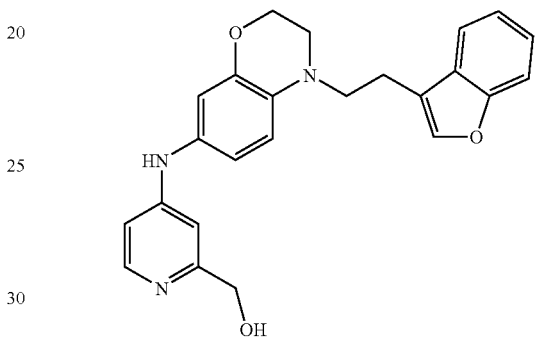
Co. No. 68; [Ex. B11]
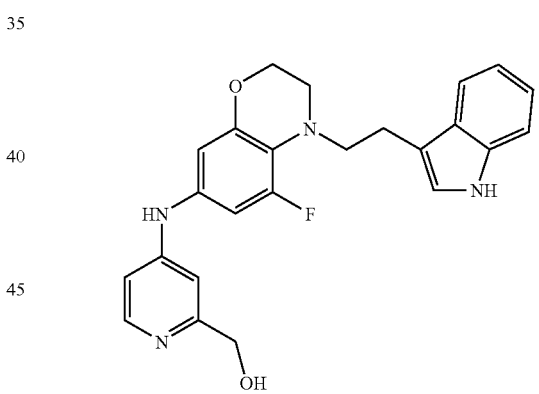
Co. No. 69; [Ex. B11]
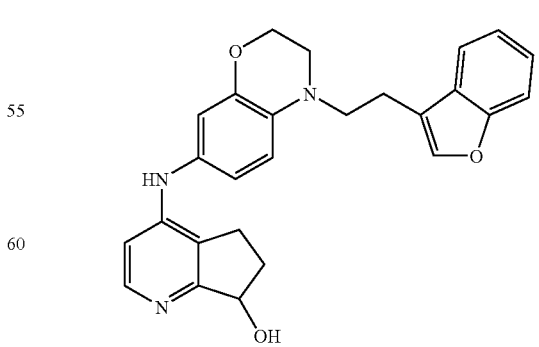
Co. No. 70; Ex. [B11]

TABLE 3-continued
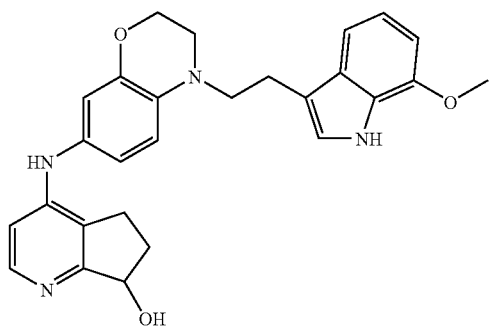
Co. No. 71; Ex. [B.12], mp. 136° C. (gum)
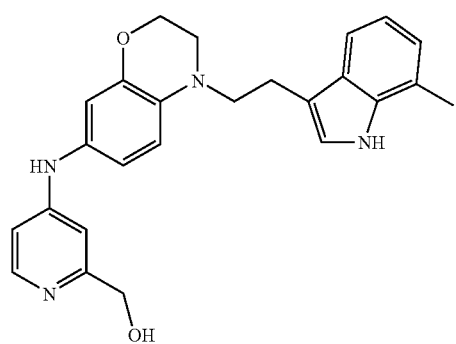
Co. No. 72; Ex. [B13]
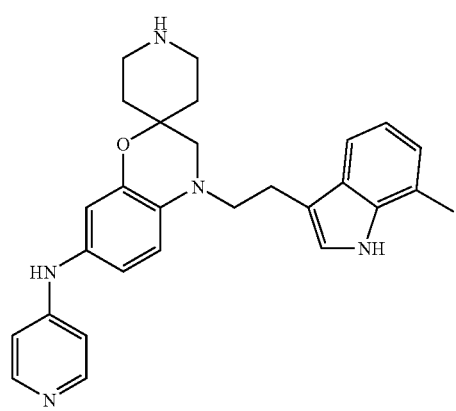
Co. No. 73; Ex. [B14a], mp. 110° C. (gum)
TABLE 3-continued
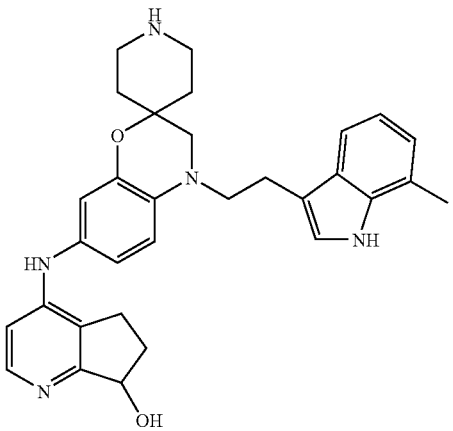
Co. No. 74; Ex. [B14b], mp. 212° C.
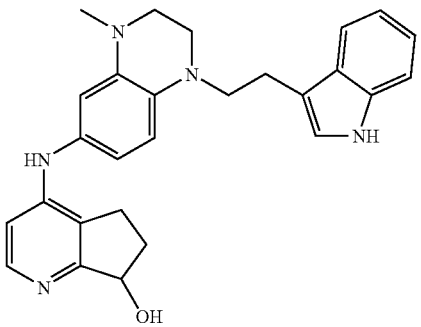
Co. No. 75; Ex. [B16], mp. 114° C. (gum)
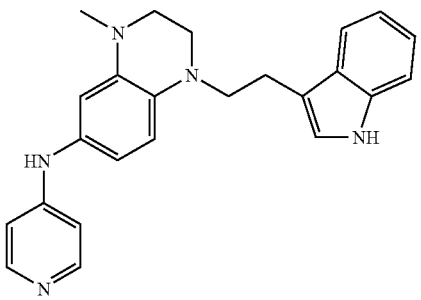
Co. No. 76; Ex. [B16]
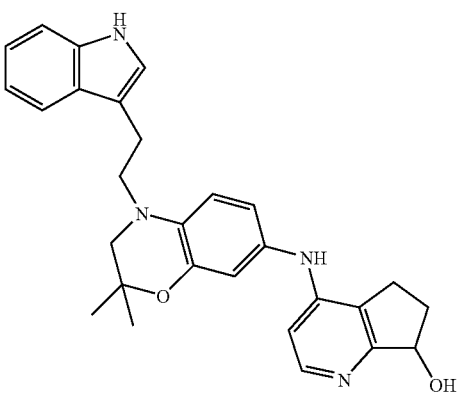
Co. No. 77; Ex. [B17]

TABLE 3-continued

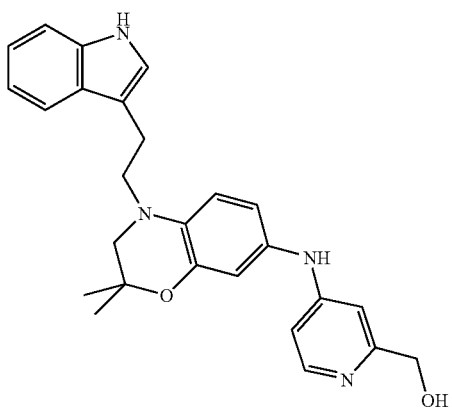

Co. No. 78; Ex. [B17]

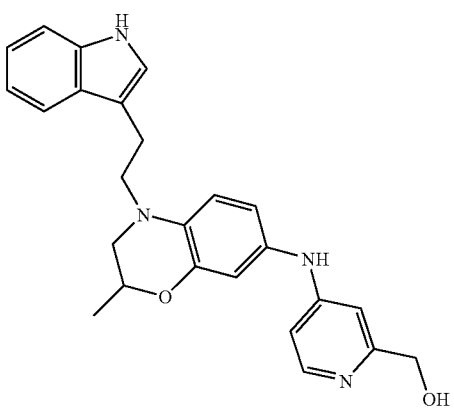

Co. No. 79; Ex. [B17]

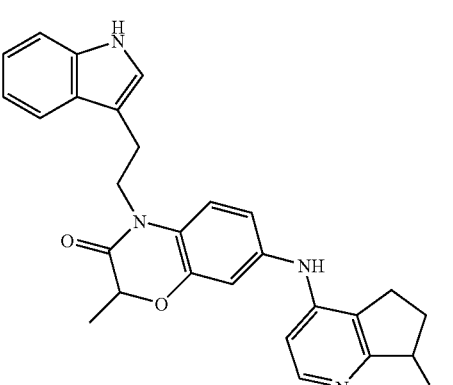

Co. No. 80; Ex. [B9]

TABLE 3-continued

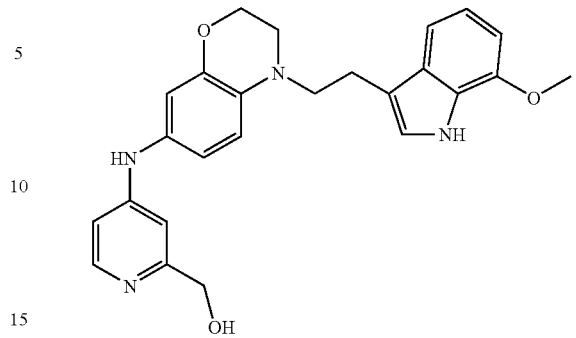

Co. No. 81; Ex. [B11]

C. Pharmacological Example

A2780 cells are human ovarian carcinoma cells with wild type p53.

The capacity of the compounds to preserve p53 in A2780 cells was measured with the p53 enzyme linked immunosorbent assay (ELISA). The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bound by horseradish peroxidase-conjugated streptavidin. The horseradish peroxidase catalyses the conversion of the chromogenic substrate o-phenylene diamine, the intensity of which is proportional to the amount of p53 protein bound to the plate. The coloured reaction product is quantified using a spectrophotometer. Quantitation is achieved by the construction of a standard curve using known concentrations of purified recombinant HIS tagged p53 protein (see example C.1).

Cellular activity of the compounds of formula (I) was determined on A2780 tumour cells using a colorimetric assay for cell toxicity or survival (see example C.2).

C.1 p53 ELISA

A2780 cells (ATCC) were cultivated in RPMI 1640 supplemented with 10% fetal calf serum (FCS), 2 mM L-glutamine and gentamycin at 37° C. in a humidified incubator with 5% $CO_2$.

A2780 cells were seeded at 20.000 cells per well in a 96 well plate, cultured for 24 hours and treated with compound for 16 hours at 37° C. in a humidified incubator. After incubation, the cells were washed once with phosphate-buffered saline and 30 μl, per well, low salt RIPA buffer (20 mM tris, pH7.0, 0.5 mM EDTA, 1% Nonidet P40, 0.5% DOC, 0.05% SDS, 1 mM PMSF, 1 μg/ml aprotinin and 0.5 μ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb1801 (Abcam ab28-100) at a concentration of 1 μg/ml in coating buffer (0.1 M NaHCO₃ pH8.2), 50 μl per well. The antibody was allowed to adhere overnight at 4° C. Coated plates were washed once with phosphate-buffered saline (PBS)/0.05%

Tween 20 and 300 µl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS/0.05% Tween 20 and blocking buffer or standards were added at 80 µl/well. To the standards, 20 µl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% $H_2O_2$ to 25 ml OPD buffer: 35 mM citric acid, 66 mM $Na_2HPO_4$, pH5.6). After 5 to 10 minutes, colour reaction was stopped by adding 50 µl stop buffer (1 M $H_2SO_4$) per well. The absorbance at dual wavelengths of 490/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 140% was defined as significant. Herein the effects of test compounds are expressed as the lowest dose giving at least 140% of the value for p53 present in the control (LAD) (see Table 4 below).

In some of the experiments the assay was adapted for and used in 384-well culture plates C.2 Proliferation Assay The human A2780 ovarian cancer cells were a kind gift from Dr. T. C. Hamilton (Fox Chase Cancer Centre, Pennsylvania, U.S.A.). The cells were cultured in RPMI 1640 medium supplemented with 2 mM L-Glutamine, 50 µg/ml gentamicin and 10% fetal calf serum.

Reagents Used in the Alamar Blue Assay

Resazurin was purchased from Aldrich (Prod. No. 199303). Potassium ferrocyanide, potassium ferricyanide, $KH_2PO_4$ and $K_2HPO_4$ were purchased from Sigma (Prod. Nos. P9387, P8131, P5655 and P8281, respectively).

Potassium Phosphate Buffer 0.1 M (PPB) was made as follows: 2.72 gram $KH_2PO_4$ and 13.86 gram $K_2HPO_4$ were dissolved in 500 ml milli-Q $H_2O$, the pH was adjusted to pH 7.4 and the volume was brought to 1 liter with milli-Q $H_2O$; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20× (vol/vol) in PPB and filter sterilising; the Alamar Blue solution could be kept at 4° C. for a maximum of 2 weeks.

Procedure of the Alamar Blue assay

For experiments in 384 wells plates the cells were seeded at a density of $5 \times 10^3$ cells/ml in Falcon 384-well culture plates (Life Technologies, Merelbeke, Belgium), black with clear bottom, in 45 µl culture medium. Cells were allowed to adhere to plastic for 24 hr. The tested compound was pre-diluted (1/50 in culture medium) and 5 µl pre-diluted compound was added to the wells. Following 4-day incubation, 10 µl of the Alamar Blue solution was added to each well and the cells were further incubated for 5 hrs (A2780) at 37° C. The fluorescence intensity was measured for each well with a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value) (see Table 4).

TABLE 4

Results of the compounds that were tested in the above p53 ELISA protocol (LAD) and proliferation assay ($pIC_{50}$)

| Comp. No. | p53-elisa LAD [microM] | $pIC_{50}$ |
|---|---|---|
| 1 | 0.1 | 6.37 |
| 2 | 1 | ~5.22 |
| 3 | >10.0 | <5.0 |
| 4 | >10.0 | <5.0 |
| 5 | 0.3 | 5.59 |
| 6 | >10.0 | 5.26 |
| 7 | >10.0 | 5.07 |
| 8 | >10.0 | 5.9 |
| 9 | >10.0 | ~5.23 |
| 10 | 0.3 | — |
| 11 | 0.1 | 5.63 |
| 12 | 0.3 | 5.43 |
| 13 | 1 | 5.35 |
| 14 | 3 | 5.54 |
| 15 | >10.0 | 5.08 |
| 16 | >10.0 | <5 |
| 17 | >10.0 | — |
| 18 | >10 | — |
| 19 | >10 | — |
| 20 | 3 | 5.32 |
| 21 | >10.0 | <5 |
| 22 | 1 | 5.64 |
| 23 | >10.0 | 5.52 |
| 24 | 3 | 5.25 |
| 25 | 0.03 | ~5.25 |
| 26 | 0.03 | ~5.22 |
| 27 | 1 | 5.29 |
| 28 | 3 | 5.31 |
| 29 | 10 | ~5.29 |
| 30 | >10.0 | 5.2 |
| 31 | >10.0 | <5 |
| 32 | 3 | — |
| 33 | >10.0 | 5.66 |
| 34 | 0.3 | 5.36 |
| 35 | 3 | ~5.29 |
| 36 | >10.0 | 5.47 |
| 37 | >10.0 | 5.45 |
| 38 | >10.0 | 5.43 |
| 39 | >10.0 | ~5.32 |

TABLE 4-continued

Results of the compounds that were tested in the above p53 ELISA protocol (LAD) and proliferation assay (pIC$_{50}$)

| Comp. No. | p53-elisa LAD [microM] | pIC$_{50}$ |
|---|---|---|
| 40 | >10.0 | ~5.32 |
| 41 | >10.0 | ~5.32 |
| 42 | >10.0 | 5.32 |
| 43 | >10.0 | ~5.30 |
| 44 | >10.0 | 5.3 |
| 45 | >10.0 | 5.2 |
| 46 | >10.0 | 5.16 |
| 47 | >10.0 | ~5.19 |
| 48 | >10.0 | 5.46 |
| 49 | >10.0 | 5.32 |
| 50 | >10.0 | 5.09 |
| 51 | >10.0 | 5.52 |
| 52 | >10.0 | 5.51 |
| 53 | >10.0 | 5.46 |
| 54 | >10.0 | 5.44 |
| 55 | >10.0 | 5.43 |
| 56 | >10.0 | ~5.32 |
| 57 | >10.0 | — |
| 58 | >10.0 | — |
| 59 | >10.0 | 5.61 |
| 60 | >10.0 | — |
| 61 | >10.0 | <5 |
| 62 | >10.0 | 5.27 |
| 63 | >10.0 | <5 |
| 64 | 10 | — |
| 65 | >10.0 | <5 |
| 66 | 3 | 5.85 |
| 67 | 10 | 5.3 |
| 68 | >10.0 | 5.28 |
| 69 | 10 | <5 |
| 70 | 10 | 5.19 |
| 71 | >10.0 | 5.28 |
| 72 | >10.0 | 5.33 |
| 73 | >10.0 | — |
| 74 | >10.0 | — |
| 75 | >10.0 | ~5.28 |
| 76 | 10 | 5.48 |
| 77 | 3 | 5.66 |
| 78 | >10.0 | 5.21 |
| 79 | 10 | — |
| 80 | — | 5.51 |
| 81 | >10.0 | 5.38 |

~: means approximate

D. Analytical Data

General Procedure A

The HPLC measurement was performed using a system comprising a Dionex P580LPG quaternary gradient pump, a TSP (Thermo Separation)- or Gilson ASPEC auto sampler, a Dionex UVD340S diode-array detector (DAD) or a TSP dual wavelengths UV-detector and a column as specified in the respective methods below. The column temperature was room temperature. The chromatography data system was Chromeleon Vs. 6.60 or higher.

Mass detection was done by Flow injection analysis (FIA) (e.g. MeOH, 0.2% formic acid) on a Thermo Finnigan AQA™ or Thermo Finnigan MSQ™ plus mass spectrometer. Ionisation was APCI+ (atmospheric pressure chemical ionization). Typically, measurements were done at 3-4 cone voltages simultaneously. The cone voltage was modified during the measurement in short intervals e.g. for Thermo Finnigan AQA™ at 5, 15 and 30 V and e.g. for the Thermo Finnigan MSQ™ plus at 40, 50 and 70 V, alternating within ca. 0.3 seconds. The APCI probe temperature was 350° C. Mass spectra were acquired by scanning from 100 to 800 within 2.5 seconds. Nitrogen was used as the nebulizer gas.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for LCMS method 2), and 3.15 kV at 110° C. on the ZQ™ (simple quadrupole Zspray™ mass spectrometer from Waters—for LCMS method 5). Nitrogen was used as the nebulizer gas. Data acquisition was performed with a Waters-Micromass MassLynx-Openlynx data system.

General Procedure C

The LC measurement was performed using a HPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

LCMS Method 1

In addition to general procedure A: Reversed phase HPLC was carried out on a Develosil RPAq column (4.6×50 mm) with a flow rate of 1.5 ml/min. UV-detection at 220 nm and 254 nm. A linear gradient run was employed from 10% acetonitrile and 90% water (0.1% TFA) to 100% acetonitrile in 5 minutes and hold for 1 minute.

LCMS Method 2

In addition to the general procedure B: Reversed phase HPLC was carried out on a Xterra-MS C18 column (5 µm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

LCMS Method 3

In addition to the general procedure C: Reversed phase HPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

LCMS Method 4

In addition to the general procedure C: Reversed phase HPLC was carried out on a Waters HSS (High Strength Silica) C18 column (1.8 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltages were 20, 30, 45, 60 V for positive ionization mode. Mass spectra were acquired by scanning from 100 to 1000 in 0.2 seconds using an interscan delay of 0.1 seconds.

LCMS Method 5

In addition to the general procedure B: Reversed phase HPLC was carried out on a Xterra-MS C18 column (3.5 μm, 4.6×100 mm) with a flow rate of 0.8 ml/min. Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

TABLE 5

Analytical LCMS data: $R_t$ is retention time in minutes; [MH]$^+$ means the mass of the compound;

| Compound No. | $R_t$ | [MH]$^+$ | Method |
|---|---|---|---|
| 1 | 3.66 | 427 | 1 |
| 2 | 3.39 | 441 | 1 |
| 3 | 3.67 | 371 | 1 |
| 4 | 3.39 | 385 | 1 |
| 5 | 9.24 | 493 | 2 |
| 7 | 8.78 | 441 | 2 |
| 8 | 7.67 | 242 | 2 |
| 9 | 3.44 | 385 | 3 |
| 14 | 9.01 | 441 | 2 |
| 15 | 7.28 | 440 | 2 |
| 16 | 7.20 | 470 | 2 |
| 18 | 3.03 | 471 | 3 |
| 19 | 3.01 | 471 | 3 |
| 21 | 2.81 | 415 | 3 |
| 22 | 3.17 | 401 | 3 |
| 24 | 3.51 | 441 | 3 |
| 29 | 10.21 | 495 | 2 |
| 31 | 4.55 | 496 | 5 |
| 33 | 7.78 | 538 | 2 |
| 34 | 10.12 | 483 | 2 |
| 35 | 8.98 | 467 | 2 |
| 36 | 7.54 | 512 | 2 |
| 39 | 9.27 | 487 | 2 |
| 41 | 9.78 | 469 | 2 |
| 43 | 7.34 | 484 | 2 |
| 48 | 8.98 | 385 | 2 |
| 49 | 3.48 | 372 | 3 |
| 51 | 7.58 | 454 | 2 |
| 55 | 10.27 | 439 | 2 |
| 56 | 3.08 | 457 | 4 |
| 57 | 3.53 | 403 | 3 |
| 58 | 2.86 | 468 | 3 |
| 59 | 10.64 | 453 | 2 |
| 60 | 3.43 | 421 | 3 |
| 61 | 3.11 | 399 | 3 |
| 62 | 3.64 | 399 | 3 |
| 63 | 3.33 | 413 | 3 |
| 64 | 3.25 | 451 | 3 |
| 65 | 2.96 | 429 | 3 |
| 68 | 3.36 | 402 | 3 |
| 69 | 5.55 | 419 | 5 |
| 70 | 3.52 | 428 | 3 |
| 72 | 8.71 | 415 | 2 |
| 76 | 3.24 | 384 | 3 |
| 77 | 3.64 | 455 | 3 |
| 78 | 3.58 | 429 | 3 |
| 79 | 3.37 | 415 | 3 |
| 80 | 3.11 | 455 | 3 |
| 81 | 3.33 | 431 | 3 |

E. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I):

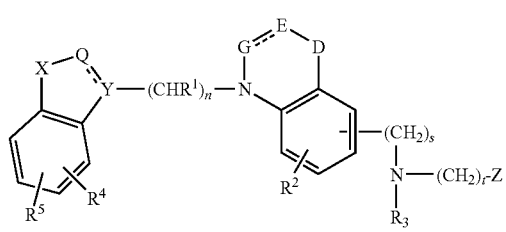

(I)

And any stereochemically isomeric form thereof, wherein n is 0, 1, 2, 3 or 4 and when n is 0 then a direct bond is intended, and wherein $R^1$ on each carbon of the —(CHR$^1$)$_n$— group is each independently selected from hydrogen, halo, hydroxy, amino, mono- or di(C$_{1-6}$alkyl)amino, C$_{1-6}$alkyl, aryl, heteroaryl, C$_{3-7}$cycloalkyl, arylC$_{1-6}$alkyl, heteroarylC$_{1-6}$alkyl, and C$_{3-7}$cycloalkyl-C$_{1-6}$alkyl, any of said mono- or di($C_{1-6}$alkyl)amino, $C_{1-6}$alkyl, aryl, heteroaryl, $C_{3-7}$cycloalkyl, aryl$C_{1-6}$alkyl, heteroaryl$C_{1-6}$alkyl or $C_{3-7}$cycloalkyl$C_{1-6}$alkyl being optionally and independently substituted with one or more, substituents selected from hydroxy, amino, aryl and heteroaryl;

s is 0 or 1 and when s is 0 then a direct bond is intended;
t is 0 or 1 and when t is 0 then a direct bond is intended;
$R^2$ is selected from
hydrogen, halo, cyano, amino;
polyhalo$C_{1-6}$alkyl;
$C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl,
$C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, substituents selected from halo, hydroxy, cyano, amino, mono- or
di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;
$R^3$ is hydrogen; $C_{1-6}$alkyl; aryl; heteroaryl; $C_{3-7}$cycloalkyl; $C_{1-6}$alkyl substituted with a substituent selected from hydroxy, amino, aryl and heteroaryl; or $C_{3-7}$cycloalkyl substituted with a substituent selected from hydroxy, amino, aryl and heteroaryl;
X is $NR^6$, S or O;

-G═E- is —$CR^7$═$CR^8$— and then the dotted line is a bond, —$CR^7R^9$—$CR^8R^{10}$—, —C(═O)—$CR^8R^{10}$— or —$CR^7R^9$—C(═O)—, wherein
$R^7$, $R^8$, $R^9$ or $R^{10}$ are each independently selected from:
hydrogen, halo, hydroxy, cyano;
polyhalo$C_{1-6}$alkyl;
$C_{1-6}$alkyl, $C_{3-7}$cycloalkyl, $C_{2-6}$alkenyl, aryl, heteroaryl, aryl$C_{1-6}$alkyl, heteroaryl$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, $C_{3-7}$cycloalkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl,
$C_{1-6}$alkyloxycarbonyl, $C_{3-7}$cycloalkyloxycarbonyl, aryloxycarbonyl, heteroaryloxycarbonyl, $C_{1-6}$alkylcarbonyloxy,
$C_{3-7}$cycloalkylcarbonyloxy, arylcarbonyloxy, heteroarylcarbonyloxy, mono- or di($C_{1-6}$alkyl)amino, $C_{1-6}$alkylcarbonylamino,
$C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, substituents selected from halo, hydroxy, cyano, amino, mono- or
di($C_{1-6}$alkyl)amino,
$C_{1-6}$alkyl, polyhalo$C_{1-6}$alkyl, aryl, heteroaryl, $C_{1-6}$alkyloxy,
$C_{1-6}$alkylcarbonyl,
$C_{1-6}$alkyloxycarbonyl and $C_{1-6}$alkylcarbonyloxy;

or wherein any of $R^7$ and $R^9$ together, or $R^8$ and $R^{10}$ together form a bivalent radical selected from —($CH_2$)$_2$—O—($CH_2$)$_2$—, —($CH_2$)$_2$—S—($CH_2$)$_2$— and —($CH_2$)$_2$—$NR^{21}$—($CH_2$)$_2$— wherein $R^{21}$ is hydrogen, $C_{1-6}$alkyl or $C_{1-6}$alkyloxyalkyl;

or wherein any of $R^7$ and $R^9$ together, or $R^8$ and $R^{10}$ together form a bivalent radical —($CH_2$)$_m$—, wherein m is 2, 3, 4, 5 or 6;

-D- is —O;

is —$CR^{19}$═C< and then the dotted line is a bond, —C(═O)—CH<, —C(═O)—N<, —$CHR^{19}$—CH<, or —$CHR^{19}$—N<, wherein each $R^{19}$ is independently hydrogen or $C_{1-6}$alkyl;

$R^4$ and $R^5$ are each independently hydrogen, halo, $C_{1-6}$alkyl, hydroxy$C_{1-6}$alkyl, polyhalo$C_{1-6}$alkyl, cyano, cyano$C_{1-6}$alkyl, hydroxy, amino, $C_{2-6}$alkenyl or $C_{1-6}$alkyloxy, or $R^4$ and $R^5$ together form a bivalent radical selected from methylenedioxy or ethylenedioxy;

$R^6$ is hydrogen, $C_{1-6}$alkyl, $C_{1-6}$alkylcarbonyl or $C_{1-6}$alkyloxycarbonyl;

Z is a radical selected from

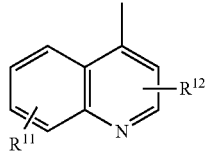
(a-1)

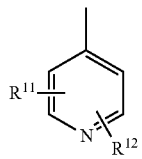
(a-2)

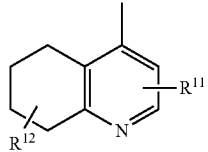
(a-3)

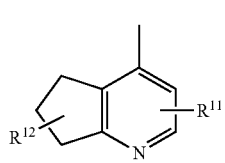
(a-4)

-continued

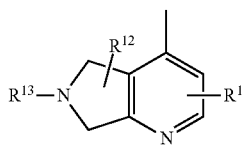
(a-5)

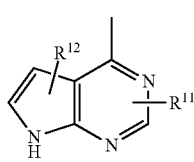
(a-6)

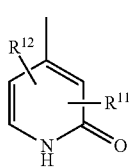
(a-7)

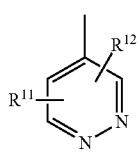
(a-8)

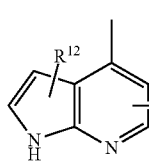
(a-9)

wherein
$R^{11}$ or $R^{12}$ are each independently selected from hydrogen, halo, hydroxy, amino, $C_{1-6}$alkyl, nitro, polyhalo$C_{1-6}$alkyl, cyano, cyano$C_{1-6}$alkyl, tetrazolo-$C_{1-6}$alkyl, aryl, heteroaryl, heteroaryl$C_{1-6}$alkyl, aryl(hydroxy)-$C_{1-6}$alkyl, heteroaryl(hydroxy)$C_{1-6}$alkyl, arylcarbonyl, heteroarylcarbonyl, $C_{1-6}$alkylcarbonyl, aryl$C_{1-6}$alkylcarbonyl, heteroaryl$C_{1-6}$alkylcarbonyl, $C_{1-6}$alkyloxy, $C_{3-7}$cycloalkylcarbonyl, $C_{3-7}$cycloalkyl(hydroxy)$C_{1-6}$alkyl, aryl$C_{1-6}$alkyloxy$C_{1-6}$alkyl, $C_{1-6}$alkyloxy$C_{1-6}$alkyloxy$C_{1-6}$alkyl, $C_{1-6}$alkylcarbonyloxy$C_{1-6}$alkyl, $C_{1-6}$alkyloxycarbonyl$C_{1-6}$alkyloxy$C_{1-6}$alkyl, hydroxy$C_{1-6}$alkyloxy$C_{1-6}$alkyl, $C_{1-6}$alkyloxycarbonyl$C_{2-6}$alkenyl, $C_{1-6}$alkyloxy$C_{1-6}$alkyl, $C_{1-6}$alkyloxycarbonyl, $C_{1-6}$alkylcarbonyloxy, aminocarbonyl, hydroxy$C_{1-6}$alkyl, amino$C_{1-6}$alkyl, hydroxycarbonyl, hydroxycarbonyl$C_{1-6}$alkyl and —$(CH_2)_v$—$(C(=O))_r$—$(CHR^{18})_u$—$NR^{14}R^{15}$, wherein
v is 0, 1, 2, 3, 4, 5, or 6 and when v is 0 then a direct bond is intended;
r is 0 or 1 and when r is 0 then a direct bond is intended;
u is 0, 1, 2, 3, 4, 5, or 6 and when u is 0 then a direct bond is intended;
$R^{18}$ is hydrogen or $C_{1-6}$alkyl;
$R^{14}$ and $R^{15}$ are each independently selected from hydrogen; $C_{1-12}$alkyl; $C_{1-6}$alkylcarbonyl; $C_{1-6}$alkylsulfonyl; aryl$C_{1-6}$alkylcarbonyl; $C_{3-7}$cycloalkyl; $C_{3-7}$cycloalkylcarbonyl; —$(CH_2)_k$—$NR^{16}R^{17}$; $C_{1-12}$alkyl substituted with a substituent selected from hydroxy, hydroxycarbonyl, cyano, $C_{1-6}$alkyloxycarbonyl, $C_{1-6}$alkyloxy, aryl or heteroaryl; or $C_{3-7}$cycloalkyl substituted with a substituent selected from hydroxy, $C_{1-6}$alkyloxy, aryl, amino, aryl$C_{1-6}$alkyl, heteroaryl or heteroaryl$C_{1-6}$alkyl, or $R^{14}$ and $R^{15}$ together with the nitrogen to which they are attached form morpholinyl; piperidinyl; pyrrolidinyl; piperazinyl; or piperazinyl substituted with a substituent selected from $C_{1-6}$alkyl, aryl$C_{1-6}$alkyl, aryl$C_{1-6}$alkyloxycarbonyl, heteroaryl$C_{1-6}$alkyl, $C_{3-7}$cycloalkyl and $C_{3-7}$cycloalkyl$C_{1-6}$ alkyl; wherein
k is 0, 1, 2, 3, 4, 5, or 6 and when k is 0 then a direct bond is intended;
$R^{16}$ and $R^{17}$ are each independently selected from hydrogen; $C_{1-12}$alkyl; aryl$C_{1-6}$alkyloxycarbonyl; $C_{3-7}$cycloalkyl; $C_{1-12}$alkyl substituted with a substituent selected from hydroxy, $C_{1-6}$alkyloxy, aryl, and heteroaryl; and $C_{3-7}$cycloalkyl substituted with a substituent selected from hydroxy, $C_{1-6}$alkyloxy, aryl, aryl$C_{1-6}$alkyl, heteroaryl, and heteroaryl$C_{1-6}$alkyl; or
$R^{16}$ and $R^{17}$ together with the nitrogen to which they are attached form morpholinyl, piperazinyl, or piperazinyl substituted with $C_{1-6}$alkyloxycarbonyl;
$R^{13}$ is hydrogen; $C_{1-6}$alkyl; $C_{3-7}$cycloalkyl; $C_{1-6}$alkyl substituted with a substituent selected from hydroxy, amino, $C_{1-6}$alkyloxy and aryl; or $C_{3-7}$cycloalkyl substituted with a substituent selected from hydroxy, amino, aryl and $C_{1-6}$alkyloxy;
aryl is phenyl or naphthalenyl;
each phenyl or naphthalenyl can optionally be substituted with one, two or three substituents each independently selected from halo, hydroxy, $C_{1-6}$alkyl, amino, polyhalo$C_{1-6}$alkyl and $C_{1-6}$alkyloxy; and
each phenyl or naphthalenyl can optionally be substituted with a bivalent radical selected from methylenedioxy and ethylenedioxy;
heteroaryl is pyridinyl, indolyl, quinolinyl, imidazolyl, furanyl, thienyl, oxadiazolyl, tetrazolyl, benzofuranyl or tetrahydrofuranyl;
each pyridinyl, indolyl, quinolinyl, imidazolyl, furanyl, thienyl, oxadiazolyl, tetrazolyl, benzofuranyl, or tetrahydrofuranyl can optionally be substituted with one, two or three substituents each independently selected from halo, hydroxy, $C_{1-6}$alkyl, amino, polyhalo$C_{1-6}$alkyl, aryl, aryl$C_{1-6}$alkyl or $C_{1-6}$alkyloxy; and
each pyridinyl, indolyl, quinolinyl, imidazolyl, furanyl, thienyl, benzofuranyl, or tetrahydrofuranyl can optionally be substituted with a bivalent radical selected from methylenedioxy or ethylenedioxy;
an N-oxide form thereof or an addition salt thereof.

2. The compound according to claim 1 wherein
$R^1$ on each carbon of the —$(CHR^1)_n$— group is each independently selected from hydrogen, halo, hydroxy, amino, mono- or di($C_{1-6}$alkyl)amino, $C_{1-6}$alkyl, aryl, heteroaryl, $C_{3-7}$cycloalkyl, aryl$C_{1-6}$alkyl, heteroaryl$C_{1-6}$ alkyl, and $C_{3-7}$cycloalkyl-$C_{1-6}$alkyl,
any of said mono- or di($C_{1-6}$alkyl)amino, $C_{1-6}$alkyl, heteroaryl, $C_{3-7}$cycloalkyl, aryl$C_{1-6}$alkyl, heteroaryl$C_{1-6}$alkyl or $C_{3-7}$cycloalkyl$C_{1-6}$alkyl being optionally and independently substituted with one or more, substituents selected from hydroxy, amino, aryl and heteroaryl;

$R^2$ is selected from
hydrogen, halo, cyano, amino;
polyhalo$C_{1-6}$alkyl;
$C_{1-6}$alkyl, $C_{3-7}$cycloalkyl, $C_{2-6}$alkenyl, aryl, heteroaryl, aryl$C_{1-6}$alkyl, heteroaryl-$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, aryloxy, heteroaryloxy, $C_{1-6}$alkylthio, arylthio, heteroarylthio, $C_{1-6}$alkylcarbonyl,
$C_{3-7}$cycloalkylcarbonyl, arylcarbonyl, heteroarylcarbonyl, $C_{1-6}$alkyloxycarbonyl, $C_{3-7}$cycloalkyloxycarbonyl, aryloxycarbonyl, heteroaryloxycarbonyl, $C_{1-6}$alkylcarbonyloxy, $C_{3-7}$cycloalkylcarbonyloxy, arylcarbonyloxy, heteroarylcarbonyloxy, mono- or di($C_{1-6}$alkyl)amino, $C_{1-6}$alkylcarbonylamino, $C_{1-6}$alkylcarbonylamino$C_{1-6}$alkyl, mono- or di($C_{1-6}$alkyl)aminocarbonyl and mono- or di($C_{1-6}$alkyl)aminocarbonyl$C_{1-6}$alkyl, any of said groups being optionally and independently substituted with one or more, substituents selected from halo, hydroxy, cyano, amino, mono- or di($C_{1-6}$alkyl)amino, $C_{1-6}$alkyl, polyhalo$C_{1-6}$alkyl, aryl, heteroaryl, $C_{1-6}$alkyloxy, $C_{1-6}$alkylcarbonyl, $C_{1-6}$alkyloxycarbonyl and $C_{1-6}$alkylcarbonyloxy;
X is $NR^6$;

-G≡E- is —$CR^7$=$CR^8$— and then the dotted line is a bond, —$CR^7R^9$—$CR^8R^{10}$—, —C(=O)—$CR^8R^{10}$— or —$CR^7R^9$—C(=O)—, wherein
$R^7$, $R^8$, $R^9$ or $R^{10}$ are each independently selected from:
hydrogen, halo, hydroxy, cyano;
polyhalo$C_{1-6}$alkyl;
$C_{1-6}$alkyl, $C_{3-7}$cycloalkyl, $C_{2-6}$alkenyl, aryl, heteroaryl, heteroaryl$C_{1-6}$alkyl, $C_{3-7}$cycloalkyl$C_{1-6}$alkyl, morpholinyl, piperidinyl, pyrrolidinyl, piperazinyl, $C_{1-6}$alkyloxy, $C_{3-7}$cycloalkyloxy, aryloxy, heteroaryloxy, $C_{1-6}$alkylthio, arylthio, heteroarylthio, $C_{1-6}$alkylcarbonyl, $C_{3-7}$cycloalkylcarbonyl, arylcarbonyl, heteroarylcarbonyl,
$C_{1-6}$alkyloxycarbonyl, $C_{3-7}$cycloalkyloxycarbonyl, aryloxycarbonyl, heteroaryloxycarbonyl, $C_{1-6}$alkylcarbonyloxy,
$C_{3-7}$cycloalkylcarbonyloxy, arylcarbonyloxy, heteroarylcarbonyloxy, mono- or di($C_{1-6}$alkyl)amino, $C_{1-6}$alkylcarbonylamino,
$C_{1-6}$alkylcarbonylamino$C_{1-6}$alkyl, mono- or di($C_{1-6}$alkyl)aminocarbonyl and mono- or
di($C_{1-6}$alkyl)aminocarbonyl$C_{1-6}$alkyl, any of said groups being optionally and independently substituted with one or more, substituents selected from halo, hydroxy, cyano, amino, mono- or di($C_{1-6}$alkyl)amino,
$C_{1-6}$alkyl, polyhalo$C_{1-6}$alkyl, aryl, heteroaryl, $C_{1-6}$alkyloxy,
$C_{1-6}$alkylcarbonyl,
$C_{1-6}$alkyloxycarbonyl and $C_{1-6}$alkylcarbonyloxy;
or wherein any of $R^7$ and $R^9$ together, or $R^8$ and $R^{10}$ together form a bivalent radical selected from
—$(CH_2)_2$—O—$(CH_2)_2$— and —$(CH_2)_2$—$NR^{21}$—$(CH_2)_2$— wherein $R^{21}$ is hydrogen, $C_{1-6}$alkyl or $C_{1-6}$alkyloxyalkyl;
or wherein any of $R^7$ and $R^9$ together, or $R^8$ and $R^{10}$ together form a bivalent radical selected from —$(CH_2)_m$—, wherein m is 2, 3, 4, 5 or 6;

$R^4$ and $R^5$ are each independently hydrogen, halo, $C_{1-6}$alkyl, cyano, cyano$C_{1-6}$alkyl, hydroxy, amino, or $C_{1-6}$alkyloxy, or $R^4$ and $R^5$ together form a bivalent radical selected from methylenedioxy or ethylenedioxy;

$R^6$ is hydrogen, $C_{1-6}$alkyl, $C_{1-6}$alkylcarbonyl or $C_{1-6}$alkyloxycarbonyl;

Z is a radical selected from

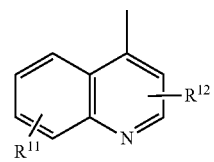
(a-1)

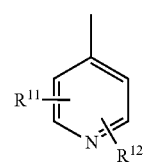
(a-2)

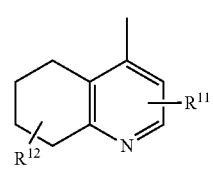
(a-3)

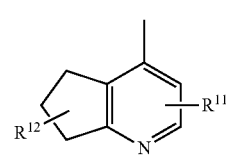
(a-4)

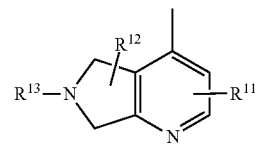
(a-5)

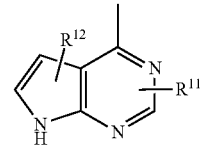
(a-6)

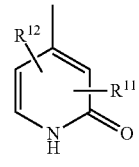
(a-7)

-continued

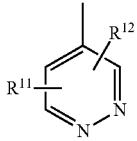
(a-8)

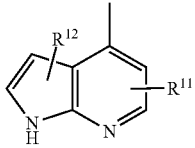
(a-9)

wherein
R$^{11}$ or R$^{12}$ are each independently selected from hydrogen, halo, hydroxy, amino, C$_{1-6}$alkyl, nitro, polyhaloC$_{1-6}$alkyl, cyano, cyanoC$_{1-6}$alkyl, tetrazolo-C$_{1-6}$alkyl, aryl, heteroaryl, heteroarylC$_{1-6}$alkyl, aryl(hydroxy)-C$_{1-6}$alkyl, heteroaryl(hydroxy)C$_{1-6}$alkyl, arylcarbonyl, heteroarylcarbonyl, C$_{1-6}$alkylcarbonyl, arylC$_{1-6}$alkylcarbonyl, heteroarylC$_{1-6}$alkylcarbonyl, C$_{1-6}$alkyloxy, C$_{3-7}$cycloalkylcarbonyl, C$_{3-7}$cycloalkyl(hydroxy)C$_{1-6}$alkyl, arylC$_{1-6}$alkyloxyC$_{1-6}$alkyl,
C$_{1-6}$alkyloxyC$_{1-6}$alkyloxyC$_{1-6}$alkyl, C$_{1-6}$alkylcarbonyloxyC$_{1-6}$alkyl, C$_{1-6}$alkyloxycarbonylC$_{1-6}$alkyloxyC$_{1-6}$alkyl, hydroxyC$_{1-6}$alkyloxyC$_{1-6}$alkyl, C$_{1-6}$alkyloxycarbonylC$_{2-6}$alkenyl, C$_{1-6}$alkyloxyC$_{1-6}$alkyl, C$_{1-6}$alkyloxycarbonyl, C$_{1-6}$alkylcarbonyloxy, aminocarbonyl, hydroxyC$_{1-6}$alkyl, aminoC$_{1-6}$alkyl, hydroxycarbonyl, hydroxycarbonylC$_{1-6}$alkyl and —(CH$_2$)$_v$—(C(=O))$_r$—(CHR$^{18}$)$_u$—NR$^{14}$R$^{15}$,
wherein
v is 0, 1, 2, 3, 4, 5, or 6 and when v is 0 then a direct bond is intended;
r is 0 or 1 and when r is 0 then a direct bond is intended;
u is 0, 1, 2, 3, 4, 5, or 6 and when u is 0 then a direct bond is intended;
R$^{18}$ is hydrogen or C$_{1-6}$alkyl;
R$^{14}$ and R$^{15}$ are each independently selected from hydrogen; C$_{1-12}$alkyl; C$_{1-6}$alkylcarbonyl; C$_{1-6}$alkylsulfonyl; arylC$_{1-6}$alkylcarbonyl; C$_{3-7}$cycloalkyl; C$_{3-7}$cycloalkylcarbonyl; —(CH$_2$)$_k$—NR$^{16}$R$^{17}$; C$_{1-12}$alkyl substituted with a substituent selected from hydroxy, hydroxycarbonyl, cyano, C$_{1-6}$alkyloxycarbonyl, C$_{1-6}$alkyloxy, aryl or heteroaryl; or C$_{3-7}$cycloalkyl substituted with a substituent selected from hydroxy, C$_{1-6}$alkyloxy, aryl, amino, arylC$_{1-6}$alkyl, heteroaryl or heteroarylC$_{1-6}$alkyl, or
R$^{14}$ and R$^{15}$ together with the nitrogen to which they are attached form morpholinyl; piperidinyl; pyrrolidinyl; piperazinyl; or piperazinyl substituted with a substituent selected from C$_{1-6}$alkyl, arylC$_{1-6}$alkyl, arylC$_{1-6}$alkyloxycarbonyl, heteroarylC$_{1-6}$alkyl, C$_{3-7}$cycloalkyl and C$_{3-7}$cycloalkylC$_{1-6}$alkyl;
wherein
k is 0, 1, 2, 3, 4, 5, or 6 and when k is 0 then a direct bond is intended;
R$^{16}$ and R$^{17}$ are each independently selected from hydrogen; C$_{1-6}$alkyl; arylC$_{1-6}$alkyloxycarbonyl; C$_{3-7}$cycloalkyl; C$_{1-12}$alkyl substituted with a substituent selected from hydroxy, C$_{1-6}$alkyloxy, aryl, and heteroaryl; and C$_{3-7}$cycloalkyl substituted with a substituent selected from hydroxy, C$_{1-6}$alkyloxy, aryl, arylC$_{1-6}$alkyl, heteroaryl, and heteroarylC$_{1-6}$alkyl; or
R$^{16}$ and R$^{17}$ together with the nitrogen to which they are attached form morpholinyl, piperazinyl, or piperazinyl substituted with C$_{1-6}$alkyloxycarbonyl.

3. The compound according to claim 1 or 2, wherein
R$^1$ on each carbon of the —(CHR$^1$)$_n$— group is each independently selected from hydrogen, hydroxy, amino, mono- or di(C$_{1-6}$alkyl)amino, C$_{1-6}$alkyl, arylC$_{1-6}$alkyl and heteroarylC$_{1-6}$alkyl; when any one R$^1$ substituent in the —(CHR$^1$)$_n$— group is different from hydrogen, the other R$^1$ substituents in the —(CHR$^1$)$_n$— group are each hydrogen;
s is 0;
t is 0 or 1;
R$^2$ is selected from hydrogen, halo, cyano, amino, mono- or di(C$_{1-6}$alkyl)amino, C$_{1-6}$alkyl, aryl, heteroaryl, arylC$_{1-6}$alkyl, heteroarylC$_{1-6}$alkyl, hydroxyC$_{1-6}$alkyl, polyhaloC$_{1-6}$alkyl, C$_{1-6}$alkyloxy, arylC$_{1-6}$alkyloxy, heteroarylC$_{1-6}$alkyloxy, C$_{1-6}$alkylthio, arylthio, C$_{1-6}$alkylcarbonyl, hydroxyC$_{1-6}$alkylcarbonyl, C$_{1-6}$alkyloxycarbonyl,
C$_{1-6}$alkylcarbonyloxy, C$_{1-6}$alkylcarbonylamino, morpholinyl, piperidinyl, pyrrolidinyl and piperazinyl;
R$^3$ is hydrogen or C$_{1-6}$alkyl;

is —CR$^{19}$=C< wherein R$^{19}$ is hydrogen or C$_{1-6}$alkyl;
R$^4$ and R$^5$ are each independently hydrogen, halo, C$_{1-6}$alkyl, polyhaloC$_{1-6}$alkyl, cyano, cyanoC$_{1-6}$alkyl, hydroxy, amino, or C$_{1-6}$alkyloxy;
Z is a radical selected from (a-1), (a-2), (a-3), (a-4) and (a-5);
R$^{11}$ or R$^{12}$ are each independently selected from hydrogen, hydroxy, amino, C$_{1-6}$alkyl, nitro, polyhaloC$_{1-6}$alkyl, cyano, aryl, arylC$_{1-6}$alkyl, aryl(hydroxy)C$_{1-6}$alkyl, arylcarbonyl, C$_{1-6}$alkyloxy, C$_{1-6}$alkyloxyC$_{1-6}$alkyl, C$_{1-6}$alkyloxycarbonyl, aminocarbonyl, hydroxyl-C$_{1-6}$alkyl, aminoC$_{1-6}$alkyl, hydroxycarbonyl and —(CH$_2$)$_v$—(C(=O))$_r$—(CH$_2$)$_u$—NR$^{14}$R$^{15}$;
v is 0 or 1;
r is 0 or 1;
u is 0;
R$^{14}$ and R$^{15}$ are each independently selected from hydrogen, C$_{1-6}$alkyl, —(CH$_2$)$_k$—NR$^{16}$R$^{17}$ and C$_{1-12}$alkyl substituted with hydroxy;
R$^{14}$ and R$^{15}$ together with the nitrogen to which they are attached form pyrrolidinyl;
k is 2;
R$^{16}$ and R$^{17}$ are each independently C$_{1-6}$alkyl;
R$^{13}$ is hydrogen or C$_{1-6}$alkyl;
aryl is phenyl or phenyl substituted with halo; and
heteroaryl is pyridinyl, indolyl, oxadiazolyl or tetrazolyl; and each pyridinyl, indolyl, oxadiazolyl or tetrazolyl can optionally be substituted with one substituent selected from C$_{1-6}$alkyl, aryl and arylC$_{1-6}$alkyl.

4. The compound of claim 1, wherein
n is 2;
each R$^1$ is hydrogen;

s is 0;
t is 0;
R$^2$ is selected from hydrogen halo, cyano, C$_{1-6}$alkyl, hydroxyC$_{1-6}$alkyl, C$_{1-6}$alkyloxy, C$_{1-6}$alkylcarbonylamino and morpholinyl;
R$^3$ is hydrogen;

is —CH═C<;
R$^4$ and R$^5$ are each independently hydrogen, C$_{1-6}$alkyl or C$_{1-6}$alkyloxy;
R$^6$ is hydrogen;
Z is a radical selected from (a-1), (a-2) and (a-4), and
R$^{11}$ or R$^{12}$ are each independently selected from hydrogen, hydroxy and hydroxyl-C$_{1-6}$alkyl.

5. The compound of claim 1 wherein X is NR$^6$.

6. The compound according to claim 1 wherein t is 0; s is 0; n is 2; X is NR$^6$, S or O; R$^1$ is hydrogen; R$^2$ is hydrogen or halo; R$^3$ is hydrogen; R$^4$ and R$^5$ are each independently hydrogen, C$_{1-6}$alkyl or C$_{1-6}$alkyloxy; R$^6$ is hydrogen;

is —CR$^{19}$═C< and then the dotted line is a bond, wherein R$^{19}$ is hydrogen; Z is a radical of formula (a-2) or (a-4); R$^{11}$ and R$^{12}$ are each independently selected from hydrogen, hydroxyl and hydroxyC$_{1-6}$alkyl.

7. The compound of claim 1 wherein

is —CR$^{19}$═C< and then the dotted line is a bond, wherein R$^{19}$ is hydrogen.

8. The compound of claim 1, wherein

is —CR$^7$═CR$^8$—, —CR$^7$R$^9$—CR$^8$R$^{10}$—, —C(═O)—CR$^8$R$^{10}$— or —CR$^7$R$^9$—C(═O)—, and R$^7$, R$^8$, R$^9$ or R$^{10}$ are each independently selected from
hydrogen, halo, hydroxy;
perhaloC$_{1-6}$alkyl;
C$_{1-6}$alkyl, C$_{3-7}$cycloalkyl, arylC$_{1-6}$alkyl, heteroarylC$_{1-6}$alkyl, C$_{1-6}$alkyloxy, aryl-C$_{1-6}$alkyloxy, heteroarylC$_{1-6}$alkyloxy, C$_{1-6}$alkylcarbonyl, mono- or di(C$_{1-6}$alkyl)amino,
C$_{1-6}$alkylcarbonylamino and morpholinyl, any of said groups optionally substituted with one or more, substituents selected from halo, hydroxy, amino, C$_{1-6}$alkyl, polyhaloC$_{1-6}$alkyl, aryl, heteroaryl and C$_{1-6}$alkyloxy;
or wherein any of R$^7$ and R$^9$ together, or R$^8$ and R$^{10}$ together form a bivalent radical —(CH$_2$)$_m$—, wherein m is 2, 3, 4, 5 or 6.

9. The compound according to any of claims 1 to 8, wherein

is —CR$^7$═CR$^8$—, —CR$^7$R$^9$—CR$^8$R$^{10}$—, —C(═O)—CR$^8$R$^{10}$ or —CR$^7$R$^9$—C(═O)—, and R$^7$, R$^8$, R$^9$ or R$^{10}$ are each independently selected from hydrogen, halo, C$_{1-6}$alkyl, perhaloC$_{1-6}$alkyl, or wherein any of R$^7$ and R$^9$ together, or R$^8$ and R$^{10}$ together form a bivalent radical —(CH$_2$)$_m$—wherein m is 2, 3, 4, 5 or 6.

10. The compound of claim 1 wherein

is —CH$_2$—CH$_2$—; —CH$_2$—CH(CH$_3$)—; —CH$_2$—C(CH$_3$)$_2$—; —CH$_2$—CH(CH$_2$OH)—; —CH$_2$—C(CH$_3$)(CH$_2$CH$_3$)—; —C(═O)—CH$_2$—; —C(═O)—CH(CH$_3$)—; —C(═O)—C(CH$_3$)$_2$—; —C(═O)—CF$_2$—;

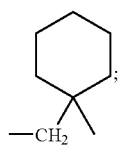 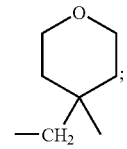 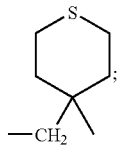

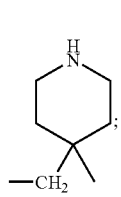 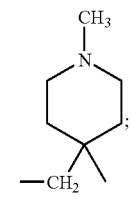

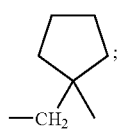 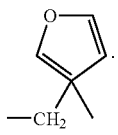

11. The compound according to claim 1, wherein the compound is selected from

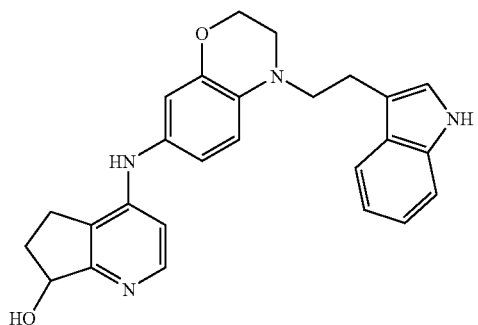

125
-continued
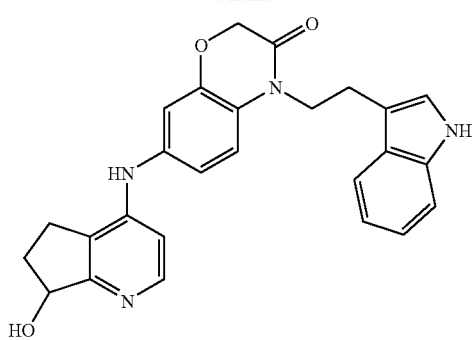
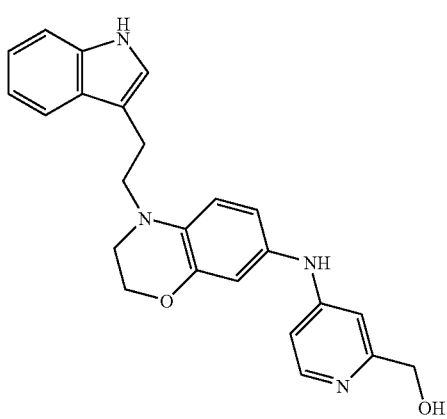
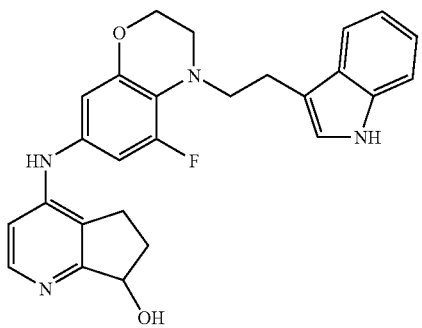
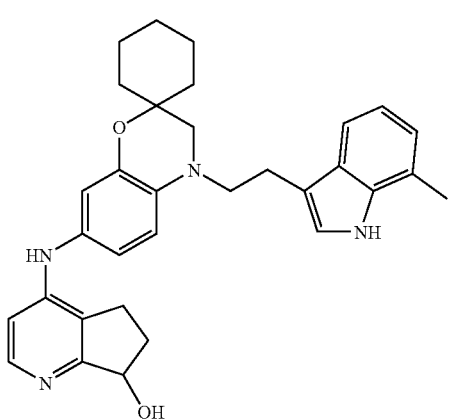
126
-continued
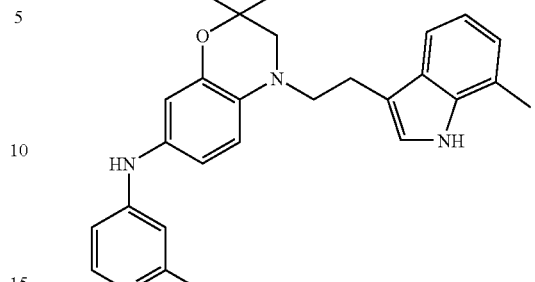
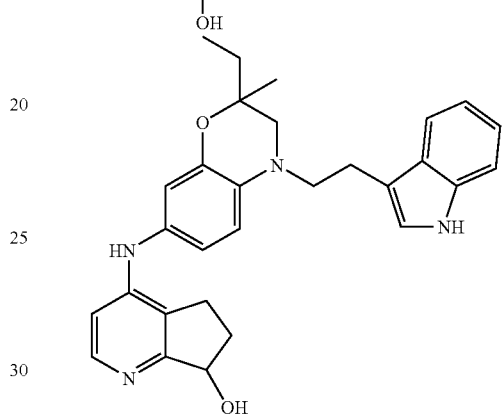
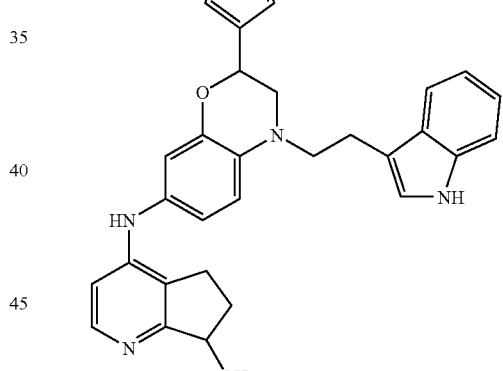
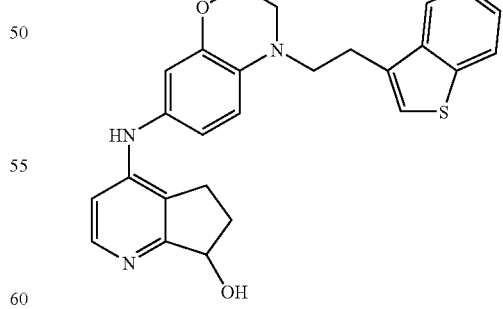
and any stereochemically isomeric form thereof;
an N-oxide form thereof, or an addition salt thereof.
12. A pharmaceutical composition comprising pharmaceutically acceptable carriers and a therapeutically effective amount of a compound of claim 1.

13. A method of treating cancer comprising administering a compound of claim 1 to a patient in need thereof, wherein the cancer is breast cancer, colorectal cancer, non-small cell lung cancer, prostate cancer, glioma, osteosarcoma- or acute myelogenous leukaemia.

14. A pharmaceutical composition comprising an anti-cancer agent and a therapeutically effective amount of a compound of claim 1, wherein the anticancer agent is selected from the group comprising platinum coordination compounds, taxane compounds, topoisomerase I inhibitors, topoisomerase II inhibitors, vinca alkaloids, nucleoside derivatives, alkylating agents, anthracylcine derivatives, IGF-1 receptor targets, tetracarcin derivatives, glucocorticoids, antibodies, estrogen receptor antagonist, estrogen receptor modulators, estrogen synthesis inhibitors, aromatase inhibitors, differentiating agents, DNA methyl transferase, antifolates, antibiotics, antimetabolites, apoptosis inducing agents, antiangiogenic agents, tubiline-binding agents, kinase inhibitors, farnesyltransferase inhibitors, histone deacetylase inhibitors, ubiquitin-proteasome inhibitors, yondelis, telomerase inhibitors, matrix metalloproteinase inhibitors, recombinant interleukins, MAPK inhibitors, retinoids, arsenic trioxide, asparaginase, steroids, gonadotropin releasing hormone agonist or antagonist, thalidomide, lenalidomide, Mercaptopurine, mitotane, pamidronate, pegademase, pegaspargase, rasburicase, BH3 mimetics, MEK inhibitors, colony-stimulating factor analogs.

15. A process for preparing a compound as claimed in claim 1, comprising a) reacting an intermediate of formula (II) with an intermediate of formula (III) or an appropriate acid addition salt thereof, wherein W is an appropriate leaving group

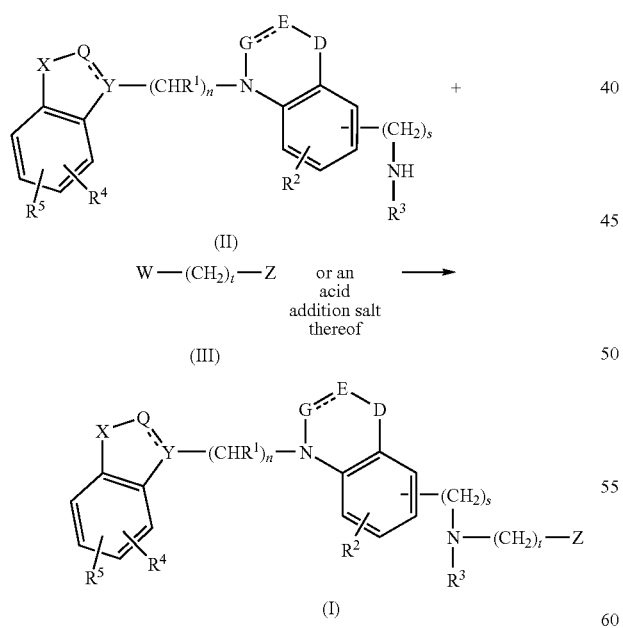

with the variables as defined in claim 1;

b) reacting an intermediate of formula (XIX) wherein P represents a suitable protective group, with an intermediate of formula (III) or an appropriate acid addition salt thereof, wherein W is an appropriate leaving group

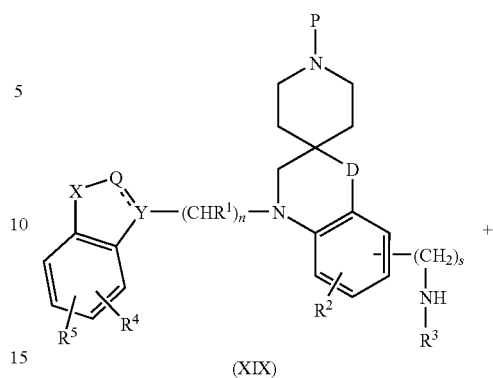

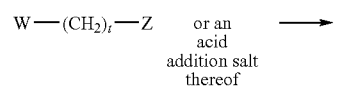

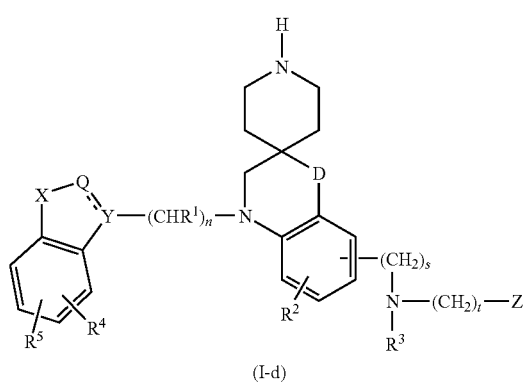

with the variables as defined in claim 1;

c) reacting an intermediate of formula (XX) with an intermediate of formula (III) or an appropriate acid addition salt thereof, wherein W is an appropriate leaving group

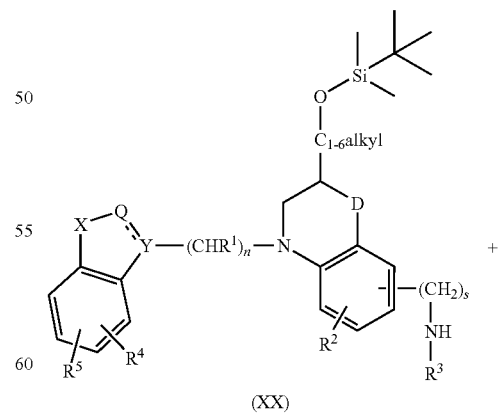

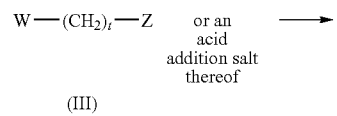

-continued

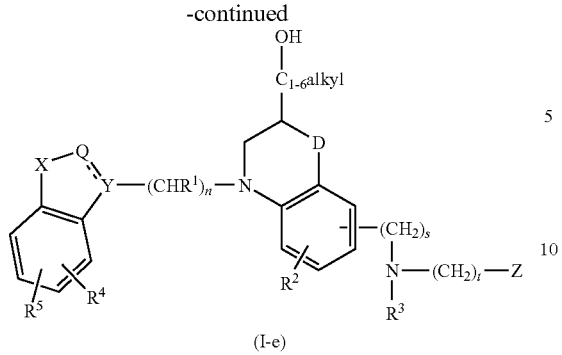

(I-e)

with the variables as defined in claim 1;

d) reacting an intermediate of formula (XXI) with a suitable deprotection agent for the alcohol function in the presence of a suitable solvent

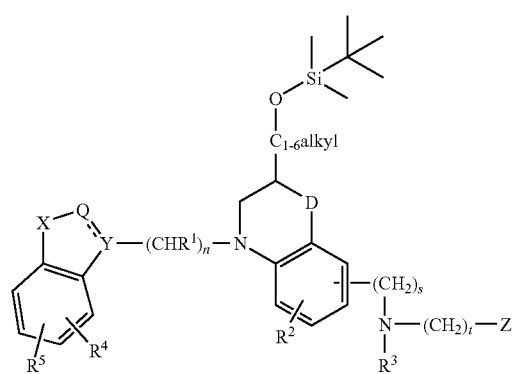

(XXI)

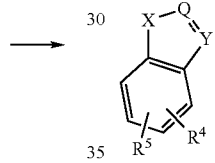

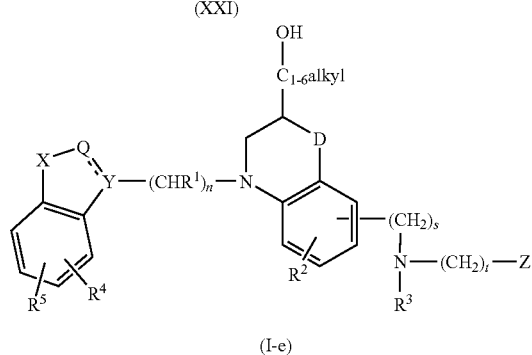

(I-e)

with the variables as defined in claim 1;

e) reacting an intermediate of formula (IV), wherein A is an appropriate leaving group, with an intermediate of formula (V

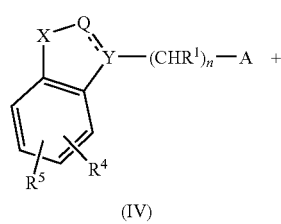

(IV)

-continued

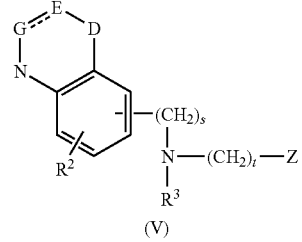

(V)

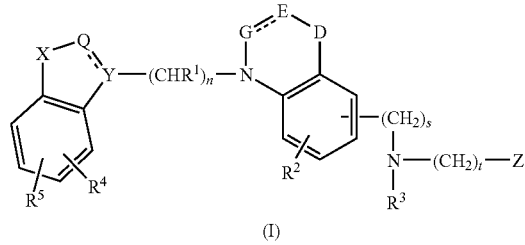

(I)

with the variables as defined in claim 1;

f) reducing an intermediate of formula (VI) with lithium aluminium hydride in a suitable solvent

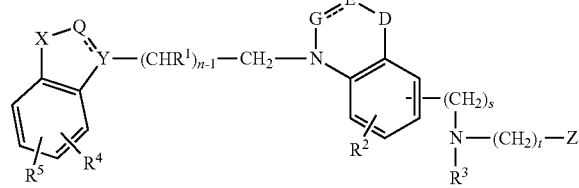

(VI)

(I-a)

with the variables as defined in claim 1;

g) reacting an appropriate carboxaldehyde of formula (VII), with an intermediate of formula (V), in the presence of an appropriate reducing reagent and a suitable solvent,

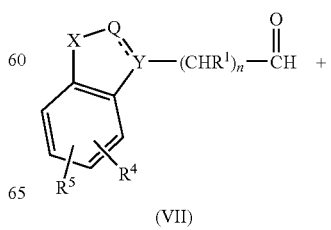

(VII)

-continued

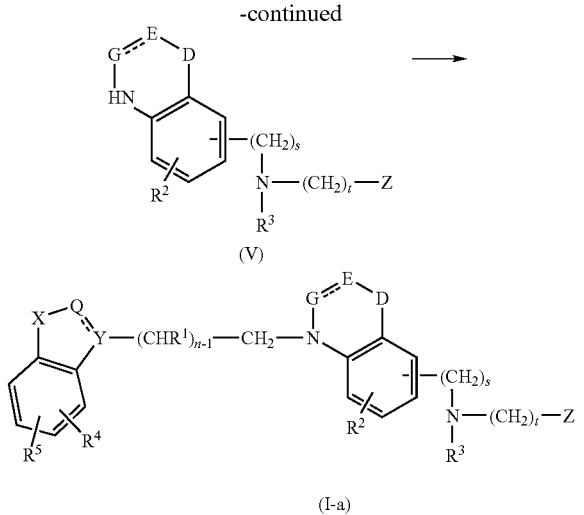

(V)

(I-a)

with the variables as defined in claim 1;
h) reacting an intermediate of formula (II) with an appropriate carboxaldehyde of formula HC(=O)Z to obtain compounds of formula (I) wherein t is 1, herein referred to as compounds of formula (I-b);
g) reducing an intermediate of formula (VIII) with lithium aluminium hydride in a suitable solvent (VIII)

(I-c)

with the variables as defined in claim 1;
h) converting a compound of formula (I) wherein

-G≡E- is —C(=O)—$CR^8R^{10}$ with $R^8$ and $R^{10}$ representing hydrogen, herein referred to as compounds of formula (I-f), into a compound of formula (I) wherein

-G≡E- is —$CH_2$—$CH_2$—, herein referred to as compounds of formula (I-g), by reaction with a suitable reducing agent,

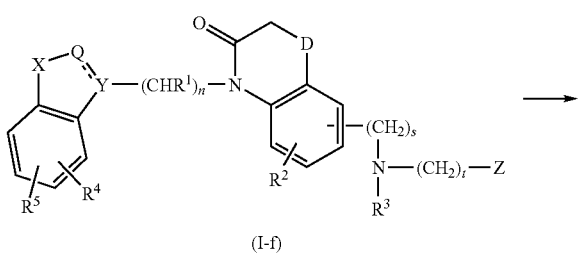

(I-f)

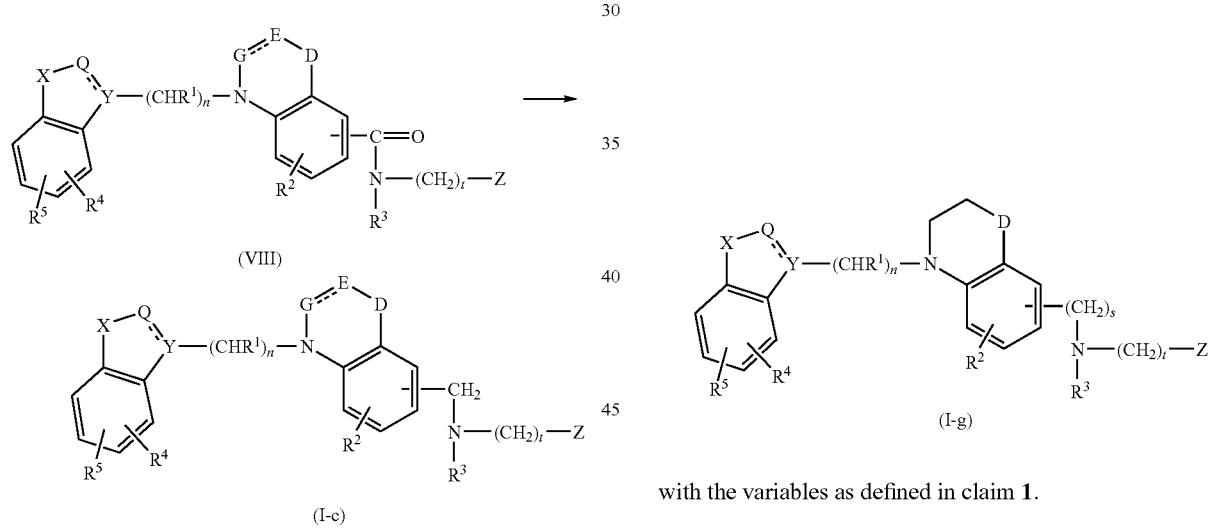

(I-g)

with the variables as defined in claim 1.

* * * * *